US009539287B2

(12) United States Patent
Gribble et al.

(10) Patent No.: US 9,539,287 B2
(45) Date of Patent: Jan. 10, 2017

(54) TRITERPENOIDS AND COMPOSITIONS CONTAINING THE SAME

(71) Applicant: Trustees of Dartmouth College, Hanover, NH (US)

(72) Inventors: Gordon W. Gribble, Lebanon, NH (US); Liangfeng Fu, West Lebanon, NH (US); Michael B. Sporn, Tunbridge, VT (US); Karen T. Liby, West Lebanon, NH (US)

(73) Assignee: Trustees of Dartmouth College, Hanover, NH (US)

( * ) Notice: Subject to any disclaimer, the term of this patent is extended or adjusted under 35 U.S.C. 154(b) by 114 days.

(21) Appl. No.: 14/496,488

(22) Filed: Sep. 25, 2014

(65) Prior Publication Data
US 2015/0011627 A1 Jan. 8, 2015

Related U.S. Application Data

(63) Continuation of application No. 13/466,456, filed on May 8, 2012, now Pat. No. 8,921,419.

(51) Int. Cl.
| A61K 31/56 | (2006.01) |
| C07J 63/00 | (2006.01) |
| A61K 35/44 | (2015.01) |
| C07C 61/29 | (2006.01) |
| C07C 62/38 | (2006.01) |
| C07C 229/50 | (2006.01) |
| C07C 235/78 | (2006.01) |
| C07C 255/47 | (2006.01) |
| C07C 291/10 | (2006.01) |
| C07C 317/44 | (2006.01) |
| C07C 323/55 | (2006.01) |
| A61K 35/12 | (2015.01) |
| C07C 62/32 | (2006.01) |
| C07J 71/00 | (2006.01) |

(52) U.S. Cl.
CPC ............ *A61K 35/44* (2013.01); *A61K 31/56* (2013.01); *A61K 35/12* (2013.01); *C07C 61/29* (2013.01); *C07C 62/32* (2013.01); *C07C 62/38* (2013.01); *C07C 229/50* (2013.01); *C07C 235/78* (2013.01); *C07C 255/47* (2013.01); *C07C 291/10* (2013.01); *C07C 317/44* (2013.01); *C07C 323/55* (2013.01); *C07J 63/008* (2013.01); *C07J 71/0005* (2013.01); *C07C 2103/52* (2013.01)

(58) Field of Classification Search
USPC .................. 514/169, 177; 552/510
See application file for complete search history.

(56) References Cited

U.S. PATENT DOCUMENTS

| 4,395,423 A | 7/1983 | Neumann .................. 424/304 |
| 4,808,614 A | 2/1989 | Hertel ............................ 514/45 |
| 5,013,649 A | 5/1991 | Wang et al. ................ 435/69.1 |
| 5,064,823 A | 11/1991 | Lee et al. ..................... 514/198 |
| 5,401,838 A | 3/1995 | Chou ............................ 536/281 |
| 5,426,183 A | 6/1995 | Kjell ......................... 536/285.5 |
| 5,464,826 A | 11/1995 | Grindey ......................... 514/50 |
| 5,521,294 A | 5/1996 | Wildfeur ...................... 536/187 |
| 5,597,124 A | 1/1997 | Kessel ............................ 241/30 |
| 5,603,958 A | 2/1997 | Morein et al. ............... 424/489 |
| 5,606,048 A | 2/1997 | Chou et al. ................ 536/271.1 |
| 5,972,703 A | 10/1999 | Long et al. .................. 435/372 |
| 6,025,395 A | 2/2000 | Breitner et al. ............. 514/570 |
| 6,303,569 B1 | 10/2001 | Greenwald et al. ............ 514/2 |
| 6,326,507 B1 | 12/2001 | Gribble et al. ............. 558/415 |
| 6,485,756 B1 | 11/2002 | Aust et al. .................... 424/725 |
| 6,552,075 B2 | 4/2003 | Gribble et al. ............. 514/522 |
| 6,974,801 B2 | 12/2005 | Honda et al. .................. 514/25 |
| 7,176,237 B2 | 2/2007 | Honda et al. ................ 514/519 |
| 7,265,096 B2 | 9/2007 | Gallop et al. .................. 514/49 |
| 7,288,568 B2 | 10/2007 | Gribble et al. ............. 514/519 |
| 7,435,755 B2 | 10/2008 | Konopleva et al. ......... 514/510 |
| 7,795,305 B2 | 9/2010 | Konopleva et al. ......... 514/510 |
| 7,863,327 B2 | 1/2011 | Gribble et al. ............. 514/521 |
| 7,915,402 B2 | 3/2011 | Anderson et al. ........... 540/519 |
| 7,943,778 B2 | 5/2011 | Jiang et al. ................. 548/247 |
| 8,034,955 B2 | 10/2011 | Gribble et al. ............. 548/241 |
| 8,129,429 B2 | 3/2012 | Sporn et al. ................ 514/510 |
| 8,299,046 B2 | 10/2012 | Sporn et al. .................. 514/63 |
| 8,921,340 B2 | 12/2014 | Sporn et al. .................. 514/63 |
| 2003/0119732 A1 | 6/2003 | Konopleva et al. ......... 514/510 |
| 2005/0276836 A1 | 12/2005 | Wilson et al. ............... 424/434 |
| 2005/0288363 A1 | 12/2005 | Gribble et al. ............. 558/303 |
| 2007/0155742 A1 | 7/2007 | Honda et al. ................ 514/519 |
| 2008/0220057 A1 | 9/2008 | Gribble et al. ............. 514/522 |
| 2008/0233195 A1 | 9/2008 | Sporn et al. ................ 424/486 |
| 2008/0261985 A1 | 10/2008 | Honda et al. ................ 548/400 |

(Continued)

FOREIGN PATENT DOCUMENTS

| CN | 101117348 | 2/2006 |
| DE | 10 2005 041613 | 3/2007 |

(Continued)

OTHER PUBLICATIONS

Abraham, N. G. and Kappas, A. "Heme Oxygenase and the Cardiovascular-Renal System" Free Radical Biology and Medicine 2005 39(1):1-25.

Agarwal, N. and Mehta, K. "Possible Involvement of Bcl-2 Pathway in Retinoid X Receptor Alpha-Induced Apoptosis of HL-60 Cells" Biochemistry and Biophysical Research Communications 1997 230(2):251-253.

Ahmad et al. "Triterpenoid CDDO-Me Blocks the NF-κB Pathway by Direct Inhibition of IKKβ on Cys-179" The Journal of Biological Chemistry 2006 281:35764-35769.

(Continued)

*Primary Examiner* — Barbara P Badio
(74) *Attorney, Agent, or Firm* — Licata & Tyrrell P.C.

(57) ABSTRACT

The present invention provides triterpenoids produced from natural compounds such as oleanolic acid, ursolic acid, betulinic acid, and hederagenin.

2 Claims, No Drawings

(56) References Cited

U.S. PATENT DOCUMENTS

| | | | |
|---|---|---|---|
| 2009/0018146 A1 | 1/2009 | Gutterman et al. | 540/519 |
| 2009/0048204 A1 | 2/2009 | Walling et al. | 514/49 |
| 2009/0048205 A1 | 2/2009 | Meyer et al. | 514/49 |
| 2009/0060873 A1 | 3/2009 | Sporn et al. | 424/85.6 |
| 2009/0093447 A1 | 4/2009 | Konopleva et al. | 514/510 |
| 2009/0326063 A1 | 12/2009 | Sporn et al. | 514/529 |
| 2010/0048887 A1 | 2/2010 | Anderson et al. | 540/8 |
| 2010/0048892 A1 | 2/2010 | Anderson et al. | 544/154 |
| 2010/0048911 A1 | 2/2010 | Jiang et al. | 548/250 |
| 2011/0245206 A1 | 10/2011 | Jiang et al. | 514/112 |
| 2011/0245233 A1 | 10/2011 | Anderson et al. | 514/212.04 |

FOREIGN PATENT DOCUMENTS

| | | |
|---|---|---|
| EP | 0272891 A2 | 6/1988 |
| EP | 0329348 B1 | 7/1995 |
| EP | 0376518 B1 | 11/1995 |
| EP | 0576230 B1 | 4/1996 |
| EP | 0577303 B1 | 10/1997 |
| EP | 0712860 B1 | 12/2001 |
| WO | WO 91/15498 | 10/1991 |
| WO | WO 96/05290 | 2/1996 |
| WO | WO 98/00173 | 1/1998 |
| WO | WO 98/32762 | 7/1998 |
| WO | WO 99/33483 | 7/1999 |
| WO | WO 99/65478 | 12/1999 |
| WO | WO 00/73253 | 12/2000 |
| WO | WO 01/01135 | 1/2001 |
| WO | WO 01/28579 | 4/2001 |
| WO | WO 02/03996 | 1/2002 |
| WO | WO 02/47611 | 6/2002 |
| WO | WO 03/043631 | 5/2003 |
| WO | WO 03/059339 | 7/2003 |
| WO | WO 2005/042002 | 5/2005 |
| WO | WO 2006/029221 | 3/2006 |
| WO | WO 2007/005879 | 1/2007 |
| WO | WO 2007/069895 | 6/2007 |
| WO | WO 2008/111497 | 9/2008 |
| WO | WO2009/023835 A2 | 2/2009 |
| WO | WO2010/093944 A2 | 8/2010 |

OTHER PUBLICATIONS

Al-alami et al. "Divergent Effect of Taxol on Proliferation, Apoptosis and Nitric Oxide Production in MHH225 CD34 Positive and U937 CD34 Negative Human Leukemia Cells" Leukemia Research 1998 22:939-945.

Ambs et al. "p53 and Vascular Endothelial Growth Factor Regulate Tumor Growth of NOS2-Expressing Human Carcinoma Cells" Nature Medicine 1998 4(12):1371-1376.

Amstutz et al. "Die Position 5 Im Oxotremorin-Gerust: Eine Zentrale Stelle Fur Die Steuerung Der Aktivitat Am Muscarinischen Rezeptor" Helvitica Chemi Acta 1987 70:2232-2244.

Andreeff et al. "Expression of Bcl-2-Related Genes in Normal and AML Progenitors: Changes Induced by Chemotherapy and Cationic Acid" Leukemia 1999 13:1881-1892.

Andreeff et al. "PPARgamma Nuclear Receptor as a Novel Molecular Target in Leukemias" 2002 Keystone Symposia Abstract No. 501, 2002.

Andreef, M. "Acute Myeloid Leukemia" Cancer Treatment 1995 911-922.

Araujo et al. "Systemic Rather than Local Heme Oxygenase-1 Overexpression Improves Cardiac Allograft Outcomes in a New Transgenic Mouse" The Journal of Immunology 2003 171(3):1572-1580.

Bach, F. H. "Heme Oxygenase-1 and Transplantation Tolerance" Human Immunology 2006 67(6):430-432.

Baeuerle, P. A. And Baltimore, D. "NF-κB: Ten Years After" Cell 1996 87:13-20.

Bagasra et al. "Activation of the Inducible Form of Nitric Oxide Synthase in the Brains of Patients with Multiple Sclerosis" Proceedings of the National Academy of Science USA 1995 92:12041-12045.

Baldwin Jr., A. S. "The NF-κB and IκB Proteins: New Discoveries and Insights" Annual Review of Immunology 1996 14:649-681.

Bargou et al. "Constitutive Nuclear Factor κB-RelA Activation is Required for Proliferation and Survival of Hodgkin's Disease Tumor Cells" The Journal of Clinical Investigation 1997 100:2961-2969.

Barkett, M. and Gilmore, T. D. "Control of Apoptosis by Rel/NF-κB Transcription Factors" Oncogene 1999 18:6910-6924.

Barnes, P. J. and Karin, M. "Nuclear Factor-κB—A Pivotal Transcription Factor in Chronic Inflammation Diseases" The New England Journal of Medicine 1997 336:1066-1071.

Beal, M. F. "Mitochondria, Free Radicals, and Neurodegeneration" Current Opinion in Neurobiology 1996 6:661-666.

Beran et al. "Topotecan and Cytarabine is an Active Combination Regimen in Myelodysplastic Syndromes and Chronic Myelomonocytic Leukemia" Journal of Clinical Oncology 1999 17(9):2819-2830.

Bliard et al. "Glycosylation of Acids Under Phase Transfer Conditions. Partial Synthesis of Saponins" Tetrahedron Letters 1994 35:6107-6108.

Bogdan et al. "Contrasting Mechanisms for Suppression of Macrophage Cytokine Release by Transforming Growth Factor-Beta and Interleukin-10" The Journal of Biological Chemistry 1992 267:23301-23308.

Bogdan, C. and Ding, A. "Taxol, a Microtubule-Stabilizing Antineoplastic Agent, Induces Expression of Tumor Necrosis Factor α and Interleukin-1 in Macrophages" Journal of Leukocyte Biology 1992 52(1):119-121.

Bollag, W. and Holdener, E. E. "Retinoids in Cancer Prevention and Therapy" Annals of Oncology 1992 3:513-526.

Boolbol et al. "Cyclooxygenase-2 Overexpression and Tumor Formation are Blocked by Sulindac in a Murine Model of Familial Adenomatous Polyposis" Cancer Research 1996 56(11):2556-2560.

Bore et al. "The Anti-Inflammatory Triterpenoid Methyl 2-Cyano-3,12-Dioxoolean 1,9(11)-dien-28-oate Methanol Solvate Hydrate" Acta Crystallography C. 2002 58 (Pt 3) :o199-o200.

Brookes et al. "The Triterpenoid 2-cyano-3,12-dioxooleana-1,9-dien-28-oic Acid and Its Derivatives Elicit Human Lymphoid Cell Apoptosis Through a Novel Pathway Involving the Unregulated Mitochondrial Permeability Transition Pore" Cancer Research 2007 67:1793-1802.

Bruder, S. P. and Caplan, A. I. "Terminal Differentiation of Osteogenic Cells in the Embryonic Chick Tibia is Revealed by a Monoclonal Antibody Against Osteocytes" Bone 1990 11:189-198.

Bruder, S. P. and Caplan, A. I. "First Bone Formation and the Dissection of an Osteogenic Lineage in the Embryonic Chick Tibia is Revealed by Monoclonal Antibodies Against Osteoblasts" Bone 1989 10:359-375.

Bruder et al. "Terminal Osteogenic Cell Differentiation in Culture Requires Beta-Glycerol Phosphate" Transactions of the Annual Meeting—Orthopaedic Research Society 1991 16:58.

Bruland et al. "Expression and Characteristics of a Novel Human Osteosarcoma-Associated Cell Surface Antigen" Cancer Research 1988 48:5302-5308.

Buzoni-Gatel et al. "Intraepithelial Lymphocytes Traffic to the Intestine and Enhance Resistance to Toxoplasma Gondii Oral Infection" The Journal of Immunology 1999 162:5846-5852.

Buzoni-Gatel et al. "Murine Ileitis After Intracellular Parasite Infection is Controlled by TGF-Beta-Producing Intraepithelial Lymphocytes" Gastroenterology 2001 120:914-924.

Cai et al. "A New Protecting Group for Alkynes: Orthogonally Protected Dialkynes" Helvetica Chimica Acta 1995 78:732-757.

Carter et al. "Expression of Survivin, A member of the Inhibitor of Apoptosis (IAP) Family of Caspase Inhibitors is Expressed in AML and Regulated by Cytokines and ATRA" Blood 1999 94 (Suppl 1) :479a, Abstract #2142.

Cassady, J. M. and Suffness, M. In *Anticancer Agents Based on Natural Product Models*; Academic Press, NY, 254-269, 1980.

Castaigne et al. "All-Trans Retinoic Acid as a Differentiation Therapy for Acute Promyelocytic Leukemia" Blood 1990 76(9):1704-1709.

(56) References Cited

OTHER PUBLICATIONS

Chauhan et al. "The Bortezomib/Proteasome Inhibitor PS-341 and Triterpenoid CDDO-Im Induce Synergistic Anti-Multiple Myeloma (MM) Activity and Overcome Bortezomib Resistance" Blood 2004 103:3158-3166.
Chen et al. "Chondrogenesis in Chick Limb Bud Mesodermal Cells: Reciprocal Modulation by Activin and Inhibin" Experimental Cell Research 1993 206:119-127.
Chen et al. "Stimulation of Chondrogenesis in Limb Bud Mesoderm Cells by Recombinant Human Bone Morphogenetic Protein 2B(BMP-2B) and Modulation by Transforming Growth Factor Beta 1 and Beta 2" Experimental Cell Research 1991 195:509-515.
Cheng et al. "Differentiation of Human Bone Marrow Osteogenic Stromal Cells in vitro: Induction of the Osteoblast Phenotype by Dexamethasone" Endocrinology 1994 134:277-286.
Chintharlapalli et al. "2-Cyano-3,12-dioxoolean-1,9-dien-28-oic Acid and Related Compounds Inhibit Growth of Colon Cancer Cells Through Peroxisome Proliferator-Activated Receptor Gamma-Dependent and -Independent Pathways" Molecular Pharmacology 2005 68:119-128.
Chung, J. Y. L. and Wasicak, J. T. "Synthesis of Chiral α-Acetylenic Cyclic Amines from α-Amino Acids: Applications to Differentially Constrained Oxotremorine Analogues as Muscarinic Agents" Tetrahedron Letters 1990 31:3957-3960.
Clinton et al. "Steroidal[3,2-c]pyrazoles. II. Androstanes, 19-Norandrostanes and Their Unsaturated Analogs" Journal of the American Chemical Society 1961 83:1478-1491.
Corey, E. J. and Ruden, R. A. "Stereoselective Methods for the Synthesis of Terminal cis and trans Enye Units" Tetrahedron Letters 1973:1495-1499.
Coyle, J. T. and Puttfarcken, P. "Oxidative Stress, Glutamate, and Neurodegenerative Disorders" Science 1993 262:689-695.
Dean, P.D.G. "Halogenolysis of Methyl Glycyrrhetate with Lithium Iodidedimethylformamide" Journal of the Chemical Society 1965:6655-6659.
Dezube et al. "Interim Results of a Phase I Trial with a Novel Orally Administered Synthetic Triterpenoid RTA 402 (CDDO-Me) in Patients with Solid Tumors and Lymphoid Malignancies" Journal of Clinical Oncology 2007 ASCO Annual Meeting Proceeding 25(18S) :14101.
Ding et al. "Macrophage Deactivating Factor and Transforming Growth Factors-$\beta_1$, -$\beta_2$ and -$\beta_3$ Inhibit Induction of Macrophage Nitrogen Oxide Synthesis by IFN-$\gamma^1$" Journal of Immunology 1990 145 (3) :940-944.
Dinkova-Kostova et al. "Extremely Potent Triterpenoid Inducers of the Phase 2 Response: Correlations of Protection Against Oxidant and Inflammatory Stress" The Proceedings of the National Academy of Science USA 2005 102(12):4584-4589.
Drach et al. "Induction of Differentiation in Myeloid Leukemia Cell Lines and Acute Promyelocytic Leukemia Cells by Liposomal All-Trans-Retinoic Acid" Cancer Research 1993 53:2100-2104.
Dragnev et al. "The Retinoids and Cancer Prevention Mechanisms" The Oncologist 2000 5:361-368.
Drefahl and Huneck "Nor-olea-12-enol-17-amin und Olea-12-enol-28-amin" Chemisch Berichte 1958 91:278-281.
DuBois et al. "$G_1$ Delay in Cells Overexpressing Prostaglandin Endoperoxide Synthase-$2^1$" Cancer Research 1996 56(4):733-737.
DuBois et al. "Increased Cyclooxygenase-2 Levels in Carcinogen-Induced Rat Colonic Tumors" Gastroenterology 1996 110:1259-1262.
Dutcher et al. "Pentacyclic Triterpene Synthesis. 5. Synthesis of Optically Pure Ring AB Precursors" Journal of Organic Chemistry 1976 41:2663-2669.
Elliot et al. "The Triterpenoid CDDO Inhibits Expression of Matrix Metalloproteinase-1, Matrix Metalloproteinase-13 and Bcl-3 in Primary Human Chondrocytes" Arthritis Research Therapy 2003 5:R285-R291.
Elsawa et al. "Preferential Inhibition of Malignant Cell Growth by CDDO in Waldenstrom Macroglobulinemia" Blood 2006 108(11):2528.
Elstner et al. "Ligands for Peroxisome ProliferatorActivated Receptorgamma and Retinoic Acid Receptor Inhibit Growth and Induce Apoptosis of Human Breast Cancer Cells in vitro and in BNX Mice" Proceedings of the National Academy Science USA 1998 95:8806-8811.
Embleton et al. "Antitumor Reactions of Monoclonal Antibody Against a Human Osteogenic-Sarcoma Cell Line" British Journal of Cancer 1981 43:4801-4805.
Engel et al. "Quantitation of Minimal Residual Disease in Acute Myelogenous Leukemia and Myelodysplastic Syndromes in Complete Remission by Molecular Cytogenetics of Progenitor Cells" Leukemia 1999 13:568-577.
Estey et al. "Molecular Remissions Induced by Liposomal-Encapsulated All-Trans Retinoic Acid in Newly Diagnosed Acute Promyelocytic Leukemia" Blood 1999 94:2230-2235.
Estey et al. "Randomized Phase II Study of Fludarabine + Cytosine Arabinoside + Idarubicin + All-Trans Retinoic Acid + Granulocyte-Colony Stimulating Factor in Poor Prognosis Newly Diagnosed Acute Myeloid Leukemia and Myelodysplastic Syndrome" Blood 1998 93(8):2478-2484.
Favaloro et al. "Design and Synthesis of Tricyclic Compounds with Enone Functionalities in Rings A and C: A Novel Class of Highly Active Inhibitors of Nitric Oxide Production in Mouse Marcophages" Journal of Medicinal Chemistry 2002 45:4801-4805.
Finkbeiner, H. L. and Stiles, M. "Chelation as a Driving Force in Organic Reactions. IV. Synthesis of a α-Nitro Acids by Control of the Carboxylastion-Decarboxylation Equilibrium" Journal of the American Chemical Society 1963 85:616-622.
Genain, C. P. and Hauser, S. L. "Creation of a Model for Multiple Sclerosis in Callithrix Jacchus Marmosets" Journal of Molecular Medicine 1997 75:187-197.
Ghosh et al. "NF-κB and Rel Proteins: Evolutionarily Conserved Mediators of Immune Response" Annual Review of Immunology 1998 16:225-260.
Grieco, P. A. and Speake, J. D. "Synthetic Studies on Quassinoids: Total Synthesis and Biological Evaluation of (+)-Des-D-Chaparrinone" The Journal of Organic Chemistry 1998 63:5929-5936.
Gura, T. "Systems for Identifying New Drugs are Often Faulty" Science 1997 278:1041-1042.
Guttridge et al. "NF-kappaB Controls Cell Growth and Differentiation Through Transcriptional Regulation of Cyclin D1" Molecular and Cellular Biology 1999 19:5785-5799.
Hail et al. "Evidence Supporting a Role for Calcium in Apoptosis Induction by the Synthetic Triterpenoid 2-cyano-3,12-dioxooleana-1,9-dien-28-oic Acid (CDDO)" The Journal of Biological Chemistry 2004 279:11179-11187.
Heiner et al. "Localization of GD2-Specific Monoclonal Antibody 3F8 in Human Osteosarcoma" Cancer Research 1987 47:5377-5384.
Hidvegi et al. "A Low Temperature Method of Isolating Normal Human Articular Chondrocytes" Osteoarthritis and Cartilage 2006 14:89-93.
Hinz et al. "NF-kappaB Function in Growth Control: Regulation of Cyclin D1 Expression and G0/G1-to-S-phase Transtion" Molecular and Cellular Biology 1999 19:2690-2698.
Hirota et al. "Stereoselective Total Synthesis of (±)- eperuane-8β,15-diol$^1$" Bulletin of the Chemical Society of Japan 1988 61:4023-4028.
Hirota et al. "Suppression of Tumor Promoter-Induced Inflammation of Mouse Ear by Ursolic Acid and 4,4-dimethycholestane Derivatives" Agricultural and Biological Chemistry 1990 54:1073-1075.
Hirota et al. "Total Synthesis of (±)-amarolide, a Quassinoid Bitter Principle" Journal of Organic Chemistry 1991 56:1119-1127.
Honda et al. "A Novel Dicyanotriterpenoid, 2-cyano-3,12-dioxooleanan-1,9(11)-dien-28-onitrile, Active at Picomolar Concentrations for Inhibition of Nitric Oxide Production" Bioorganic & Medicinal Chemistry Letters 2002 12:1027-1030.
Honda et al. "Design and Synthesis of 2-cyano-3,12-dioxoolean-1,9-dien-28-oic Acid, A Novel and Highly Active Inhibitor of Nitric Oxide Production in Mouse Marcophages" Bioorganic & Medicinal Chemistry Letters 1998 8(19):2711-2714.

(56) References Cited

OTHER PUBLICATIONS

Honda et al. "Efficient Synthesis of (-31 )- and (+)-Tricyclic Compounds with Enome Functionalities in Rings A and C. A Novel Class of Orally Active Anti-Inflammatory and Cancer Chemopreventive Agents" Organic and Bimolecular Chemistry 2003 1:4384-4391.

Honda et al. "New Enone Derivatives of Oleanolic Acid and Ursolic Acid as Inhibitors of Nitric Oxide Production in Mouse Marcophages" Bioorganic & Medicinal Chemistry Letters 1997 7:1623-1628.

Honda et al. "Novel Synthetic Oleanane and Ursane Triterpenoids with Various Enone Functionalities in Ring A as Inhibitors of Nitric Oxide Production in Mouse Marcophages" Journal of Medicinal Chemistry 2000 43:1866-1877.

Honda et al. "Novel Synthetic Oleanane Triterpenoids: A Series of Highly Active Inhibitors of Nitric Oxide Production in Mouse Macrophages" Bioorganic & Medicinal Chemistry Letters 1999 9(24):3429-3434.

Honda et al. "Synthesis of (±)-3,3-ethylenedioxy-14α-hydroxy-5-picrasene-11,16-dione, a 14αH-Picrasane Derivative" Chemistry Letters 1981:299-302.

Honda et al. "Synthesis of a Novel Dicyano Abietane Analogue: a Potential Antiinflammatory Agent" The Journal of Organic Chemistry 2006 71:3314-3316.

Honda et al. "Synthetic Oleanane and Ursane Triterpenoids with Modified Rings A and C: a Series of Highly Active Inhibitors of Nitric Oxide Production in Mouse Macrophages" The Journal of Medicinal Chemistry 2000 43:4233-4246.

Honda et al. "An Efficient Synthesis of Tricyclic Compounds, (±)-(4aβ,8aβ, 10aα)-1,2,3,4,4a,6,7,8,8a,9,10,10a,—Dodecahydro-1,1,4a-Trimethyl-2-Oxophenanthrene-8a-Carboxylic Acid, Its Methyl Ester, and (±)-(4aβ, 8aβ, 10aα)-3,4,4a,6,7,8,8a,9,10,10a-Decahydro-8a-Hydroxymethyl- 1,1,4a-Trimethylphenanthren-2 (1H)-One" Organic Preparations and Procedures International 2005 37:546-550.

Hosoi et al. "Detection of Human Osteosarcoma-Associated Antigen(s) by Monoclonal Antibodies" Cancer Research 1982 42:654-661.

Huang et al. "Inhibition of Skin Tumorigenesis by Rosemary and Its Constituents Carnosol and Ursolic Acid" Cancer Research 1994 54:701-708.

Huang et al. "Inhibitory Effects of Dietary Curcumin on Forestomach, Duodenal, and Colon Carcinogenesis in Mice" Cancer Research 1994 54:5841-5847.

Huang et al. "Structure of a WW Domain Containing Fragment of Dystrophin in Complex with β-Dystroglycan" Nature Structural and Molecular Biology 2000 7:634-638.

Hyer et al. "Synthetic Triterpenoids Cooperate with Tumor Necrosis Factor-Related Apoptosis-Inducing Ligand to Induce Apoptosis of Breast Cancer Cells" Cancer Research 2005 65:4799-4808.

Iguchi et al. "Lipid Peroxidation and Disintegration of the Cell Membrane Structure in Cultures of Rat Lung Fibroblasts Treated with Asbestos" Journal of Applied Toxicology 1993 13:269-275.

Ikeda et al. "Induction of Redox Imbalance and Apoptosis in Multiple Myeloma Cells by the Novel Triterpenoid 2-cyano-3,12-dioxoolean-1,9-dien-28-oic Acid" Molecular Cancer Therapeutics 2004 3:39-45.

Ikeda et al. "The Novel Triterpenoid CDDO and Its Derivatives Induce Apoptosis by Disruption of Intracellular Redox Balance" Cancer Research 2003 63:5551-5558.

Ishikawa et al. "Heme Oxygenase-1 Inhibits Antherogenesis in Watanabe Heritable Hyperlipidemic Rabbits" Circulation 2001 104(15):1813-1836.

Ito et al. "Involvement of Caspase-8 in the Induction of Osteosarcoma Cell Apoptosis by the Novel Triterpenoid CDDO" 47th Annual Meeting, Orthopaedic Research Society, Feb. 25-28, 2001, San Francisco, California, p. 0863, Poster Session, 2001.

Ito et al. "The Novel Triterpenoid 2-cyano-3, 12-dioxoolean-1,9-dien-28-oic Acid Induces Apoptosis of Human Myeloid Leukemia Cells by a Caspase-8-dependent Mechanism" Cell Growth & Differentiation 2000 11(5):261-267.

Ito et al. "The Novel Titerpenoid CDDO Induces Apoptosis and Differentiation of Human Osteosarcoma Cells by a Caspase-8 Dependent Mechanism" Molecular Pharmacology 2001 59:1094-1099.

Johansen et al. "Pharmacology and Preclinical Pharmacokinetics of the Triterpenoid CDDO Methyl Ester" Proceedings of the American Associate for Cancer Research 2003 44:1728.

Johnson et al. "A Plan for Distinguishing Between Some Five- and Six-Membered Ring Ketones" Journal of the American Chemical Society 1945 67:1745-1754.

Johnson et al. "Relationships Between Drug Activity in NCI Preclinical in vitro and in vivo Models and Early Clinical Trials" British Journal of Cancer 2001 84:1424-1431.

Joyce et al. "Integration of Rac-Dependent Regulation of Cyclin D1 Transcription Through a Nuclear Factor-KappaB-Dependent Pathway" Journal of Biological Chemistry 1999 275:25245-25249.

Kahne, D. and Collum, D. B. "Kinetic Cyanations of Ketone Enolates" Tetrahedron Letters 1981 22:5011-5014.

Kaltschmidt et al. "Transcription Factor NF-kappaB is Activated in Primary Neurons by Amyloid Beta Peptides and in Neurons Surrounding Early Plaques from Patients with Alzheimer Disease" Proceedings of the National Academy of Science USA 1997 94:2642-2647.

Karin, M. "Nuclear Factor-kappaB in Cancer Development and Progression" Nature 2006 441:431-436.

Kawamori et al. "Chemopreventive Activity of Celecoxib, As Specific Cyclooxygenase-2 Inhibitor, Against Colon Carcinogenesis" Cancer Research 1998 58(3):409-412.

Kerwin et al. "Quassinoid Synthesis. 2. Preparation of a Tetracyclic Intermediate Having the Bruceantin Tetrahydrofuran Ring" Journal of Organic Chemistry 1987 52:1686-1695.

Khan et al. "A Dichotomous Role for Nitric Oxide During Acute Toxoplasma Gondii Infection in Mice" Proceedings of the National Acadmey of Science USA 94:1997 13955-13960.

Kim et al. "Capasase-3 Activation is Involved in Apoptosis Induced by a Synthetic Triterpenoid in Non-Small Cell Lung Cancer (NSCLC) Cells" Proceedings of the American Association for Cancer Research 2000 41:770, Abstract #4894.

Kim et al. "Identification of a Novel Synthetic Triterpenoid, Mehty1-2-cyano-3,12-dioxooleana-1,9-dien-28-oate, That Potently Induces Caspase-Mediated Apoptosis in Human Lung Cancer Cells" Molecular Cancer Therapeutics 2002 1:177-184.

Kircher, H. W. "Triterpenes, in Organ Pipe Cactus" Phytochemistry 1980 19:2707-2712; Database CAPLUS on STN AN:1981:550946.

Konopleva, M. and Andreeff, M. "Regulatory Pathways in Programmed Cell Death" Cancer Molecular Biology 1999 6:1229-1260.

Konopleva et al. "Activation of Nuclear Transcription Factor PPARgamma by the Novel Triterpenoid CDDO as Targeted Therapy in Breast Cancer" 2002 Keystone Symposium, Abstract No. 539, 2002.

Konopleva et al. "Apoptosis Molecules and Mechanisms" Advances in Experimental Biology and Medicine 1998 457:217-236.

Konopleva et al. "Engraftment Potential of AML Progenitors into NOD/Scid Mice is Dependent on Baseline CXCR4 Expression" Blood 1999 94(Suppl 1):166b, Abstract #3916.

Konopleva et al. "Mechanisms and Activity of PPARgammaActive Triterpenoids CDDO and CDDO-Me in Leukemias" Blood 2005 106:2460.

Konopleva et al. "Novel Synthetic Triterpenoid CDDO-Me: Potent Antiproliferative, Proapoptotic and Differentiating Agent in AML" Blood 2000 96(11), Part 1:121A, Abstract #522.

Konopleva et al. "Novel Synthetic Triterpenoid, CDDO, and Its Methyl Ester: Potent Antiproliferative, Proapoptotic and Differentiating Agents in AML" Blood 1999 94(Suppl 1):479a, Abstract #2140.

Konopleva et al. "Novel Triterpenoid CDDO-Me is a Potent Inducer of Apoptosis and Differentiation in Acute Myelogenous Leukemia" Blood 2002 99(1):326-335.

(56) References Cited

OTHER PUBLICATIONS

Konopleva et al. "Peroxisome Proliferator-Activated Receptor Gamma and Retinoid X Receptor Ligands are Potent Inducers of Differentiation and Apoptosis in Leukemias" Molecular Cancer Therapeutics 2004 3:1249-1262.
Konopleva et al. "PPARγ Nuclear Receptor as a Novel Therapeutic Target in AML" Blood 2000 96(11):460a, Abstract #1982.
Konopleva et al. "PPARgamma Ligand CDDO Induces Apoptosis in Leukemias Via Multiple Apoptosis Pathways" Abstracts of the 44$^{th}$ Annual Meeting of the American Society of Hematology 2002 Abstract No. 2209.
Konopleva et al. "PPARgamma Ligands Are Potent Inducers of Apoptosis in Leukemias and Lymphomas" American Society of Hematology 43$^{rd}$ Annual Meeting and Exposition 2001 Abstract No. 501.
Konopleva et al. "PPARgamma Nuclear Receptor as a Novel Molecular Target in Leukemia Therapy" Proceedings of the American Association for Cancer Research 2002 43:4730.
Konopleva et al. "PPARgamma Nucelar Receptor as a Novel Therapeutic Target in AML" Proceedings of the American Association for Cancer Research 2001 42:4458.
Konopleva et al. "Suppresion of ERK Activation is Required for Triterpenoid Methyl-CDDO-Induced Apoptosis in AML" Blood 2003 102(11):1404.
Konopleva et al. "Synthetic Titerpenoid 2-cyano-3,12-dioxooleana-1,9-dien-28-oic Acid Induces Growth Arrest in HER2-Overexpressing Breast Cancer Cells" Molecular Cancer Therapy 2006 5:317-328.
Konopleva et al. "Synthetic Triterpenoid CDDO as a Novel Therapy for Resistant Breast Cancer" Proceedings of the American Association for Cancer Research 2003 44:2726.
Konopleva et al. "The Novel Triterpenoid CDDO-Me Suppresses MAPK Pathways and Promotes p38 Activation in Acute Myeloid Leukemia Cells" Leukemia 2005 19:1350-1354.
Konopleva et al. "The Synthetic Triterpenoid 2-cyano-3,12-dioxooleana-1,9-dien-28-oic Acid Induces Caspase-Dependent and -Independent Apoptosis in Acute Myelogenous Leukemia" Cancer Research 2004 64:7927-7935.
Konopleva et al. "Triterpenoid Methyl-CDDO Is a Potent Inducer of Apoptosis in CD34+ AML Progenitor Cells Via Activation of SAPK Pathways and Inhibition of MAPK Cascades" Blood 2004 104:2533.
Kornblau et al. "Apoptosis Regulating Proteins as Targets of Therapy for Hematological Malignancies" Expert Opinion on Investigational Drugs 1999 8:2027-2057.
Kornblau et al. "Phase I Study of Mitoxantrone Plus Etoposide with Multidrug Blockage by SDZ PSC-833 in Relapsed or Refractory Acute Myelogenous Leukemia" Journal of Clinical Oncology 1997 15(5):1796-1802.
Kowalski, C. J. and Reddy, R. E. "Ester Homologation Revisited: A Reliable, Higher Yielding and Better Understood Procedure" Journal or Organic Chemistry 1992 57:7194-7208.
Kress et al. "Triterpenoids Display Single Agent Activity in a Mouse Model of CLL/SBL" Blood 2006 108(11):2530.
Kress et al. "Triterpenoids Display Single Agent Anti-Tumor Activity in a Transgenic Mouse Model of Chronic Lymphocytic Leukemia and Small B Cell Lymphoma" PLoS One 2007 6(e559):1-11.
Kruger et al. "Up-Regulation of Heme Oxygenase Provides Vascular Protection in an Animal Model of Diabetes Through Its Antioxidant and Antiapoptotic Effects" Journal of Pharmacology and Experimental Therapeutics 2006 319:1144-1152.
Kurbacher et al. "Ascorbic Acid (Vitamin C) Improves the Antineoplastic Activity of Doxorubicin, Cisplatin, and Paclitaxel in Human Breast Carcinoma Cells in vitro" Cancer Letters 1996 103:183-189.
Kurinna et al. "The Novel Triterpenoid CDDO-Me Promotes Apoptosis in Gleevec-Resistant Chronic Myeloid Leukemia Cells by Caspase-Independent Mechanisms" Proceedings of the American Association for Cancer Research 2005 46:2240.
Langille et al. "Differential Effects of Physiological Concentrations of Retinoic Acid in vitro on Chondrogenesis and Myogenesis in Chick Craniofacial Mesenchyme" Differentiation 1989 40:84.
Lapillonne et al. "Activation of Peroxisome Proliferator-Activated Receptor Gamma by a Novel Synthetic Triterpenoid 2-cyano-3,12-dioxooleana-1,9-dien-28-oic Acid Induces Growth Arrest and Apoptosis in Breast Cancer Cells" Cancer Research 2003 63:5926-5939.
Lawson et al. "Isolation and Preliminary Characterization of Monoclonal Antibody That Interacts Preferentially with the Liver Isoenzyme of Human Alkaline Phosphatase" Clinical Chemistry 1985 31:381-385.
Lee et al. "Functional and Quantitative Analysis of Splenic T Cell Immune Responses Following Oral Toxoplasma Gondii Infection Mice" Experimental Parasitology 1999 91:212-221.
Lemieux, R. U. "Acylglycosyl Halides. [55] Tetra-O-acetyl-α-D-glucopyranosyl Bromide" Methods in Carbohydrate Chemistry 1963 2:221-222.
Liby et al. "The Synthetic Triterpenoids, CDDO and CDDO-Imidazolide, are Potent Inducers of Heme Oxygenase-1 and Nrf2/ARE Signaling" Cancer Research 2005 65:4789-4798.
Liby et al. "Triterpenoids and Rexinoids as Multifunctional Agents for the Prevention and Treatment of Cancer" Nature Reviews 7:357-369.
Lieu et al. "Dual Cytotoxic Mechanisms of Submicromolar Taxol on Human Leukemia HL-60 Cells" Biochemical Pharmacology 1997 53:1587-1596.
Ling et al. "The Novel Triterpenoid C-28 Methyl Ester of 2-Cyano-3, 12-dioxoolen-1,9-dien-28-oic Acid Inhibits Metastic Murine Breast Tumor Growth Through Inactivation of STAT3 Signaling" Cancer Research 2007 67:4210-4218.
Ling et al. "The Novel Triterpenoid CDDO-Me Inhibits Metastic Murine Breast Tumor Through Inhibition of Stat3 Signaling" 2007 AACR Annual Meeting, Abstract No. 301, 2007.
Liotta et al. "A Simple Method for the Efficient Synthesis of Unsaturated β-Dicarbonyl Compounds" Journal of Organic Chemistry 1981 46:2920-2923.
Liu et al. "Heme Oxygenase-1 (HO-1) Inhibits Postmyocardial Infarct Remodeling and Restores Ventricular Function" The FASEB Journal 2006 20(2):207-216.
Long et al. "Regulation of Human Bone Marrow-Derived Osteoprogenitor Cells by Osteogenic Growth Factors" Journal of Clinical Investigation 1995 95:881-887.
MacMicking et al. "Altered Responses to Bacterial Infection and Endotoxic Shock in Mice Lacking Inducible Nitric Oxide Synthase" 1995 Cell 81:641-650.
Marnett, L. J. "Asprin and the Potential Role of Prostaglandins in Colon Cancer" Cancer Research 1992 52(20):5575-5589.
McGeer, P. L. and McGeer, E. G. "The Inflammatory Response System of Brain: Implications for Therapy of Alzheimer and Other Neurodegenerative Diseases" Brain Research Reviews 1995 21:195-218.
Mehta et al. "Activation of Retinoid Receptors RAR Alpha and RXT Alpha Induces Differentiation and Apoptosis, Respectively, in HL-60 Cells" Cell Growth and Differentiation 1996 7(2):179-186.
Melichar et al. "Growth-Inhibitory Effect of a Novel Synthetic Triterpenoid, 2-cyano-3,12-dioxoolean-1,9-dien-28-oic Acid, on Ovarian Carcinoma Cell Lines Not Dependent on Peroxisome Proliferator—Activated Receptor—Gamma Expression" Gynecologic Oncology 2004 93:149-154.
Mella et al. "1,2-dideoxy-3, 4:5, 7-bis-o—(1-Methylethylidene)—D-gluco- and -D-galacto-hept-1-ynitols: Synthesis and Conformational Studies" Tetrahedron 1988 44:1673-1678.
Merril, J. E. and Benveniste, E. N. "Cytokines in Inflammatory Brain Lesions: Helpful and Harmful" Trends in Neurosciences 1996 19:331-338.
Minns et al. "A Novel Triterpenoid Induces Transforming Growth Factor Beta Production by Intraepithelial Lymphocytes to Prevent Ileitis" Gastroenterology 2004 127:119-126.
Mix et al. "A Synthetic Triterpenoid Selectively Inhibits the Induction of Matrix Metalloproteinases 1 and 13 by Inflammatory Cytokines" Arthritis and Rheumatism 2001 44:1096-1104.

(56) References Cited

OTHER PUBLICATIONS

Mix et al. "Peroxisome Proliferator-Activated Receptor-Gamma-Independent Repression of Collagenase Gene Expression by 2-cyano-3,12-dioxooleana-1,9-dien-28-oic Acid and Prostaglandin 15-deoxy-delta(12,14)J2: A Role for Smad Signaling" Molecular Pharmacology 2004 65:309-318.

Moncada et al. "Nitric Oxide: Physiology, Pathophysiology, and Pharmacology" Pharmacology Review 1991 43:109-142.

Morse, D. and Choi, A. M. K. "theme Oxygenase-1: From Bench to Bedside" American Journal of Respiratory and Critical Care Medicine 2005 172(6):660-670.

Murphy et al. "Immunomodulatory Effects of the Triterpenoid CDDO After Allogeneic Bone Marrow Transplantation in Mice: Reduction of Acute Graft-Versus-Host Disease Lethality" Blood 2005 106:1316.

Murray, R. E. And Zweifel, G. "Preparation of Phenyl Cyanate and Its Utilization for the Synthesis of α, β-Unsaturated Nitriles" Synthesis 1980 2:150-151.

Muzart, J. "Synthesis of Unsaturated Carbonyl Compounds via a Chromium-Mediated Allylic Oxidation by 70% Tert. butylhyrdoperoxide" Tetrahedron Letters 1987 28:4665-4668.

Nathan, C. And Xie, Q. "Nitric Oxide Synthases: Roles, Tolls and Controls" Cell 1994 78:915-918.

Nicholson et al. "Lethality of Endotoxin in Mice Genetically Deficient in the Respiratory Burst Oxidase, Inducible Nitric Oxide Synthase, or Both" Shock 1999 11:253-258.

Nishino et al. "Inhibition of the Tumor-Promoting Action of 12-O Tetradecanoylphorbol-13-acetate by Some Oleanane-Type Triterpenoid Compounds" Cancer Research 1988 48:5210-5212.

Ohshima, H. and Bartsch, H. "Chronic Infections and Inflammatory Process as Cancer Risk Factors: Possible Role of Nitric Oxide in Carinogenesis" Mutation Research 1994 305:253-264.

Omura, K. and Swern, D. "Oxidation of Alcohols by 'Activated' Dimethyl Sulfoxide. A Preparative Steric and Mechanistic Study" Tetrahedron 1978 34:1651-1660.

Ono et al. "A Convenient Procedure for Esterification of Carboxylic Acids" Bulletin of the Chemical Society of Japan 1978 51:2401-2404.

Oshima et al. "Suppression of Intestinal Polyposis in Apc$^{\Delta 716}$ Knockout Mice by Inhibition of Cyclooxygenase 2(COX-2)" Cell 1996 87:803-809.

Pahl, H. L. "Activators and Target Genes of Rel/NF-κB Transcription Factors" Oncogene 1999 18:6853-6866.

Palcy, S. and Goltzman, D. "Protein Kinase Signalling Pathways Involved in the Up-Regulation of the Rat Aplhal(I) Collagen Gene by Transforming Growth Factor Betal and Bone Morphogenetic Protein 2 in Osteoblastic Cells" Biochmemistry Journal 1999 343:21-27.

Paul et al. "Design and Synthesis of a Self-Assembled Photochemical Dyad Based on Selective Imidazole Recognition" Inorganic Chemistry 2002 41:3699-3704.

Paul et al. "Effective Expression of Small Interfering RNA in Human Cells" Nature Biotechnology 2002 20:505-508.

Pedersen et al. "The Triterpenoid CDDO Induces Apoptosis in Refactory CLL B Cells" Blood 2002 100:2965-2972.

Picard et al. "The Triterpene Reinols and Related Acids, Part VI" Journal of the Chemical Society 1939:1045-1048.

Place et al. "The Novel Synthetic Triterpenoid, CDDO-Imidazolide, Inhibits Inflammatory Response and Tumor Growth in vivo" Clinical Cancer Research 2003 9:2798-2806.

Prescott, S. M. and White, R. L. "Self-Promotion? Intimate Connections Between APC and Prostaglandin H Synthase-2" Cell 1996 87:783-786.

Rayet, B. and Gélinas, C. "Aberrant rel/nfkb Genes and Activity in Human Cancer" Oncogene 1999 18:6938-6947.

Reddy et al. "Evaluation of Cyclooxygenase-2 Inhibitor for Potential Chemopreventive Properties in Colon Carcinogenesis" Cancer Research 1996 56(20):4566-4569.

Rossi et al. "Anti-Inflammatory Cyclopentenone Prostaglandins are Direct Inhibitors of IkappaB Kinase" Nature 2000 403:103-108.

Ruvolo et al. "The Novel Triterpenoid Methyl-CDDO Inhibits Bc12 Phosphorylation and Potently Kolls U937 Cells" Blood 1999 94(10), Suppl. 1, Part 1:280A, Abstract #1251.

Sacerdoti et al. "Heme Oxygenase Overexpression Attenuates Glucose-Mediated Oxidative Stress in Quiescent Cell Phase: Linking Heme to Hyperglycemia Complications" Current Neurovascular Research 2005 2(2):103-111.

Salvemini et al. "Endogenous Nitric Oxide Enhances Prostaglandin Production in a Model of Renal Inflammation" Journal of Clinical Investigation 1994 93(5):1940-1947.

Salvemini et al. "Nitric Oxide Activates Cyclooxygenase Enzymes" Proceedings of the National Academy of Science USA 1993 90(15):7240-7244.

Samudio et al. "2,cyano-3,12 dioxoolean-1,9 diene-28-imidazolide Induces Apoptosis in Pancreatic Cancer via Redox-Dependent Cytoplasmic Stress" Proceedings of the American Association for Cancer Research 2005 46:5899.

Samudio et al. "2-Cyano-3,12-dioxooleana-1,9-dien-28-imidazolide (CDDO-Im) Directly Targets Mitochondrial Glutathione to Induce Apoptosis in Pancreatic Cancer" Journal of Biological Chemistry 2005 280:36273-36282.

Samudio et al. "A Novel Mechanism of Action of Methyl-2-cyano-3,12 dioxoolean-1,9 diene-28-oate: Direct Permeabiliztion of the Inner Mitochondrial Membrane to Inhibit Electron Transport and Induce Apoptosis" Molecular Pharmacology 2006 69:1182-1193.

Samudio et al. "A Novel Mechanism of Action of Methyl-2-cyano-3,12 dioxoolean-1,9 diene-28-oate (CDDO-Me) : Direct Permeablilization of the Inner Mitochondrial Membrane to Inhibit Electron Transport and Induce Apoptosis"Proceedings of the American Association for Cancer Research 2006 47:4693.

Samudio et al. "A Novel Mechanism of Action of Methyl-2-cyano-3,12 dioxoolean-1,9 diene-28-oate (CDDO-Me) : Direct Permeabilization of the Inner Mitochondrial Membrane to Inhibit Electron Transport and Induce Apoptosis" Blood 2005 106:4462.

Samudio et al. "The Novel Triterpenoid CDDOme Potently Synergizes with Inhibition of bcl-2 Function to Induce Apoptosis in AML via Disruption of Intracellular Redox Homeostasis" Proceedings of the American Association for Cancer Research 2005 46:4955.

Satoh et al. "Activation of the Keapl/Nrf2 Pathway for Neuroprotection by Electrophilic [Correction of Electrophillic] Phase II Inducers" Proceedings of the National Academy of Science USA 2006 103(3):768-773.

Scholz et al. "Sensitive and Specific Methods for the Determination of CDDO Methyl Ester in Mouse, Rat, Dog, Monkey, and Human Plasma by LC-Tandem Mass Spectrometry" Proceedings of the American Association of Cancer Research 2003 4:6321.

Seibert, K. and Masferrer, J. L. "Role of Inducible Cyclooxygenase(COX-2) in Inflammation" Receptor 1994 4(1):17-23.

Sharpless et al. "Electrophilic and Nucleophilic Oranoselenium Reagents. New Routes to Alpha, Beta-Unsaturated Carbonyl Compounds" Journal of the American Chemical Society 1973 95:6137.

Sheng et al. "A Selective Cyclooxygenase 2 Inhibitor Suppresses the Growth of H-ras-Transformed Rat Intestinal Epithelial Cells" Gastroenterology 1997 113(6):1883-1891.

Sheng et al. "Inhibition of Human Colon Cancer Cell Growth by Selective Inhibition of Cyclooxygenase-2" Journal of Clinical Investigation 1997 99(9):2254-2259.

Shishodia et al. "A Synthetic Triterpenoid, CDDO-Me, Inhibits IkappaBalpha Kinase and Enhances Apoptosis Induced by TNF and Chemotherapeutic Agents Through Down-Regulation of Expression of Nuclear Factor KappaB-Regulated Gene Products in Human Leukemic Cells" Clinical Cancer Research 2006 12:1828-1838.

Shull et al. "Identification of Vitamin D-Responsive Protein on the Surface of Human Osteosarcoma Cells" Proceedings of the National Academy of Science USA 1989 86:5405-5410.

Shull et al. "Morphologic and Biochemical Studies of Canine Mucopolysaccharidosis I" American Journal of Pathology 1984 114:487-495.

Simonian, N. A. And Coyle, J. T. "Oxidative Stress Neurodegenerative Diseases" Annual Review of Pharmacology and Toxicology 1996 36:83-106.

(56) References Cited

OTHER PUBLICATIONS

Simonsen et al. "Tetracyclic Hydroxy Acids" The Terpenes, Cambridge University, Cambridge 1957 5:221-285.
Singh et al. "Anti-Inflammatory Activity of Oleanolic Acid in Rats and Mice" Journal of Pharmacy and Pharmacology 1992 44:456-458.
Sive et al. "Expression of Chondrocyte Markers by Cells of Normal and Degenerate Intervertebral Discs" Molecular Pathology 2002 55:91-97.
Snitman et al. "Synthetic Approaches to Taxodione Synthesis of Methyl 12-oxopodocarpa-5,9(11)-diene-8β-carboxylate" Synthetic Communications 1978 8:187-194.
Sporn, M. B. and Roberts, A. B. "Peptide Growth Factors and Inflammation, Tissue Repair, and Cancer" Journal of Clinical Investigation 1986 78:329-332.
Sporn et al. "Prospects for Prevention and Treatment of Cancer with Selective PPARγ Modulators (SPARMs)" Trends in Molecular Medicine 2001 7(9):395-400.
Sporn et al. "Transforming Growth Factor-Beta: Biological Function and Chemical Structure" Science 1986 233:532-534.
Stadheim et al. "The Novel Triterpenoid 2-cyano-3,12-dioxooleana-1,9-dien-28-oic Acid (CDDO) Potently Enhances Apoptosis Induced by Tumor Necrosis Factor in Human Leukemia Cells" Journal of Biological Chemistry 2002 277:16448-16455.
Sterzycki, R. Z. "Pyridinium Tosylate, A Mild Catalyst for Formation and Cleavage of Dioxolane-Type Acetals" Synthesis 1979 724-725.
Stewart et al. "Risk of Alzheimer's Disease and Duration of NSAID Use" Neurology 1997 48:626-632.
Suh et al. "A Novel Synthetic Oleanane Triterpenoid, 2-cyano-3,12-dioxoolean-1,9-dien-28-oic Acid (CDDO), Induces Cell Differentiation in Human Myeloid Leukemias" Proceedings of the American Association for Cancer Research Annual Meeting 1999 40:300, Abstract #1988.
Suh et al. "A Novel Synthetic Oleanane Triterpenoid, 2-cyano-3,12-dioxoolen-1,9-dien-28-oic Acid, With Potent Differentiating, Antiproliferative, and Anti-Inflmmatory Activity" Cancer Research 1999 59(2):336-341.
Suh et al. "Novel Triterpenoids Suppress Inducible Nitric Oxide Synthase (iNOS) and Inducible Cyclooxygenase (COX-2) in Mouse Macrophages" Cancer Research 1998 58:717-723.
Suh et al. "Novel Triterpenoids Suppress Inducible Nitric Oxide Synthase (iNOS) and Inducible Cyclooxygenase (COX-2)" Proceedings of the American Association for Cancer Research Annual Meeting 1998 39:266.
Suh et al. "Synthetic Triterpenoids Activate a Pathway for Apoptosis in AML Cells Involving Downregulation of Flip and Sensitization to Trail" Leukemia 2003 17:2122-2129.
Suh et al. "Synthetic Triterpenoids Enhance Transforming Growth Factor β/Smad Signaling" Cancer Research 2003 63:1371-1376.
Suh et al. "Triterpenoids CDDO and CDDO-Me Down-Regulate FLIP Expression and Sensitize AML Cells to Trail-Induced Apoptosis" American Society of Hematology 43rd Annual Meeting and Exposition 2001 Abstract No. 498.
Sun et al. "The Synthetic Trierpenoid, CDDO, Suppresses Alloreactive T Cell Responses and Reduces Murine Early Acute Graft-Versus-Host Disease Mortaility" Biology of Blood and Marrow Transplantation 2007 13:521-529.
Syftestad et al. "The in vitro Chondrogenic Response of Limb-Bud Mesenchyme to a Water-Soluble Fraction Prepared from Demineralized Bone Matrix" Differentiation 1985 29:230.
Tabe et al. "Chromatin-Mediated Transctional Activation with Novel Peroxisome Proliferator-Activated Receptor gamma(PPARgamma) Ligand 2-cyano-1,9-dien-28-oic Acid (CDDO) in Acute Promyelocytic Leukemia Cells" Abstracts of the 44th Annual Meeting of the American Society of Hematology 2002 Abstract No. 2191.
Takabe et al. "Synthesis of Lycosyl Esters of Oleanolic" Carbohydrate Research 1979 76:101-108, Database CAPLUS on STN an:1980:42278.

Takahashi et al. "Increased Expression of Inducible and Endothelial Constitutive Nitric Oxide Synthases in Rat Colon Tumors Induced by Azoxymethane" Cancer Research 1997 57:1233-1237.
Tamir, S. and Tannebaum, S. R. "The Role of Nitric Oxide (NO) in the Carcinogenic Process" Biochimic and Biophysica Acta 1996 1288:F31-F36.
Tamm et al. "Expression and Prognostic Significance of IAP-Family Genes in Human Cancers and Leukemia" Blood 1999 94(Suppl. 1):69a, Abstract #298.
Tenenbaum, H. C. and Heersche, J. N. M. "Differentiation of Osteoblasts and Formation of Mineralized Bone in vitro" Calcified Tissue International 1982 34:76.
Toriumi et al. "Mandibular Reconstruction with a Recombinant Bone-Inducing Factor. Functional, Histologic, and Biomechanical Evaluation" Archives Otolaryngology Head and Neck Surgery 1991 117:1101-1112.
Tsai et al. "Monoclonal Antibody to Human Osteosarcoma: A Novel Mr 26,000 Protein Recognized by Murine Hybridoma TMMR-2" Cancer Research 1990 50:152-161.
Tsao et al. "DRIP205 Co-Activator Overexpression Enhances PPARgamma-Mediated Differentiation of Leukemia Cells by CDDO" Proceedings of the American Association for Cancer Research 2005 46:1855.
Tsao et al. "Targeted Induction of Apoptosis in Leukemia by PPARgamma Ligation" American Society of Hematology 43rd Annual Meeting and Exposition 2001 Abstract No. 2381.
Tsujii, M. and DuBois, R. N. "Alterations in Cellular Adhesion and Apoptosis in Epithelial Cells Overexpressing Prosaglandin Endoperoxide Synthase 2" Cell 1995 83:493-501.
Tsujii et al. "Cyclooxygenases Regulates Angiogenesis Induced by Colon Cancer Cells" Cell 1998 93:705-716.
Turksen et al. "Isolation of Monoclona Antibodies Recognizing Rat Bone-Associated Molecules in vitro and in vivo" Journal of Histochemistry and Cytochemistry 1992 40:1339-1352.
Vazquez et al. "Human Immunodeficiency Virus Type 1-Induced Macrophage Gene Expression Includes the p21 Gene, a Target for Viral Regulation" Journal of Virology 2005 79:4479-4491.
Vukicevic et al. "Stimulation of the Expression of Osteogenic and Chondrogenic Phenotypes in vitro by Osteogenin" Proceedings of the National Academy of Science USA 1989 86:8793-8797.
Walczak et al. "Tumoricidal Activity of Tumor Necrosis Factor-Related Apoptosis-Including Ligand in vivo" Naure Medicine 1999 5(2):157-163.
Walsh et al. "Monoclonal Antibodies with Selective Reactivity Against Osteoblasts and Osteocytes in Human Bone" Journal of Bone and Mineral Research 1994 9:1687-1696.
Wang et al. "A Novel Synthetic Triterpenoid, 2-cyano-3,12-dioxoolean-1,9-dien-28-oic Acid (CDDO) Induces Adipocyte Differentiation in 3T3-L1 Cells" Proceedings of the American Association for Cancer Research Annual Meeting 1999 40:300, Abstract #1989.
Wang et al. "A Synthetic Triterpenoid, 2-cyano-3,12-dioxooleana-1,9-dien-28-oic Acid (CDDO), Is a Ligand for the Peroxisome Proliferator-activated Receptor γ" Molecular Endocrinology 2000 14:1550-1556.
Warrell et al. "Differentiation Therapy of Acute Promyelocytic Leukemia with Tretinoin (All-Trans-Retinoic Acid)" New England Journal of Medicine 1991 324(20):1385-1393.
Williams et al. "Immunology of Multiple Sclerosis" Journal of Clinical Neuroscience 1994 2(3-4):229-245.
Woodley, J. F. "Liposomes for Oral Administration of Drugs" Critical Reviews in Therapeutic Drug Carrier System 1985 2(1):1-18.
Xie et al. "Differential Expression Patterns in Human Myeloblastic Leukemia HL-60 and Multidrug Resistant HL-60/Dox Cells Analyzed by Human cDNA Expression Array" Blood 1998 92(Suppl 1):387a, Abstract #1600.
Yates et al. "Pharmacodynamic Characterization of Chemopreventive Triterpenoids as Exceptionally Potent Inducers of Nrf2-Regulated Genes" Molecular Cancer Therapeutics 2007 6:154-162.
Yates et al. "Potent Protection Against Aflatoxin-Induced Tumorigenesis Through Induction of Nrf2-Regulated Pathways by

(56) References Cited

OTHER PUBLICATIONS the Triterpenoid 1-[2-cyano-3-,12-dioxooleana-1,9(11)-dien-28-oyl]imidazole" Cancer Research 2006 66:2488-2494.

Yue et al. "Depletion of Intracellular Glutathione Contributes to JNK-Mediated Death Receptor 5 Upregulation and Apoptosis Induction by the Novel Synthetic Triterpenoid Methyl-2-cyano-3,12-dioxooleana-1,9-dien-28-oate (CDDO-Me)" Cancer & Biology Therapy 2006 5(5) :492-497.

Zapata et al. "CDDO and CDDO-Im Reduce Tumor Burden in a Transgenic Mouse Model of CLL" Blood 2004 104:3477.

Zapata et al. "Triterpenoids Show Activity Against Leukemic Cells in a Transgenic Mouse Model of CLL" Proceedings of the American Association for Cancer Research 2005 46:5179.

Zhang et al. "Synthetic Triterpenoid CDDO as Effective Therapy for HER2-Expressing Resistant Breast Cancer" Proceedings of the American Association for Cancer 2004 Abstract No. 3799.

Zhang et al. "The Novel Synthetic Oleanane Triterpenoid CDDO (2-cyano-3, 12-dioxoolean-1,9-dien-28-oic Acid) Induces Apoptosis in Mycosis Fungoides/Sézary Syndrome Cells" Journal of Investigative Dermatology 2004 123:380-387.

Zhou et al. "Carbon Monoxide Suppresses Bleomycin-Induced Lung Fibrosis" American Journal of Pathology 2005 166(1):27-37.

Zou et al. "c-Jun NH2-Terminal Kinase-Mediated Up-Regulation of Death Receptor 5 Contributes to Induction of Apoptosis by the Novel Synthetic Triterpenoid Methyl-2-cyano-3,12-dioxooleana-1,9-dien-28-oate in Human Lung Cancer Cells" Cancer Research 2004 64:7570-7578.

Office Communication dated Mar. 9, 2009 from U.S. Appl. No. 11/941,723, filed Nov. 16, 2007.

"CDDO in Treating Patients with Metastatic or Unresectable Solid Tumors or Lymphoma" http://www.clincialtrials.gov/ct2/show/NCT00352040?term=CDDO&rank=1, Dec. 14, 2008.

"FDA Mulls Drug to Slow Late-Stage Alzheimer's" http://www.cnn.com/2003/HEALTH/conditions/09/24/alzheimers.drug.ap/index.html, Retrieved on Sep. 23, 2003.

"Phase IIa Trail to Determine the Effects of Bardoxolone Methyl on Renal Function in Patients with Diabetic Nephropathy" http://www.clincialtrails.gov/ct2/show/NCT00664027?term=rta&rank=10, Dec. 14, 2008.

"RTA 402 in Advanced Solid Tumors or Lymphoid Malignancies" http://www.clinicaltrials.gov/ct2/show/NCT00508807?term=rta&rank=2&show_desc=Y, Dec. 14, 2008.

"Study to Assess the Safety, Tolerability, and Pharmacodynmics of RTA 402 in Patients with Hepatic Dysfunction" http://www.clinicaltrials.gov/ct2/show/NCT00550849?term=rta&rank=4, Dec. 14, 2008.

Akrivakis et al. "Prolonged Infusion of Gemcitabine in Stage IV Breast Cancer: A Phase I Study" Anti-Cancer Drugs 1999 10(6):525-531.

Alexander et al. "Synthesis and Cytotoxic Activity of Two Novel 1-dodecylthio-2-decyloxypropyl-3-phosphatidic Acid Conjugates with Gemcitabine and Cytosine Arabinoside" Journal of Medicinal Chemistry 2003 46(19):4205-4208.

Ardestani et al. "Effects of Dexamethasone and Betamethasone as COX-2 Gene Expression Inhibitors on Rigidty in a Rat Model of Parkinson's Disease" Indian Journal of Pharmacology 2007 39:235-239.

Ariga et al. "Role of Sphingolipid-Mediated Cell Death in Neurodegeneratvie Diseases" Journal of Lipid Research 1998 39:1-16.

Baker et al. "2'-Deoxy-2'-methylenecytidine and 2'-deoxy-2',2'-diflurocytidine 5'-diphosphates: Potent Mechanism-Based Inhibitors of Ribonucleotide Reductase" Journal of Medicinal Chemistry 1991 34(6):1884.

Balkwill et al. "Smoldering and Polarized Inflammation in the Initiation and Promotion of Malignant Disease" Cancer Cell 2005 7(3):211-217.

Cerwenka, A. and Swain, S. L. "TGF-β1: Immunosuppressant and Viability Factor for T Lymphocytes" Microbes and Infection 1999 1:1291-1296.

Cho et al. "The Transcription Factor NRF2 Protects Against Pulmonary Fibrosis" FASEB Journal 2004 18:1-29.

Chou et al. "Stereospecific Synthesis of 2-Deoxy-2,2-difluororibonolactone and Its Use in the Preparation of 2'-deoxy-2',2'-difluoro-B—D-ribofuranosyl Pyrimidine Nucleosides: The Key Role of Selective Crystallization" Synthesis 1992 565-570.

Cianchi et al. "Cyclooxygenase-2 Activation Mediates the Proangiogenic Effect of Nitric Oxide in Colorectal Cancer" Clinical Cancer Research 2004 10:2694-2704.

Cripe, L. D. "Adult Acute Leukemia" Current Problems in Cancer 1997 21(1):4-64.

Cui, Y. "A Material Science Perspective of Pharmaceutical Solids" International Journal of Pharmaceutics 2007 339(1-2):3-18.

Di Stefano et al. "Inhibition of [3H]thymidine Incorporation into DNA of Rat Regenerating Liver by 2',2'-difluorodeoxycytidine Coupled to Lactosaminated poly-L-lysine" Biochemical Pharmacology 1999 57(7):793-799.

Ekmekcioglu et al. "Tumor iNOS Predicts Poor Survival for Stage III Melanoma Patients" International Journal of Cancer 2006 119:861-866.

Ellies et al. "Mammary Tumor Latency is Increased in Mice Lacking the Inducible Nitric Oxide Synthase" International Journal of Cancer 2003 106:1-7.

Gandhi et al. "Prolonged Infusion of Gemcitabine: Clinical and Pharmacodynamics Studies During a Phase I Trial in Relapsed Acute Myelogenous Leukemia" Journal of Clinical Oncology 2002 20(3):665-673.

Godoy et al. "Central and Systemic IL-I Exacerbates Neurodegeneration and Motor Symptoms in a Model of Parkinson's Disease" Brain 2008 131:1880-1894.

Guo et al. "Selective Protection of 2',2'-Diflurodeoxycytidine (Gemcitabine)" Journal of Organic Chemistry 1999 64:8319-8322.

Guo et al. "Targeted Delivery of a Peripheral Benzodiazepine Receptor Ligand-Gemcitabine Conjugate to Brain Tumors in a Xenograft Model" Cancer Chemotherapy and Pharmacology 2001 48(2):169-176.

Honda et al. "Design, Synthesis, and Biological Evaluation of Biotin Conjugates of 2-cyano-3,12-dioxooleana-1,9(11)-dien-28-oic Acid for the Isolation of the Protein Targets" Journal of Medicinal Chemistry 2004 47(20):4923-4932.

Hong et al. "Phase I Trial of a Novel Oral NF-κB/pSTAT3 Inhibitor RTA-402 in Patients with Solid Tumors and Lymphoid Malignancies" 44th Annual Meeting of the American Society of Clinical Oncology, 2008.

Kasinski et al. "Inhibition of IkappaB Kinase-Nuclear Factor-kappaB Signaling Pathway by 3,5-bis(2-flurobenzylidene)piperidin-4-one (EF24), A Novel Monoketone Analog of Curcumin" Molecular Pharmacology 2008 74(3) : 654-661.

Klotz et al. "Selective Expression of Inducible Nitric Oxide Synthase in Human Prostate Carcinoma" Cancer 1998 82:1897-1903.

Lala et al. "Role of Nitric Oxide in Tumor Progression: Lessons from Experimental Tumors" Cancer and Metastasis Reviews 1998 17(1):91-106.

Leonard et al. "Expression of Nitric Oxide Synthase in Inflammatory Bowel Disease is Not Affected by Corticosteriod Treatment" Journal of Clinical Pathology 1998 51:750-753.

Li, N. and Nel, A. E. "Role of the Nrf2-Mediated Signaling Pathway as a Negative Regulator of Inflammation: Implications for the Impact of Particulate Pollutants on Asthma" Antioxidants & Redox Signaling 2006 8:89-98.

Liby et al. "A Novel Acetylenic Tricyclic bis-(cyano enone) Potently Induces Phase 2 Cytoprotective Pathways and Blocks Liver Carcinogenesis Induced by Aflatoxin" Cancer Research 2008 68:6727-6733.

Liby et al. "The Rexinoid LG100268 and the Synthetic Triterpenoid CDDO-Methyl Amide are More Potent than Erlotinib for Prevention of Mouse Lung Carcinogenesis" Molecular Cancer Therapy 2008 7:1251-1257.

Luo et al. "IKK/NF-kappaB Signaling: Balancing Life and Death—A New Approach to Cancer Therapy" Journal of Clinical Investigation 2005 115(10):2625-2631.

(56) References Cited

OTHER PUBLICATIONS

Mantovani, A. "Inflammation by Remote Control" Nature 2005 435:752-753.
Marrogi et al. "Nitric Oxide Synthase, Cyclooxygenase 2 and Vascular Endothelial Growth Factor in the Angiogenesis of Non-Small Cell Lung Carcinoma" Clinical Cancer Research 2000 6:4739-4744.
Maurel et al. "Phase I Trial of Weekly Gemcitabine at 3-h Infusion in Refractory, Heavily Pretreated Advanced Solid Tumors" Anti-Cancer Drugs 2001 12(9):713-717.
Morris et al. "Association of a Functional Inducible Nitric Oxide Xynthase Promoter Variant with Complications in Type 2 Diabetes" Journal of Molecular Medicine 2002 80(2):96-104.
Morse, D. and Choi, A. M. "Heme Oxygenase-1: the 'Emerging Molecule' Has Arrived" American Journal of Respiratory and Critical Care Medicine 2002 27(1):8-16.
Na, H. and Surh, Y. "Transcriptional Regulation via Cysteine Thiol Modification: A Novel Molecular Strategy for Chemoprevention and Cytoprotection" Molecular Carcinogenesis 2006 45(6):360-380.
Nathan et al. "Protection from Alzheimer's-like Disease in the Mouse by Genetic Ablation of Inducible Nitric Oxide Synthase" The Journal of Experimental Medicine 2005 202:1163-1169.
Nathan, C. "Points of Control in Inflammation" Nature 2002 420:846-852.
Office Action in Canadian Patent App. No. 2,335,505, mailed Jan. 10, 2008.
Office Action in Canadian Patent App. No. 2,335,505, mailed Nov. 23, 2006.
Office Action in Canadian Patent App. No. 2,335,505, mailed Sep. 22, 2008.
Office Action in Canadian Patent App. No. 2,430,454, mailed Jan. 20, 2009.
Office Action in European Patent App. No. 01 989 130, mailed Jul. 31, 2008.
Office Action, in European Patent App. No. 03 729 681, mailed Nov. 6, 2008.
Office Action in European Patent App. No. 99 928 731, mailed Aug. 1, 2008.
Office Action in European Patent App. No. 99 928 731, mailed Dec. 9, 2008.
Office Action in European Patent App. No. 99 928 731, mailed Dec. 15, 2004.
Office Action in European Patent App. No. 99 928 731, mailed Feb. 14, 2007.
Office Action in U.S. Appl. No. 09/335,003, mailed Aug. 28, 2000.
Office Action in U.S. Appl. No. 09/335,003, mailed Mar. 15, 2001.
Office Action in U.S. Appl. No. 09/335,003, mailed Nov. 2, 2000.
Office Action in U.S. Appl. No. 09/927,081, mailed Feb. 22, 2002.
Office Action in U.S. Appl. No. 09/998,009, mailed Apr. 4, 2007.
Office Action in U.S. Appl. No. 09/998,009, mailed Jul. 11, 2005.
Office Action in U.S. Appl. No. 09/998,009, mailed Jul. 14, 2004.
Office Action in U.S. Appl. No. 09/998,009, mailed Jul. 3, 2006.
Office Action in U.S. Appl. No. 09/998,009, mailed Mar. 24, 2004.
Office Action in U.S. Appl. No. 09/998,009, mailed Nov. 30, 2005.
Office Action in U.S. Appl. No. 09/998,009, mailed Nov. 16, 2007.
Office Action in U.S. Appl. No. 09/998,009, mailed Oct. 20, 2004.
Office Action in U.S. Appl. No. 10/345,053, mailed Aug. 25, 2004.
Office Action in U.S. Appl. No. 10/345,053, mailed Dec. 23, 2004.
Office Action in U.S. Appl. No. 10/345,053, mailed Dec. 6, 2005.
Office Action in U.S. Appl. No. 10/345,053, mailed Mar. 1, 2006.
Office Action in U.S. Appl. No. 10/345,053, mailed May 31, 2005.
Office Action in U.S. Appl. No. 10/395,372, mailed Apr. 28, 2006.
Office Action in U.S. Appl. No. 10/395,372, mailed Aug. 4, 2005.
Office Action in U.S. Appl. No. 10/395,372, mailed Dec. 20, 2006.
Office Action in U.S. Appl. No. 10/395,372, mailed Feb. 7, 2007.
Office Action in U.S. Appl. No. 10/395,372, mailed Jan. 28, 2004.
Office Action in U.S. Appl. No. 10/395,372, mailed Jul. 9, 2004.
Office Action in U.S. Appl. No. 10/395,372, mailed Jun. 12, 2006.
Office Action in U.S. Appl. No. 10/395,372, mailed May 23, 2005.
Office Action in U.S. Appl. No. 10/395,372, mailed Nov. 23, 2005.
Office Action in U.S. Appl. No. 10/435,925, mailed Sep. 30, 2004.
Office Action in U.S. Appl. No. 11/121,316, mailed Apr. 16, 2009.
Office Action in U.S. Appl. No. 11/121,316, mailed Jul. 21, 2008.
Office Action in U.S. Appl. No. 11/121,316, mailed Mar. 17, 2008.
Office Action in U.S. Appl. No. 11/672,449, mailed Jun. 13, 2008.
Office Action in U.S. Appl. No. 11/672,449, mailed Mar. 20, 2009.
Office Action in U.S. Appl. No. 11/927,418, mailed Mar. 2, 2009.
Office Action in U.S. Appl. No. 11/941,820, mailed Apr. 21, 2009.
Osburn et al. "Genetic of Pharmacologic Amplification of Nrf2 Signaling Inhibits Acute Inflammatory Liver Injury in Mice" Toxicological Sciences 2008 104:218-227.
Patel et al. "Phase II Clinical Investigation of Gemcitabine in Advanced Soft Tissue Sarcomas and Window Evaluation of Dose Rate on Gemcitabine Triphosphate Accumulation" Journal Clinical Oncology 2001 19(15):3483-3489.
PCT, International Preliminary Examination Report, in Int. App. No. PCT/US1999/13635 mailed Sep. 6, 2000.
PCT, International Preliminary Examination Report, in Int. App. No. PCT/US2001/44541 mailed Jan. 15, 2004.
PCT, International Preliminary Examination Report, in Int. App. No. PCT/US2003/01307 mailed Oct. 20, 2003.
PCT, International Search Report and Written Opinion, in Int. App. No. PCT/US2008/073352 mailed Feb. 13, 2009.
PCT, International Search Report and Witten Opinion, in Int. App. No. PCT/US2007/085010 mailed Apr. 16, 2008.
PCT, International Search Report and Written Opinion, in Int. App. No. PCT/US2009/030771 mailed Apr. 9, 2009.
PCT, International Search Report and Written Opinion, in Int. App. No. PCT/US2007/071933 mailed Nov. 26, 2007.
PCT, International Search Report and Written Opinion, in Int. App. No. PCT/US2007/085010 mailed Apr. 16, 2008.
PCT, International Search Report, in Int. App. No. PCT/US1999/13635 mailed Oct. 20, 1999.
PCT, International Search Report, in Int. App. No. PCT/US2001/44541 mailed Jan. 24, 2003.
PCT, International Search Report, in Int. App. No. PCT/US2003/01037 mailed May 12, 2003.
PCT, Written Opinion, in Int. App. No. PCT/US1999/13635 mailed May 15, 2000.
PCT, Written Opinion, in Int. App. No. PCT/US2001/44541 mailed Sep. 23, 2003.
Petition Decision, issued in U.S. Appl. No. 10/345,053, mailed May 22, 2006.
Pollard, J. W. "Tumor-Educated Marcophages Promote Tumor Progression and Metatasis" Nature Reviews 2004 4:71-78.
Rangasamy et al. "Disruption of Nrf2 Enhances Susceptibility to Severe Airway Inflammation and Asthma in Mice" Journal of Experimental Medicine 2005 202:47-59.
Response to Office Action, in Canadian Patent App. No. 2,335,505, dated Jul. 10, 2008.
Response to Office Action, in Canadian Patent App. No. 2,335,505, dated May 11, 2007.
Response to Office Action, in European Patent App. No. 01 989 130, dated Sep. 5, 2008.
Response to Office Action, in European Patent App. No. 99 928 731, dated Oct. 1, 2008.
Response to Office Action, in European Patent App. No. 99 928 731, dated Mar. 9, 2009.
Response to Office Action, in European Patent App. No. 99 928 731, dated Jun. 23, 2005.
Response to Office Action, in European Patent App. No. 99 928 731, dated Aug. 14, 2007.
Response to Office Action, in U.S. Appl. No. 09/335,003, dated Sep. 28, 2000.
Response to Office Action, in U.S. Appl. No. 09/335,003, dated Mar. 2, 2001.
Response to Office Action, in U.S. Appl. No. 09/335,003, dated Apr. 16, 2001.
Response to Office Action, in U.S. Appl. No. 09/927,081, dated Jun. 24, 2002.
Response to Office Action, in U.S. Appl. No. 09/998,009, dated Apr. 21, 2004.

(56) References Cited

OTHER PUBLICATIONS

Response to Office Action, in U.S. Appl. No. 09/998,009, dated Sep. 14, 2004.
Response to Office Action, in U.S. Appl. No. 09/998,009, dated Apr. 19, 2005.
Response to Office Action, in U.S. Appl. No. 09/998,009, dated Oct. 11, 2005.
Response to Office Action, in U.S. Appl. No. 09/998,009, dated Mar. 30, 2006.
Response to Office Action, in U.S. Appl. No. 09/998,009, dated Jan. 3, 2007.
Response to Office Action, in U.S. Appl. No. 09/998,009, dated Sep. 4, 2007.
Response to Office Action, in U.S. Appl. No. 09/998,009, dated Feb. 18, 2008.
Response to Office Action, in U.S. Appl. No. 10/345,053, dated Sep. 24, 2004.
Response to Office Action, in U.S. Appl. No. 10/345,053, dated Mar. 23, 2005.
Response to Office Action, in U.S. Appl. No. 10/345,053, dated Sep. 3, 2005.
Response to Office Action, in U.S. Appl. No. 10/345,053, dated Feb. 6, 2006.
Response to Office Action, in U.S. Appl. No. 10/395,372, dated Apr. 28, 2004.
Response to Office Action, in U.S. Appl. No. 10/395,372, dated Nov. 9, 2004.
Response to Office Action, in U.S. Appl. No. 10/395,372, dated Jul. 25, 2005.
Response to Office Action, in U.S. Appl. No. 10/395,372, dated Nov. 23, 2005.
Response to Office Action, in U.S. Appl. No. 10/395,372, dated Apr. 21, 2006.
Response to Office Action, in U.S. Appl. No. 10/395,372, dated Oct. 12, 2006.
Response to Office Action, in U.S. Appl. No. 10/395,372, dated Jan. 12, 2007.
Response to Office Action, in U.S. Appl. No. 10/395,372, dated Feb. 14, 2007.
Response to Office Action, in U.S. Appl. No. 10/435,925, dated Mar. 30, 2005.
Response to Office Action, in U.S. Appl. No. 11/121,316, dated Apr. 4, 2008.
Response to Office Action, in U.S. Appl. No. 11/121,316, dated Dec. 19, 2008.
Response to Office Action, in U.S. Appl. No. 11/672,449, dated Dec. 15, 2008.
Response to Office Action, in U.S. Appl. No. 11/927,418, dated Apr. 2, 2009.
Response to Written Opinion, in Int. App. No. PCT/US1999/13635, dated Jul. 14, 2000.
Richardson et al. "Synthesis and Restriction Enzyme Analysis of Oligodeoxyribonucleotides Containing the Anti-Cancer Drug 2',2'-diofluoro-2'-deoxycytidine" Nucleic Acid Research 1992 20(7):1763-1769.
Rizzieri et al. "Phase I Evaluation of Prolonged-Infusion Gemcitabine with Mitoxantrone for Relapsed or Refractory Acute Leukemia" Journal of Clinical Oncology 2002 20(3):674-679.
Robbins et al. "Inflammation and Repair" Basic Pathology 3$^{rd}$ Edition, W.B. Sanders Company, Chapter 2, p. 28, 1981.
Singh, S. and Evans, T. W. "Nitric Oxide, the Biological Mediator of the Decade: Fact or Fiction?" European Respiratory Journal 1997 10:699-707.
Stedman's Medical Journal 23$^{rd}$ Edition, The Williams & Wilkins Company, p. 401, 1976.
Strejan et al. "Suppression of Chronic-Relapsing Experimental Allergic Encephalomyelitis in Strain-13 Guinea Pigs by Administration of Liposome-Associated Myelin Basic Protein" Journal of Neuroimmunology 1984 7(1):27.
Suh et al. "New Triterpenoids as Cancer Preventive and Anti-inflammatory Agents" Proceedings of the American Association for Cancer Research 1997 38:216, Abstract No. 1457.
Supplementary European Search Report, issued in European Patent App. No. 01 989 130, mailed Aug. 9, 2007.
Supplementary European Search Report, issued in European Patent App. No. 03 729 681, mailed Aug. 3, 2006.
Sussan et al. "Disruption of Nrf2, a Key Inducer of Antioxidant Defenses, Attenuates ApoE-Mediated Atherosclerosis in Mice" PLoS One 2008 3(11):1-9.
Temper() et al. "Randomized Phase II Comparison of Dose-Intense Gemcitabine: Thirty-Minute Infusion and Fixed Dose Rate Infusion in Patients with Pancreatic Adenocarcinoma" Journal of Clinical Oncology 2003 21(18):3402-3408.
Therasse et al. "New Guidelines to Evaluate the Response to Treatment in Solid Tumors. European Organization for Research and Treatment of Cancer, National Cancer Institute of the United States, National Cancer Institute of Canada" Journal of the National Cancer Institute 2000 92(3):205.
Thimmulappa et al. "Nrf2 is a Critical Regulator of the Innate Immune Response and Survival During Experimental Sepsis" Journal of Clinical Investigation 2006 116(4):984-995.
Thimmulappa et al. "Nrf2-Dependent Protection from LPS Induced Inflammatory Response and Mortality by CDDO-Imidazolide" Biochemical and Biophysical Research Communications 2006 351:883-889.
Thimmulappa et al. "Preclinical Evaluation of Targeting the Nrf2 Pathway by Triterpenoids (CDDO-Im and CDDO-Me) for Protection from LPS-Induced Inflammatory Response and Reactive Oxygen Species in Human Peripheral Blood Mononuclear Cells and Neutrophils" Antioxidants & Redox Signaling 2007 9:1-8.
Torres et al. "Inflammation and Nitric Oxide Production in Skeletal Muscle of Type 2 Diabetic Patients" Journal of Endocrinology 2004 181:419-427.
Tran et al. "The Synthetic Triterpenoid CDDO-Methyl Ester Modulates Microglial Activities Inhibits TNF Production, and Provides Dopaminergic Neuroprotection" Journal of Neuroinflammation 2008 5:1-14.
U.S. Appl. No. 12/352,473, filed Jan. 12, 2009.
U.S. Appl. No. 12/426,737, filed Apr. 20, 2009.
U.S. Appl. No. 12/426,778, filed Apr. 20, 2009.
U.S. Appl. No. 12/426,791, filed Apr. 20, 2009.
U.S. Appl. No. 12/426,832, filed Apr. 20, 2009.
U.S. Appl. No. 12/426,889, filed Apr. 20, 2009.
U.S. Appl. No. 60/955,939, filed Aug. 15, 2007.
Van Muiswinkel, F. L. and Kuiperij, H. B. "The Nrf2-ARE Signaling Pathway: Promising Drug Target to Combat Oxidative Stress in Neurodegenerative Disorders" Current Drug Target—CNS & Neurological Disorders 2005 4:267-281.
Veerman et al. "Antitumor Activity of Prolonged as Compared with Bolus Administration of 2',2'-difluorodeoxycytidine in vivo Against Murine Colon Tumors" Cancer Chemotherapy and Pharmacology 1996 38(4):335-342.
Vodovotz et al. "Inducible Nitric Oxide Synthase in Tangle-Bearing Neurons of Patients with Alzheimer's Disease" The Journal of Experimental Medicine 1996 184:1425-1433.
Yore et al. "The Synthetic Triterpenoid 1-[2-cyano-3,12-dioxooleana-1,9(11)-dien-28-oyl]imidazole Blocks Nuclear Factor-kappaB Activation through Direct Inhibition of IkappaB Kinase Beta" Molecular Cancer Therapy 2006 5(12):3232-3239.
Yu, X. and Kensler, T. "Nrf2 as a Target for Cancer Chemoprevention" Mutation Research 2005 591(1-2):93-102.
Office Communication dated Dec. 23, 2009 from U.S. Appl. No. 11/941,723, filed Nov. 16, 2007.
Ji et al. "The Synthetic Triterpenoid CDDO-Imidazolide Induces Monocytic Differentiation by Activating the Smad and ERK Signaling Pathways in HL60 Leukemia Cells" Molecular Cancer Therapeutics 2006 5:1452-1458.
Leach, J. K. and Mooney, D. J. "Bone Engineering by Controlled Delivery of Osteoinductive Molecules and Cells" Expert Opinion on Biological Therapy 2004 4(7):1015-1027.

(56) References Cited

OTHER PUBLICATIONS

Sun, S. "Bone Disease Drug Discovery: Examining the Interactions Between Osteoblast and Osteoclast" Expert Opinion on Therapeutic Targets 2008 12(2):239-251.
Begum et al. "Synthesis of 2β-Hydroxyursolic Acid and Other Ursane Analogs from Ursonic Acid" Australian Journal of Chemistry 1993 46(7):1067-1071.
Bowden et al. "Constituents of the Fruit of *pseudopanax arboreum* (Araliaceae)" Australian Journal of Chemistry 1975 28(1):91-107.
Campbell et al. "Endocyclic α,β-unsaturated Ketones. VI. Ultraviolet and Infrared Absorption Spectra and Resonance Stabilization" Bioorganic and Medicinal Chemistry Letters 1997 7(13):1623-1628.
Chattopadhyay et al. "Studies on Autoxidation: Part IV. Synthesis of Isometric 2,3-diols of olean-12-en-28-oate and Isohopane (moretane)" Indian Journal of Chemistry, Section B: Organic Chemistry Including Medicinal Chemistry 1977 15(1):21-24.
Devi et al. "Constituents of Black Dammar Resin and Some Transformation Products of α- and β-amyrins" Indian Journal of Chemistry 1969 7(12):1279-1280.
Elgamal et al. "Glycyrrhetic Acid Derivatives with Modified Ring A" Journal of Pharmaceutical Sciences 1973 62(9):1557-1558.
Elgamal et al. "The C-2,C-3-glycol Derivatives of Gylcyrrhetic Acid" Tetrahedron 1974 30(23/24):4083-4087.
Endová et al. "Preparation of 2,3-secodiacids of the Lupane Series" Collection of Czechoslovak Chemical Communications 1994 59(6):1420-1429.
Evers et al. "Betulinic Acid Derivatives: A New Class of Human Immunodeficiency Virus Type I Specific Inhibitors with a New Mode of Action" Journal of Medicinal Chemistry 1996 39(5):1056-1068.
Ganguly et al. "Oxidation of Ring in a Lupeol" Tetrahedron 1966 22(10):3597-3599.
García-Granados et al. "Semi-Synthesis of Triterpene A-Ring Derivatives from Oleanolic and Maslinic Acids. Theoretical and Experimental $^{13}$C Chemical Shifts" Journal of Chemical Research, Synopses, 2000 2:56-57.
García-Granados et al. "Semi-Synthesis of Triterpene A-ring Derivatives from Oleanolic and Maslinic Acids. Part II. Theoretical and Experimental $^{13}$C Chemical Shifts" Journal of Chemical Research, Synopses, 2000 5:211-212.
Glen et al. "Isolation of a New Triterpenoid from Rose-bay Willowherb" Chemistry and Industry, London, United Kingdom 1965 46:1908.
Govidachari et al. "Gymnosporol, A New Pentacyclic Triterpene from gymnosporia rothiana" Indian Journal of Chemistry 1970 8(5):395-397.
Green, G. F. H. and Long, A. G. "Compounds Related to the Steroid Hormones. Part II. The Action of Hydrogen Bromide on 2-bromo-3-oxo-Δ$^1$-5α-steroids" Journal of the Chemical Society 1961 2532-2543.
Hanna, G. and Ourisson, R. "Studies of Cyclic Ketones. VIII. Preparation and Properties of Polycyclic α-diketones" Bulletin de la Societe Chemique de France 1961 1945-1951.
Hattori et al. "A Triterpene from the Fruits of *rubus chingii*" Phytochemistry 1988 27(12):3975-3976.
Huneck, S. "Triterpene, XIV: Die Bromierung Von 19β28-epoxy-3-oxo-2-diazo-und-1-oxo-2-diazo-Sowie von 19β28-epoxy-1-oxo-18αH-oleanan" Chemische Berichte 1965 98(9):2873-2843.
Khan et al. "α-amyrin Derivatives from *corchorus depressus*" Phytochemistry 1991 30(6):1989-1992.
Klinot, J. and Vystrcil, A. "Triterpenes. VII. Stereochemistry of 2-bromo Derivatives of Allobetuline and Alloheterobetaline" Collection of Czechoslovak Chemical Communications 1966 31(3):1079-1092.
Klinot et al. "Triterpenes. Part LXXXVI. Triterpenoid 2,3-ketols, diols and their Acetates: Preparation and Conformation of the Ring A" Collection of Czechoslovak Chemical Communications 1989 54(2):400-412.
Kumar, N. and Seshadri, T. R. "Triterpenoids of *pterocarpus santalinus*: Constitution of a New Lupene Diol" Phytochemistry 1975 14(2):521-523.
Kundu et al. "Synthese von 2α-methoxycarbonyl-A-nor-lupa" Chemische Beerichte 1968 101(9):3255-3264.
Lavie, D. and Shvo, Y. "Constituents of Ecballium Elaterium: Proposed Structure for Elatericin A and B" Chemistry and Industry 1959 429-430.
Lawrie et al. "Isolation of Derivatives of Ursolic Acid from Apple Skin" Chemistry and Industry 1966 41:1720.
Lehn, J. M. and Ourisson, G. "Syntheses in the Lupane Series" Bulletin de la Societe Chimque de France 1962 1133-1136.
Lehn, J. M. and Vystreil, A. "Resonance Magnetique Nucleaire de Produits Naturels—VI: Triterpènes Dérivés de la Bétuline" Tetrahedron 1963 19(11):1733-1745.
Lehn, J. M. and Ourisson, G. "Nuclear Magnetic Response (N.M.R.) of Natural Products. I. General Introduction. Triterpenes of the Lupane Series. Methyl Groups" Bulletin de la Societe Chimique de France 1962 1137-1142.
Li et al. "Studies on Constituents of Rosa Multiflora Thunb" Zhongguo Yaoke Daxue Xuebao 2002 33(3):184-187.
Lugemwa et al. "A Heliothis Zea Antifeedant from the Abundant Birchbark Triterpene Betulin" Journal of Agricultural and Food Chemistry 1990 38(2):493-496.
Mane, R. A. and Ingle, D. B. "Synthesis and Biological Activity of Some New 1,5-benzothiazepines Containing Thiazole Moiety: 2-aryl-4-(4-methyl-2-substituted-aminothiazol-5-yl)-2,3-dihydro-1, 5-benzothiazepines" Indian Journal of Chemistry, Section B: Organic Chemistry Including Medicinal Chemistry 1982 21B(10):973-974.
Manzoor-i-Khuda, M. and Habermehl, G. "Chemical Constitutents of Corchorus Capsularis and *C. Olitorium* (Jute Plant). III. Structure of Corosin" Zietschrift fuer Naturforschung, Teil C: Biochemie, Biophysik, Biologie, Virologie 1974 29(5-6):209-221.
Manzoor-i-Khuda, M. "Isolation Techniques for Active Principles from Plants and their Composition and Structure Determination through Spectroscopic Techniques" New Trends Nat. Prod. 1986 26:303-323.
Misra et al. "Studies on Autoxidation: Part II—Synthesis of Isomeric 2,3-diols of Δ12-oleanen" Indian Journal of Chemistry, Section B: Organic Chemistry Including Medicinal Chemistry 1976 14B(6):411-414.
Osman et al. "Application of Chemical Reactions on Thin-Layer Chromatoplates. IV. Triterpene" Bulletin of the Chemical Society of Japan 1974 47(8):2056-2058.
Osman et al. "Chemical Studies on Pentacyclic Triterpenes. I. Benzilic Acid Rearrangement of Ring A in Ursolic Acid" Egyptian Journal of Chemistry 1972 15(3):269-272.
Picard et al. "Structure of the Triterpenes" J. Soc. Chem. Ind. 1939 58:58-59.
Pitzele, B. S. "Synthesis of 2-Oxygenated Glycyrrhetic Acid Derivatives" Journal of Medicinal Chemistry 1974 117(2):191-194.
Pradhan, B. P. and De, S. "Preparation of Triterpenoid Dioxpheenol via Oximinoketone and Structure of Baccatin" Indian Journal of Chemistry, Section B: Organic Chemistry including Medicinal Chemistry 1982 21B(9):823-828.
Pradhan, B. P. and Gosh, P. "Studies on Reactions of 2- bromo-3-ketotriterpenoids: Part IV. Debromination and Dehydrobromination of 2α-bromo and 2,2-dibromo Derivatives of Lupanone and Methyl Dihydrobetulonate" Indian Journal of Chemistry, Section B: Organic Chemistry including Medicinal Chemistry 1994 33B(1):73-75.
Sejbal et al. "Triterpenes. Part LXXIII. Reactions of Triterpenod Ketones with Sulfur and Morpholine under Willgerodt-Kindler Reaction Conditions" Collection of Czechoslovak Chemical Communications 1986 51(1):118-127.
Sejbal et al. "Triterpenes. Part XC. Conversion of Betulin into Careyagenolide (2α,3β-dihydroxy-18α, 19βH-ursan-28, 20β-olide" Collection of Czechoslovak Chemical Communications 1989 54(4):1036-1042.
Shimao, I. and Oae, S. "The Wallach Rearrangement of Some 4,4'-disubstituted Azoxybenzenes" Bulletin of the Chemical Society of Japan 1983 56(2):643-644.

(56) References Cited

OTHER PUBLICATIONS

Witz et al. "Cyclic Ketones. XIII. Circular Dichroism of Steroid and Triterpene Ketones. Conformation of Ring A of 8-methylated 3-oxotriterpenes" Bull Soc China, France 1963 1101-1112.
Office Communication dated Aug. 2, 2010 from U.S. Appl. No. 11/941,723 filed Nov. 16, 2007.
International Preliminary Report on Patentability issued in PCT/US2007/085006, dated Jul. 14, 2009.
International Search Report issued in PCT/US2007/085006, dated Aug. 7, 2009.
Niikura et al. "The Effects of Synthetic Triterpenoids on SZP Synthesis in Articular Chondrocytes" Osteoarthritis and Cartilage 2006 14:S112-S113.
Niikura et al. "The Effects Synthetic Triterpenoids on Superficial Zone Protein Synthesis in the Articular Chondrocytes" Abstract submitted 53$^{rd}$ meeting of the Orthopedic Research. Society, San Diego 2007.
Vincenti et al. "The Synthetic Triterpenoid TP-222 Inhibits RANKL Induction of Differentiation and MMP-9 Gene Expression in Osteoclasts" Abstract Presented at 70$^{th}$ Annual Scientific Meeting of the American College of Rheumatology 41$^{st}$ Annual Scientific Meeting 2006.
Ito et al. "Repulsive Axon Guidance Molecule Sema3A Inhibits Branching Morphogenesis of Fetal Mouse Lung" Mechanisms of Development 2000 97:35-45.
Ito et al. "Structural Comparison of Three Types of Staphylococcal Cassette Chromosome mec Integrated in the Chromosome in Methicillin-Resistant *Staphylococcus aureus*" Antimicrobial Agents and Chemotherapy 2001 45(5):1323-1336.
Office Communication dated Dec. 24, 2013 from U.S. Appl. No. 13/466,473, filed May 8, 2012.
Office Communication dated Apr. 1, 2014 from U.S. Appl. No. 13/466,473, filed May 8, 2012.
Cannon, J.G., Chapter 19 in Burger's Medicinal Chemistry and Drug Discovery, Fifth Edition, vol. I: Principles and Practice, Wiley-Interscience 1995, pp. 783-802.
Office Communication dated Jul. 1, 2014 from U.S. Appl. No. 13/466,473, filed May 8, 2012.
Hartwig, J. F. "Carbon-Heteroatom Bonding-Forming Reductive Eliminations of Amines, Ethers, and Sulfides" Accounts of Chemical Research 1998 31(12):852-860.
Hartwig, J. F. "Transition Metal Catalyzed Synthesis of Arylamines and Aryl Ethers from Aryl Halides and Triflates: Scope and Mechanism" Angewandate Chemie International Edition 1998 37:2047-2067.
Hartwig, J. F. "Approaches to Catalyst Discovery. New Carbon-Heteroatom and Carbon-Carbon Bond Formation" Pure and Applied Chemistry 1999 71(8):1417-1423.
King et al. "Highly General Stereo-, Regio-, and Chemo-Selective Synthesis of Terminal and Internal Conjugated Enynes by the Pd-Catalysed Reaction of Alkynylzinc Reagents with Alkenyl Halides" Journal of the Chemical Society, Chemical Communications 1977 19:683-684.
Kosugi et al. "Reactions of Allyltin Compounds III. Allylation of Aromatic Halides with Allyltributyltin in the Presence of Tetrakis(Triphenylphosphine)Palladium(0)" Chemistry Letters 1977:301-302.
Milstein, D. and Stille, J. K. "A General, Selective, and Facile Method for Ketone Synthesis from Acid Chlorides and Organotin Compounds Catalyzed by Palladium" Journal of the American Chemical Society 1978 100(11):3636-3638.
Miyaura et al. "A New Stereospecific Cross-Coupling by the Palladium-Catalyzed Reaction of 1-Alkenylboranes with 1-Alkenyl or 1-Alkynyl Halides" Tetrahedron Letters 1979 36:3437-3440.
Miyaura, N. and Suzuki, A. "Palladium-Catalyzed Cross-Coupling Reactions of Organoboron Compounds" Chemical Reviews 1995 95(7):2457-2483.
Muci, A. R. and Buchwald, S. L. "Practical Palladium Catalysts for C—N and C—O Bond Formation" Topics in Current Chemistry 2002 219:133-209.
Porcheddu et al. "Microwave-Assisted Synthesis of Isonitriles: A General Simple Methodology" Journal of Organic Chemistry 2005 70:2361-2363.
Wolfe et al. "Rational Development of Practical Catalysts for Aromatic Carbon-Nitrogen Bond Formation" Accounts of Chemical Research 1998 31(12):805-818.
Yang, B. H. and Buchwald, S. L. "Palladium-Catalyzed Amination of Aryl Halides and Sulfonates" Journal of Organometallic Chemistry 1999 576:125-146.
Office Communication dated May 27, 2014 from U.S. Appl. No. 13/466,456, filed May 8, 2012.
PCT, International Preliminary Report on Patentability in Int. App. No. PCT/US2013/039902 issued Nov. 11, 2014.

TRITERPENOIDS AND COMPOSITIONS CONTAINING THE SAME

INTRODUCTION

This patent application is a continuation of U.S. patent application Ser. No. 13/466,456 filed May 8, 2012, which is herein incorporated by reference in its entirety.

BACKGROUND OF THE INVENTION

One of the major needs in cancer prevention is the development of effective and safe new agents for chemoprevention. In particular, there is a need for chemopreventative agents targeted at mechanisms known to be involved in the process of carcinogenesis. In recent years, there has been a resurgence of interest in the study of mechanisms of inflammation that relate to carcinogenesis and in the use of such mechanisms as the basis for development of new chemopreventative agents.

The concept that inflammation and carcinogenesis are related phenomena has been the subject of many studies that have attempted to link these two processes in a mechanistic fashion (Sporn & Roberts (1986) *J. Clin. Invest.* 78:329-332; Ohshima & Bartsch (1994) *Mutat. Res.* 305:253-264). The enzymes that mediate the constitutive synthesis of nitric oxide and prostaglandins from arginine and arachidonate, respectively, have relative little significance for either inflammation or carcinogenesis. In contrast, inducible nitric oxide synthase (iNOS) and inducible cycloxygenase (COX-2) both have critical roles in the response of tissues to injury or infectious agents (Moncada, et al. (1991) *Pharmacol. Rev.* 43:109-142; Nathan & Xie (1994) *Cell* 78:915-918; Siebert & Masferrer (1994) *Receptor* 4(1):17-23; Tamir & Tannebaum (1996) *Biochim. Biophys. Acta* 1288:F31-F36). These inducible enzymes are essential components of the inflammatory process, the ultimate repair of injury, and carcinogenesis. While physiological activity of iNOS and COX-2 may provide a definite benefit to the organism, aberrant or excessive expression of either iNOS or COX-2 has been implicated in the pathogenesis of many disease processes, particularly in chronic degeneration of the central nervous system, carcinogenesis, septic shock, cardiomyopathy, and rheumatoid arthritis.

Triterpenoids, biosynthesized in plants by the cyclization of squalene, are used for medicinal purposes in many Asian countries; and some, like ursolic and oleanolic acids, are known to be anti-inflammatory and anti-carcinogenic (Huang, et al. (1994) *Cancer Res.* 54:701-708; Nishino, et al. (1988) *Cancer Res.* 48:5210-5215). However, the biological activity of these naturally occurring molecules is relatively weak, and therefore the synthesis of new analogs to enhance their potency has been undertaken (see, e.g., Honda, et al. (1997) *Bioorg. Med. Chem. Lett.* 7:1623-1628; Honda, et al. (1998) *Bioorg Med Chem. Lett.* 8(19):2711-2714).

In this respect, U.S. Pat. Nos. 6,326,507, 6,552,075, 7,288,568, 7,863,327, 8,034,955, US 2009/0060873, US 2009/0048204, WO 2008/136838 and WO 2009/023232 teach the use of 2-cyano-3,12-dioxooleana-1,9(11)-dien-28-oic acid (CDDO), and derivatives thereof such as 2-cyano-3,12-dioxoolean-1,9(11)-dien-28-oic acid methyl ester (CDDO-Me) and amide derivatives, for the treatment of diseases such as cancer, Alzheimer's disease, Parkinson's disease, inflammatory bowel diseases, and multiple sclerosis. Similarly, U.S. Pat. No. 6,974,801 and WO 2004/064723 teach the use of 2-cyano-3,12-dioxooleana-1,9(11)-dien-28-onitrile (CNDDO), 1-(2-cyano-3,12-dioxooleana-1,9(11)-dien-28-oyl) imidazole (CDDO-Im), 1-(2-cyano-3,12-dioxooleana-1,9(11)-dien-28-oyl)-2-methylimidazole, and 1-(2-cyano-3,12-dioxooleana-1,9(11)-dien-28-oyl)-4-methylimidazole in the prevention or treatment of cancer, Alzheimer's disease, Parkinson's disease, multiple sclerosis, rheumatoid arthritis, and other inflammatory diseases. Furthermore, the use of triterpenoids such as CDDO, CDDO-Me, CDDO-Im, and CDDO-Ethylamide in stimulating the growth and repair of bone and cartilage (US 2008/0233195 and WO 2008/064132) as well as in inhibiting HIV-1 replication (WO 2005/046732) has been described. US 2009/0326063 further teaches the use of synthetic triterpenoids in the prevention and treatment of renal/kidney disease, insulin resistance/diabetes, fatty liver disease, and/or endothelial dysfunction/cardiovascular disease.

Combination therapies of CDDO or CDDO-Me and a chemotherapeutic agent, immunosuppressive agent, or proteasome inhibitor are described in U.S. Pat. Nos. 7,435,755, 7,795,305, US 2009/0018146, US 2009/0048205, WO 2002/047611 and WO 2009/023845 for the treatment of cancer and graft versus host disease. Moreover, formulations for improved oral bioavailability of CDDO-Me are disclosed in WO 2010/093944.

Given the activity of CDDO and CDDO-Me, additional oleanolic acid derivatives have been developed for use in treating cancer, cardiovascular disease, neurodegenerative disease, renal/kidney disease, diabetes, arthritis and inflammatory conditions such as obesity, hypertension, atherosclerosis, coronary heart disease, stroke, peripheral vascular disease, hypertension, nephropathy, neuropathy, myonecrosis, ulcerative colitis, Crohn's disease, irritable bowel syndrome, retinopathy and metabolic syndrome. See U.S. Pat. Nos. 7,915,402, 7,943,778, US 2010/0048887, US 2010/0048892, US 2010/0048911, US 2011/0245206 and US 2011/0245233.

In view of the therapeutic activities of this class of triterpenoids, it would be advantageous to have compounds with improved activity.

SUMMARY OF THE INVENTION

The present invention is a triterpenoid compound of Formula I, II, VI, VII, VIII, IX, X, XI, XII, XIII, XIV, XV, or XVI, as defined herein and a pharmaceutical composition containing the same.

DETAILED DESCRIPTION OF THE INVENTION

Triterpenoids, including CDDO-Me derivatives, have now been developed. The triterpenoids described herein can be used in the treatment of disease, especially inflammatory diseases. Compounds particularly embraced by this invention have the structure of Formula I, which includes hydrates, isomers, prodrugs or pharmaceutically acceptable salts of Formula I:

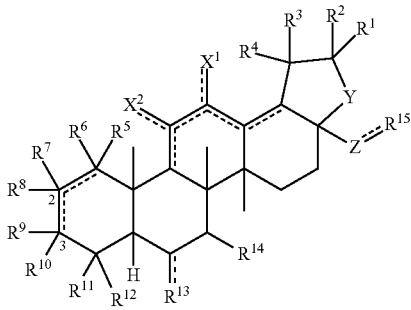

Formula I wherein,
at least one of $X^1$ and $X^2$ is $OR^a$, $NR^aR^b$, or $SR^a$, and the other of $X^1$ and $X^2$ is hydrogen, $OR^a$, $NR^aR^b$, or $SR^a$ wherein
$R^a$ is a hydrogen, cyano, —$CF_3$, nitro, amino, or substituted or unsubstituted heteroaryl group;
$R^b$ is hydrogen, hydroxyl, alkyl, aryl, aralkyl, acyl, alkoxy, aryloxy, acyloxy, alkylamino, arylamino, amido, or a substituted version of any of these groups; or a substituent convertible in vivo to hydrogen;
provided that $R^a$ is absent when the atom to which it is bound is part of a double bond, further provided that when $R^a$ is absent the atom to which it is bound is part of a double bond;
Y is $CH_2$ or $CH_2$—$CH_2$;
Z is a covalent bond, —C(=O)—, alkanediyl, alkenediyl, alkynediyl, or a substituted version of any of these groups;
the dashed bonds can be independently present or absent;
$R^1$, $R^2$, $R^3$ and $R^4$ are each independently a hydrogen, hydroxyl, alkyl, substituted alkyl, alkoxy or substituted alkoxy group;
at least one of $R^5$, $R^6$, $R^7$, $R^8$, $R^9$ or $R^{10}$ is independently —OMs, —$CH_2$OMs, —C(=O)C≡$CR^a$, —C≡$CCO_2R^a$, —C≡$CSO_2R^a$, —C≡CC(=O)$R^a$ or —$SO_2R^a$, or
$R^5$ and $R^6$, or $R^7$ and $R^8$, or $R^9$ and $R^{10}$ are together or =$CR^cR^d$, wherein
$R^c$ is hydrogen or alkylthiyl, and
$R^d$ is hydrogen, halo, alkylthiyl, or substituted or unsubstituted alkylsulfonyl or alkylsulfonyl —O—;
the remainder of $R^5$, $R^6$, $R^7$, $R^8$, $R^9$ and $R^{10}$ are independently hydrogen, hydroxyl, halo, cyano, =O, —C≡$CR^a$, —$CO_2R^a$, —$COR^a$, alkyl, alkenyl, alkynyl, aryl, aralkyl, heteroaryl, heteroaralkyl, acyl, alkoxy, aryloxy, acyloxy, alkylamino, arylamino, nitro, amino, amido, —C(O)$R^e$ or a substituted version of any of these groups, wherein
$R^e$ is hydrogen, hydroxy, halo, amino, hydroxyamino, azido or mercapto; or $C_1$-$C_{15}$-alkyl, $C_2$-$C_{15}$-alkenyl, $C_2$-$C_{15}$-alkynyl, $C_6$-$C_{15}$-aryl, $C_7$-$C_{15}$-aralkyl, $C_1$-$C_{15}$-heteroaryl, $C_2$-$C_{15}$-heteroaralkyl, $C_1$-$C_{15}$-acyl, $C_1$-$C_{15}$-alkoxy, $C_2$-$C_{15}$-alkenyloxy, $C_2$-$C_{15}$-alkynyloxy, $C_6$-$C_{15}$-aryloxy, $C_7$-$C_{15}$-aralkyloxy, $C_1$-$C_{15}$-heteroaryloxy, $C_2$-$C_{15}$-heteroaralkyloxy, $C_1$-$C_{15}$-acyloxy, $C_1$-$C_{15}$-alkylamino, $C_2$-$C_{15}$-dialkylamino, $C_1$-$C_{15}$-alkoxyamino, $C_2$-$C_{15}$-alkenylamino, $C_2$-$C_{15}$-alkynylamino, $C_6$-$C_{15}$-arylamino, $C_7$-$C_{15}$-aralkylamino, $C_1$-$C_{15}$-heteroarylamino, $C_2$-$C_{15}$-heteroaralkylamino, $C_1$-$C_{15}$-alkylsulfonylamino, $C_1$-$C_{15}$-amido, $C_1$-$C_{15}$-alkylsilyloxy, or substituted versions of any of these groups;
$R^{11}$ and $R^{12}$ are each independently hydrogen, hydroxyl, halo, alkyl, alkenyl, alkynyl, aryl, aralkyl, heteroaryl, heteroaralkyl, acyl, alkoxy, aryloxy, aralkoxy, heteroaryloxy, hetero-aralkoxy, acyloxy, alkylamino, dialkylamino, arylamino, aralkylamino, heteroarylamino, heteroaralkylamino, amido, or a substituted version of any of these groups, or
$R^{11}$ and $R^{12}$ are taken together and are alkanediyl, alkenediyl, arenediyl, alkoxydiyl, alkenyloxydiyl, alkylaminodiyl, alkenylaminodiyl, or alkenylaminooxydiyl;
$R^{13}$ is hydrogen, hydroxy or oxo;
$R^{14}$ is hydrogen or hydroxyl; and
$R^{15}$ is
a hydrogen, hydroxyl, —$NR^fR^g$, cyano, halo, azido, phosphate, 1,3-dioxoisoindolin-2-yl, mercapto, silyl or —COOH group,
substituted or unsubstituted versions of $C_1$-$C_{15}$-alkyl, $C_2$-$C_{15}$-alkenyl, $C_2$-$C_{15}$-alkynyl, $C_6$-$C_{15}$-aryl, $C_7$-$C_{15}$-aralkyl, $C_1$-$C_{15}$-heteroaryl, $C_2$-$C_{15}$-heteroaralkyl, $C_1$-$C_{15}$-acyl, $C_1$-$C_{15}$-alkoxy, $C_2$-$C_{15}$-alkenyloxy, $C_2$-$C_{15}$-alkynyloxy, $C_6$-$C_{15}$-aryloxy, $C_7$-$C_{15}$-aralkyloxy, $C_1$-$C_{15}$-heteroaryloxy, $C_2$-$C_{15}$-heteroaralkyloxy, $C_1$-$C_{15}$-acyloxy, $C_1$-$C_{15}$-alkylamino, $C_2$-$C_{15}$-alkenylamino, $C_2$-$C_{15}$-alkynylamino, $C_6$-$C_{15}$-arylamino, $C_7$-$C_{15}$-aralkylamino, $C_1$-$C_{15}$-heteroarylamino, $C_2$-$C_{15}$-heteroaralkylamino, $C_1$-$C_{15}$-amido, $C_1$-$C_{15}$-alkylthio, $C_2$-$C_{15}$-alkenylthio, $C_2$-$C_{15}$-alkynylthio, $C_6$-$C_{15}$-arylthio, $C_7$-$C_{15}$-aralkylthio, $C_1$-$C_{15}$-heteroarylthio, $C_2$-$C_{15}$-heteroaralkylthio, $C_1$-$C_{15}$-acylthio, $C_1$-$C_{12}$-thioacyl, $C_1$-$C_{12}$-alkylsulfonyl, $C_2$-$C_{12}$-alkenylsulfonyl, $C_2$-$C_{12}$-alkynylsulfonyl, $C_6$-$C_{12}$-arylsulfonyl, $C_7$-$C_{12}$-aralkylsulfonyl, $C_1$-$C_{12}$-heteroarylsulfonyl, $C_1$-$C_{12}$-heteroaralkylsulfonyl, $C_1$-$C_{12}$-alkylsulfinyl, $C_2$-$C_{12}$-alkenylsulfinyl, $C_2$-$C_{12}$-alkynylsulfinyl, $C_6$-$C_{12}$-aryl sulfinyl, $C_7$-$C_{12}$-aralkylsulfinyl, $C_1$-$C_{12}$-heteroarylsulfinyl, $C_1$-$C_{12}$-heteroaralkylsulfinyl, $C_1$-$C_{12}$-alkylphosphonyl, $C_1$-$C_{12}$-alkylphosphate, $C_2$-$C_{12}$-dialkylphosphate, $C_1$-$C_{12}$-alkylammonium, $C_1$-$C_{12}$-alkylsulfonium, $C_1$-$C_{15}$-alkylsilyl, or a substituted version of any of these groups,
a —$CO_2$Me, carbonyl imidazole, —CO-D-Glu(OAc)$_4$, —$CONH_2$, —$CONHNH_2$, —$CONHCH_2CF_3$, or —C(=O)-heteroaryl group, or
Z and $R^{15}$ form a three to seven-membered ring, such that Z and $R^{15}$ are further connected to one another through one or more of —O— and alkanediyl, further wherein Z is —CH— and $R^{15}$ is —$CH_2$— or Z, $R^{15}$, and carbon numbers 13, 17 and 18 form a ring such that $R^{15}$ is bound to carbon 13, wherein Y is methanediyl or substituted methanediyl and $R^{15}$ is —O—, wherein
$R^f$ and $R^g$ are independently hydrogen, hydroxyl, alkyl, alkenyl, alkynyl, aryl, aralkyl, heteroaryl, heteroaralkyl, acyl, alkoxy, alkenyloxy, alkynyloxy, aryloxy, aralkoxy, heteroaryloxy, heteroaralkoxy, thioacyl, alkylsulfonyl, alkenylsulfonyl, alkynylsulfonyl, arylsulfonyl, aralkylsulfonyl, heteroarylsulfonyl, or heteroaralkylsulfonyl, or a substituted version of any of these groups.

In certain embodiments, the bond between $C_2$ and $C_3$ in the A-ring is a double bond. In other embodiments, the bond between $C_2$ and $C_3$ in the A-ring is a single bond.

In some embodiments, the compound of the invention is a dimer as represented by the Formula II,

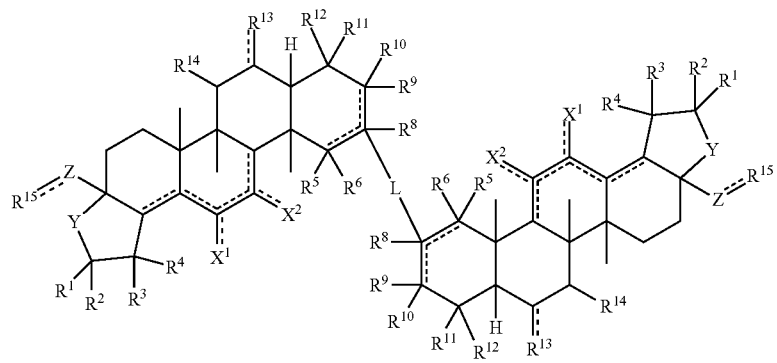

Formula II wherein $X^1$, $X^2$, Y, Z, $R^1$, $R^2$, $R^3$, $R^4$, $R^8$, $R^9$, $R^{11}$, $R^{12}$, $R^{13}$, $R^{14}$ and $R^{15}$ are as defined for Formula I and L is —C≡C— R—C≡C—, —C(=O)—, —C≡C—, —C≡C—N(—R)—, —C(=O)—N(—R)—, —C≡C—C(=O)—, —Ar—C(=O)—, or —C≡C—C(=O)—Ar—, wherein R is hydrogen, or an alkyl, aryl, alkenyl, or alkynyl group. Exemplary dimers include compounds 10-17.

In yet other embodiments, the compound of the invention has the structure as set forth in Formulae VI-XVI. In particular embodiments, the triterpenoid compound of the invention is a compound selected from compound 18-75.

As used herein, "hydrogen" means —H; "hydroxyl" means —OH; "oxo" means =O; "halo" or "halogen" means independently —F, —Cl, —Br or —I; "hydroxyamino" means —NHOH; "nitro" means —NO$_2$; "cyano" means —CN; "azido" means —N$_3$; "mercapto" means —SH; "thio" means =S; "sulfonyl" means —S(O)$_2$— (see additional definitions of groups containing the term sulfonyl, e.g., alkylsulfonyl); and "silyl" means —SiH$_3$ (see additional definitions of group(s) containing the term silyl, e.g., alkylsilyl).

For the groups below, the following parenthetical subscripts further define the groups as follows: "(Cn)" defines the exact number (n) of carbon atoms in the group. For example, "$C_1$-$C_{15}$-alkoxy" designates those alkoxy groups having from 1 to 15 carbon atoms (e.g., 1, 2, 3, 4, 5, 6, 7, 8, 9, 10, etc. or any range derivable therein (e.g., 3-10 carbon atoms)).

The term "alkyl" refers to a non-aromatic monovalent group with a saturated carbon atom as the point of attachment, a linear or branched, cyclo, cyclic or acyclic structure, no carbon-carbon double or triple bonds, and no atoms other than carbon and hydrogen. The groups, —CH$_3$, —CH$_2$CH$_3$, —CH$_2$CH$_2$CH$_3$, —CH(CH$_3$)$_2$, —CH(CH$_2$)$_2$, —CH$_2$CH$_2$CH$_2$CH$_3$, —CH(CH$_3$)CH$_2$CH$_3$, —CH$_2$CH (CH$_3$)$_2$, —C(CH$_3$)$_3$, —CH$_2$C(CH$_3$)$_3$, cyclobutyl, cyclopentyl, cyclohexyl, and cyclohexylmethyl are non-limiting examples of alkyl groups.

The term "alkanediyl" refers to a non-aromatic divalent group, wherein the alkanediyl group is attached with two σ-bonds, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$ CH$_2$—, and —CH$_2$CH$_2$CH$_2$— are non-limiting examples of alkanediyl groups.

The term "alkenyl" refers to a monovalent group with a nonaromatic carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$, —CH=CHCH$_3$, —CH=CHCH$_2$CH$_3$, —CH$_2$CH=CH$_2$, —CH$_2$CH=CHCH$_3$, and —CH=CH—C$_6$H$_5$.

The term "alkenediyl" refers to a nonaromatic divalent group, wherein the alkenediyl group is attached with two σ-bonds, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$) CH$_2$—, and —CH=CHCH$_2$— are non-limiting examples of alkenediyl groups.

The term "alkynyl" refers to a monovalent group with a nonaromatic carbon atom as the point of attachment, a linear or branched, cyclo, cyclic or acyclic structure, at least one carbon-carbon triple bond, and no atoms other than carbon and hydrogen. The groups, —C≡CH, —C≡CCH$_3$, —C≡CC$_6$H$_5$ and —CH$_2$C≡CCH$_3$, are non-limiting examples of alkynyl groups.

The term "alkynediyl" refers to a nonaromatic divalent group, wherein the alkynediyl group is attached with two σ-bonds, with two carbon atoms as points of attachment, a linear or branched, cyclo, cyclic or acyclic structure, at least one carbon-carbon triple bond, and no atoms other than carbon and hydrogen. The groups, —C≡C—, —C≡CCH$_2$—, and —C≡CCH(CH$_3$)— are non-limiting examples of alkynediyl groups.

The term "aryl" refers to a monovalent group with an aromatic carbon atom as the point of attachment, said carbon atom forming part of a six-membered aromatic ring structure wherein the ring atoms are all carbon, and wherein the monovalent group is composed of carbon and hydrogen. Non-limiting examples of aryl groups include phenyl, methylphenyl, (dimethyl)phenyl, -ethylphenyl, propylphenyl, —C$_6$H$_4$CH(CH$_3$)$_2$, —C$_6$H$_4$CH(CH$_2$)$_2$, methylethylphenyl, vinylphenyl, naphthyl, and the monovalent group derived from biphenyl.

The term "arenediyl" refers to a divalent group, wherein the arenediyl group is attached with two σ-bonds, with two aromatic carbon atoms as points of attachment, said carbon atoms forming part of one or more six-membered aromatic ring structure(s) wherein the ring atoms are all carbon, and wherein the monovalent group is composed of carbon and hydrogen. Non-limiting examples of arenediyl groups include:

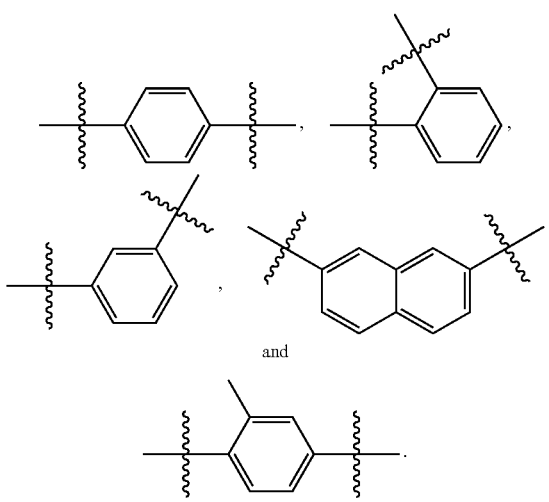

and

The term "aralkyl" refers to the monovalent group -alkanediyl-aryl, in which the terms alkanediyl and aryl are each used in a manner consistent with the definitions provided above. Non-limiting examples of aralkyls include 1-phenyl-ethyl, 2-phenyl-ethyl, indenyl and 2,3-dihydro-indenyl, provided that indenyl and 2,3-dihydro-indenyl are only examples of aralkyl in so far as the point of attachment in each case is one of the saturated carbon atoms.

The term "heteroaryl" refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group is composed of carbon, hydrogen, aromatic nitrogen, aromatic oxygen or aromatic sulfur. Non-limiting examples of aryl groups include acridinyl, furanyl, imidazoimidazolyl, imidazopyrazolyl, imidazopyridinyl, imidazopyrimidinyl, indolyl, indazolinyl, methylpyridyl, oxazolyl, phenylimidazolyl, pyridyl, pyrrolyl, pyrimidyl, pyrazinyl, quinolyl, quinazolyl, quinoxalinyl, tetrahydroquinolinyl, thienyl, triazinyl, pyrrolopyridinyl, pyrrolopyrimidinyl, pyrrolopyrazinyl, pyrrolotriazinyl, pyrroloimidazolyl, chromenyl (where the point of attachment is one of the aromatic atoms), and chromanyl (where the point of attachment is one of the aromatic atoms).

The term "heteroaralkyl" refers to the monovalent group -alkanediyl-heteroaryl, in which the terms alkanediyl and heteroaryl are each used in a manner consistent with the definitions provided above. Non-limiting examples of aralkyls include pyridylmethyl, and thienylmethyl.

The term "acyl" refers to a monovalent group with a carbon atom of a carbonyl group as the point of attachment, further having a linear or branched, cyclo, cyclic or acyclic structure. The groups, —CHO, —C(=O)CH$_3$, —C(=O)CH$_2$CH$_3$, —C(=O)CH$_2$CH$_2$CH$_3$, —C(=O)CH(CH$_3$)$_2$, —C(=O)CH(CH$_2$)$_2$, —C(=O)C$_6$H$_5$, —C(=O)C$_6$H$_4$CH$_3$, and —C(=O)C$_6$H$_4$CH$_2$CH$_3$ are non-limiting examples of acyl groups. The term "acyl" therefore encompasses, but is not limited to groups sometimes referred to as "alkyl carbonyl" and "aryl carbonyl" groups.

The term "alkoxy" refers to the group —OR, in which R is an alkyl, as that term is defined herein. Non-limiting examples of alkoxy groups include —OCH$_3$, —OCH$_2$CH$_3$, —OCH$_2$CH$_2$CH$_3$, —OCH(CH$_3$)$_2$, —OCH(CH$_2$)$_2$, —O-cyclopentyl, and —O-cyclohexyl.

Similarly, the terms "alkenyloxy," "alkynyloxy," "aryloxy," "aralkoxy," "heteroaryloxy," "heteroaralkoxy" and "acyloxy," refer to groups, defined as —OR, in which R is alkenyl, alkynyl, aryl, aralkyl, heteroaryl, heteroaralkyl and acyl, respectively, as those terms are defined above.

The term "alkoxydiyl" refers to a non-aromatic divalent group, wherein the alkoxydiyl group is attached with two σ-bonds, with (a) two saturated carbon atoms as points of attachment, (b) one saturated carbon atom and one oxygen atom as points of attachment, or (c) two oxygen atoms as points of attachment, further having a linear or branched, cyclo, cyclic or acyclic structure, no carbon-carbon double or triple bonds in the group's backbone, further having no backbone atoms other than carbon or oxygen and having at least one of each of these atoms in the group's backbone. The groups, —O—CH$_2$CH$_2$—, —CH$_2$—O—CH$_2$CH$_2$—, —O—CH$_2$CH$_2$—O— and —O—CH$_2$—O— are non-limiting examples of alkoxydiyl groups.

The term "alkenyloxydiyl" refers to a divalent group that is nonaromatic prior to attachment, wherein the alkenyloxydiyl group is attached with two σ-bonds, which may become aromatic upon attachment, with (a) two carbon atoms as points of attachment, (b) one carbon atom and one oxygen atom as points of attachment, or (c) two oxygen atoms as points of attachment, further having a linear or branched, cyclo, cyclic or acyclic structure, at least one carbon-carbon double bond that is non-aromatic at least prior to attachment, further having no backbone atoms other than carbon or oxygen and having at least one of each of these atoms in the group's backbone. The groups, —O—CH=CH—, —O—CH=CHO— and —O—CH=CHCH$_2$— are non-limiting examples of alkenyloxydiyl groups.

The term "amino" refers to a moiety of the formula —NRR', wherein R and R' are independently hydrogen, alkyl, cycloalkyl, heterocycloalkyl, aryl or heteroaryl.

The term "alkylamino" refers to the group —NHR, in which R is an alkyl, as that term is defined above. Non-limiting examples of alkylamino groups include —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC(CH$_3$)$_3$, —NH-cyclopentyl, and —NH-cyclohexyl.

Similarly, the terms "alkoxyamino," "alkenylamino," "alkynylamino," "arylamino," "aralkylamino," "heteroarylamino," "heteroaralkylamino," and "alkylsulfonylamino" refer to groups, defined as —NHR, in which R is alkoxy, alkenyl, alkynyl, aryl, aralkyl, heteroaryl, heteroaralkyl and alkylsulfonyl, respectively, as those terms are defined above. A non-limiting example of an arylamino group is —NHC$_6$H$_5$.

The term "dialkylamino" refers to the group —NRR', in which R and R' can be the same or different alkyl groups, or R and R' can be taken together to represent an alkanediyl having two or more saturated carbon atoms, at least two of which are attached to the nitrogen atom. Non-limiting examples of dialkylamino groups include —NHC(CH$_3$)$_3$, —N(CH$_3$)CH$_2$CH$_3$, —N(CH$_2$CH$_3$)$_2$, N-pyrrolidinyl, and N-piperidinyl.

The term "alkylaminodiyl" refers to a non-aromatic divalent group, wherein the alkylaminodiyl group is attached with two σ-bonds, with (a) two saturated carbon atoms as points of attachment, (b) one saturated carbon atom and one nitrogen atom as points of attachment, or (c) two nitrogen atoms as points of attachment, further having a linear or branched, cyclo, cyclic or acyclic structure, no double or triple bonds in the group's backbone, further having no backbone atoms other than carbon or nitrogen and having at least one of each of these atoms in the group's backbone. The groups, —NH—CH$_2$CH$_2$—, —CH$_2$—NH—CH$_2$CH$_2$—, —NH—CH$_2$CH$_2$—NH— and —NH—CH$_2$—NH— are non-limiting examples of alkylaminodiyl groups.

The term "alkenylaminodiyl" refers to a divalent group that is nonaromatic prior to attachment, wherein the alkenylaminodiyl group is attached with two σ-bonds, which may become aromatic upon attachment, with (a) two carbon atoms as points of attachment, (b) one carbon atom and one nitrogen atom as points of attachment, or (c) two nitrogen atoms as points of attachment, further having a linear or branched, cyclo, cyclic or acyclic structure, at least one carbon-carbon double bond or carbon-nitrogen double that is non-aromatic at least prior to attachment, further having no backbone atoms other than carbon or nitrogen. The groups —NH—CH=CH—, —NH—CH=N— and —NH—CH=CH—NH— are non-limiting examples of alkenylaminodiyl groups.

The term "alkenylaminooxydiyl" refers to a divalent group, wherein the alkenylaminooxydiyl group is attached with two σ-bonds, which may become aromatic upon attachment, with two atoms selected from the group consisting of carbon, oxygen and nitrogen as points of attachment, further having a linear or branched, cyclo, cyclic or acyclic structure, at least one carbon-carbon double bond, carbon-nitrogen double, or nitrogen-nitrogen double bond that is non-aromatic at least prior to attachment, further having no backbone atoms other than carbon nitrogen or oxygen and having at least one of each of these three atoms in the backbone. The group —O—CH=N—, is a non-limiting example of an alkenylaminooxydiyl group.

The term "amido" (acylamino) refers to the group —NHR, in which R is acyl, as that term is defined herein. A non-limiting example of an acylamino group is —NHC(=O)CH$_3$.

The term "alkylthio" refers to the group —SR, in which R is an alkyl, as that term is defined above. Non-limiting examples of alkylthio groups include —SCH$_3$, —SCH$_2$CH$_3$, —SCH$_2$CH$_2$CH$_3$, —SCH(CH$_3$)$_2$, —SCH(CH$_2$)$_2$, —S-cyclopentyl, and —S-cyclohexyl.

Similarly, the terms "alkenylthio," "alkynylthio," "arylthio," "aralkylthio," "heteroarylthio," "heteroaralkylthio" and "acylthio" refer to groups, defined as —SR, in which R is alkenyl, alkynyl, aryl, aralkyl, heteroaryl, heteroaralkyl and acyl, respectively, as those terms are defined above.

The term "thioacyl" refers to a monovalent group with a carbon atom of a thiocarbonyl group as the point of attachment, further having a linear or branched, cyclo, cyclic or acyclic structure. The groups —CHS, —C(=S)CH$_3$, —C(=S)CH$_2$CH$_3$, —C(=S)CH$_2$CH$_2$CH$_3$, —C(=S)CH(CH$_3$)$_2$, —C(=S)CH(CH$_2$)$_2$, —C(=S)C$_6$H$_5$, —C(=S)C$_6$H$_4$CH$_3$, —C(=S)C$_6$H$_4$CH$_2$CH$_3$, —C(=S)C$_6$H$_3$(CH$_3$)$_2$, and —C(=S)CH$_2$C$_6$H$_5$, are non-limiting examples of thioacyl groups. The term "thioacyl" therefore encompasses, but is not limited to, groups sometimes referred to as "alkyl thiocarbonyl" and "aryl thiocarbonyl" groups.

The term "alkylsulfonyl" refers to the group —S(=O)$_2$R, in which R is an alkyl, as that term is defined above. Non-limiting examples of alkylsulfonyl groups include: —S(=O)$_2$CH$_3$, —S(=O)$_2$CH$_2$CH$_3$, —S(=O)$_2$CH$_2$CH$_2$CH$_3$, —S(=O)$_2$CH(CH$_3$)$_2$, —S(=O)$_2$CH(CH$_2$)$_2$, —S(=O)$_2$-cyclopentyl, and —S(=O)$_2$-cyclohexyl.

Similarly, the terms "alkenylsulfonyl," "alkynylsulfonyl," "arylsulfonyl," "aralkylsulfonyl," "heteroarylsulfonyl," and "heteroaralkylsulfonyl" refer to groups, defined as —S(O)$_2$R, in which R is alkenyl, alkynyl, aryl, aralkyl, heteroaryl, and heteroaralkyl, respectively, as those terms are defined above.

The term "alkylsulfinyl" refers to the group —S(=O)R, in which R is an alkyl, as that term is defined above. Non-limiting examples of alkylsulfinyl groups include —S(=O)CH$_3$, —S(=O)CH$_2$CH$_3$, —S(=O)CH$_2$CH$_2$CH$_3$, —S(=O)CH(CH$_3$)$_2$, —S(=O)CH(CH$_2$)$_2$, —S(=O)-cyclopentyl, and —S(=O)-cyclohexyl.

Similarly, the terms "alkenylsulfinyl," "alkynylsulfinyl," "arylsulfinyl," "aralkylsulfinyl," "heteroarylsulfinyl" and "heteroaralkylsulfinyl" refer to groups, defined as —S(=O)R, in which R is alkenyl, alkynyl, aryl, aralkyl, heteroaryl, and heteroaralkyl, respectively, as those terms are defined above.

The term "alkylammonium" refers to a group, defined as —NH$_2$R$^+$, —NHRR'$^+$, or —NRR'R"$^+$, in which R, R' and R" are the same or different alkyl groups, or any combination of two of R, R' and R" can be taken together to represent an alkanediyl. Non-limiting examples of alkylammonium cation groups include —NH$_2$(CH$_3$)$^+$, —NH$_2$(CH$_2$CH$_3$)+, —NH$_2$(CH$_2$CH$_2$CH$_3$)+, —NH(CH$_3$)$_2$$^+$, —NH(CH$_2$CH$_3$)$_2$$^+$, —NH(CH$_2$CH$_2$CH$_3$)$_2$$^+$, —N(CH$_3$)$_3$$^+$, —N(CH$_3$)(CH$_2$CH$_3$)$_2$$^+$, —N(CH$_3$)$_2$(CH$_2$CH$_3$)$^+$, —NH$_2$C(CH$_3$)$_3$$^+$, —NH(cyclopentyl)$_2$$^+$, and —NH$_2$(cyclohexyl)$^+$.

The term "alkylthiyl" refers to the group —SR. Non-limiting examples of alkylthiyl groups include —S(CH$_3$), —S(CH$_2$CH$_3$), —S(CH$_2$CH$_2$CH$_3$)—S(cyclopentyl), and —S(cyclohexyl).

The term "alkylsilyl" refers to a monovalent group, defined as —SiH$_2$R, —SiHRR', or —SiRR'R", in which R, R' and R" can be the same or different alkyl groups, or any combination of two of R, R' and R" can be taken together to represent an alkanediyl. The groups —SiH$_2$CH$_3$, —SiH(CH$_3$)$_2$, —Si(CH$_3$)$_3$ and —Si(CH$_3$)$_2$C(CH$_3$)$_3$, are non-limiting examples of unsubstituted alkylsilyl groups.

The term "alkylphosphonyl" refers to the group —OPO(OR)$_2$, where R is alkyl, as defined herein.

The term "alkylphosphate" refers to the group —OP(=O)(OH)(OR), in which R is an alkyl, as that term is defined above. Non-limiting examples of alkylphosphate groups include —OP(=O)(OH)(OMe) and —OP(=O)(OH)(OEt).

The term "dialkylphosphate" refers to the group —OP(=O)(OR)(OR'), in which R and R' can be the same or different alkyl groups, or R and R' can be taken together to represent an alkanediyl having two or more saturated carbon atoms, at least two of which are attached via the oxygen atoms to the phosphorus atom. Non-limiting examples of dialkylphosphate groups include —OP(=O)(OMe)$_2$, —OP(=O)(OEt)(OMe) and —OP(=O)(OEt)$_2$.

"Cycloalkyl" means a non-aromatic mono- or multicyclic ring system including about 3 to about 10 carbon atoms, preferably about 5 to about 10 carbon atoms. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Heterocyclyl" or "heterocycloalkyl" means a non-aromatic saturated monocyclic or multicyclic ring system including about 3 to about 10 ring atoms, preferably about 5 to about 10 ring atoms, in which one or more of the atoms in the ring system is an element other than carbon, for example nitrogen, oxygen or sulfur, alone or in combination. Preferred heterocyclyls contain about 5 to about 6 ring atoms. The prefix aza, oxa or thia before the heterocyclyl root name means that at least a nitrogen, oxygen or sulfur atom respectively is present as a ring atom. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. Non-limiting examples of suitable bicyclic heterocyclyl rings include decahydro-isoquinoline, decahydro-[2,6]naphthyridine, and the like.

Any of the groups described herein may be unsubstituted or optionally substituted. When modifying a particular group, "substituted" means that the group the term modifies may, but does not have to, be substituted. Substitutions typically replace an available hydrogen with an alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, alkoxyalkoxy, acyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, or heterocyclyl.

Any undefined valency on an atom of a structure shown in this application implicitly represents a hydrogen atom bonded to the atom.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

An "isomer" of a first compound is a separate compound in which each molecule contains the same constituent atoms as the first compound, but where the configuration of those atoms in three dimensions differs.

"Pharmaceutically acceptable salts" means salts of compounds of the present invention which are pharmaceutically acceptable, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and di-carboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiary-butylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

Compounds of the invention may also exist in prodrug form. Since prodrugs are known to enhance numerous desirable qualities of pharmaceuticals, e.g., solubility, bioavailability, manufacturing, etc., the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a patient, cleaves to form a hydroxy, amino, or carboxylic acid, respectively. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

A triterpenoid compound of this invention may be administered in a pharmaceutical composition by various routes including, but not limited to, oral, subcutaneous, intravenous, or intraperitoneal administration (e.g. by injection). Depending on the route of administration, the active compound may be coated in a material to protect the compound from the action of acids and other natural conditions which may inactivate the compound.

For example, to administer the therapeutic compound by other than parenteral administration, it may be necessary to coat the compound with, or co-administer the compound with, a material to prevent its inactivation. By way of illustration, the therapeutic compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan, et al. (1984) *J. Neuroimmunol.* 7:27).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a subject.

One or more triterpenoid compounds of the invention are administered at a therapeutically effective dosage sufficient to treat a condition in a subject. A "therapeutically effective dosage" preferably reduces the amount of symptoms of the condition in the infected subject by at least about 20%, more preferably by at least about 40%, even more preferably by at least about 60%, and still more preferably by at least about 80% relative to untreated subjects. For example, the efficacy of a compound can be evaluated in an animal model system that may be predictive of efficacy in treating the disease in humans The triterpenoid compounds of the invention are of use in modulating IFN-γ-induced NO production in macrophages, said composition having an $IC_{50}$ value of at least less than 0.6 μM, more preferably less than 0.001 μM.

In one embodiment, the instant triterpenoid compounds are of use in a method of modulating excessive nitric oxide or prostaglandin formation in a subject by administering to a subject a pharmaceutically effective amount of one or more triterpenoid compounds, such that the nitric oxide or prostaglandin formation is modulated.

In a further embodiment, the triterpenoid compounds of the invention are of use in a method of preventing or treating a disorder characterized by overexpression of iNOS or COX-2 genes, wherein the method includes administering to a subject a pharmaceutically effective amount of one or more triterpenoid compounds, such that the disorder is prevented or treated. In a preferred embodiment, the disorder includes cancer, diabetic nephropathy, neurodegenerative disease, rheumatoid arthritis, inflammatory bowel disease, and other diseases whose pathogenesis is believed to involve excessive production of either nitric oxide or prostaglandins. In a particular embodiment, the neurodegenerative disease includes Parkinson's disease, Alzheimer's disease, multiple sclerosis, and amyotrophic lateral sclerosis. The cancer may include, e.g., a leukemic cancer or a solid cancer. A leukemic cancer is a cancer of a blood cell, a myeloid cell, a monocytic cell, a myelocytic cell, a promyelocytic cell, a myeloblastic cell, a lymphocytic cell, or a lymphoblastic cell. A solid cancer is a cancer of a bladder cell, a breast cell, a lung cell, a colon cell, a prostate cell, a liver cell, a pancreatic cell, a stomach cell, a testicular cell, a brain cell, an ovarian cell, a skin cell, a brain cell, a bone cell, or a soft tissue cell.

Moreover, the invention provides methods for the treatment and prevention of graft versus host disease (GVHD) by providing a triterpenoid compound of the invention either alone or in conjunction with another agent, such as an immunosuppressive agent such as a corticosteroid or tacrolimus, or a chemotherapeutic agent for the treatment of GVHD. In graft versus host disease the donor immune system mounts a response against the host's organs or tissue. As CDDO compounds, either alone or in conjunction with other agents, can induce apoptosis by inhibiting Bcl-2 and have activity in lymphoid tissue, it is contemplated that the instant triterpenoid compounds can be used to provide therapy for graft versus host diseases.

The practice of the methods of the present invention will employ, unless otherwise indicated, conventional techniques of cell biology, cell culture, molecular biology, microbiology, recombinant DNA, and immunology, which are within the skill of the art. Such techniques are explained fully in the literature. See, for example, Genetics; Molecular Cloning A Laboratory Manual, 2nd Ed., ed. by Sambrook, J. et al. (1989) Cold Spring Harbor Laboratory Press; Short Protocols in Molecular Biology, 3rd Ed., ed. by Ausubel, F. et al. (1995) Wiley, NY; DNA Cloning, Volumes I and II (D. N. Glover ed., 1985); Oligonucleotide Synthesis (M. J. Gait ed. (1984)); Mullis et al. U.S. Pat. No. 4,683,195; Nucleic Acid Hybridization (B. D. Hames & S. J. Higgins eds. (1984)); the treatise, Methods In Enzymology (Academic Press, Inc., N.Y.); Immunochemical Methods In Cell And Molecular Biology (Mayer and Walker, eds., Academic Press, London (1987)); Handbook Of Experimental Immunology, Volumes I-IV (D. M. Weir and C. C. Blackwell, eds. (1986)); and Miller, J. Experiments in Molecular Genetics (Cold Spring Harbor Press, Cold Spring Harbor, N.Y. (1972)).

The invention is described in greater detail by the following non-limiting examples.

Example 1

Synthesis of Triterpenoids

The triterpenoids of the invention can be generally produced from natural compounds such as oleanolic acid, ursolic acid, betulinic acid, or hederagenin, or derivatives thereof that include additional A and/or C ring modifications. Synthesis of the compounds can be achieved using any conventional method of synthesizing similar triterpenoids such as CDDO or CDDO-Me. See, e.g., U.S. Pat. Nos. 6,326,507, 6,552,075, 6,974,801, 7,288,568, 7,863,327, 7,915,402, 7,943,778, 8,034,955, 8,071,632, 8,124,656, 8,124,799, 8,129,429 and WO 2009/146216.

As one example, triterpenoid compounds of the invention can be synthesized by (a) methylating the carboxylic acid group of a compound of Formula III to afford a methyl ester (Formula IV); oxidizing the hydroxyl group of a compound of Formula IV with an oxidizing agent to form a double bond in Ring A (Formula V), epoxidating Ring C of the enone to form an epoxide, and forming a C-ring enol and halogenating the A-ring enone to yield a compound of Formula VI (Scheme 1)

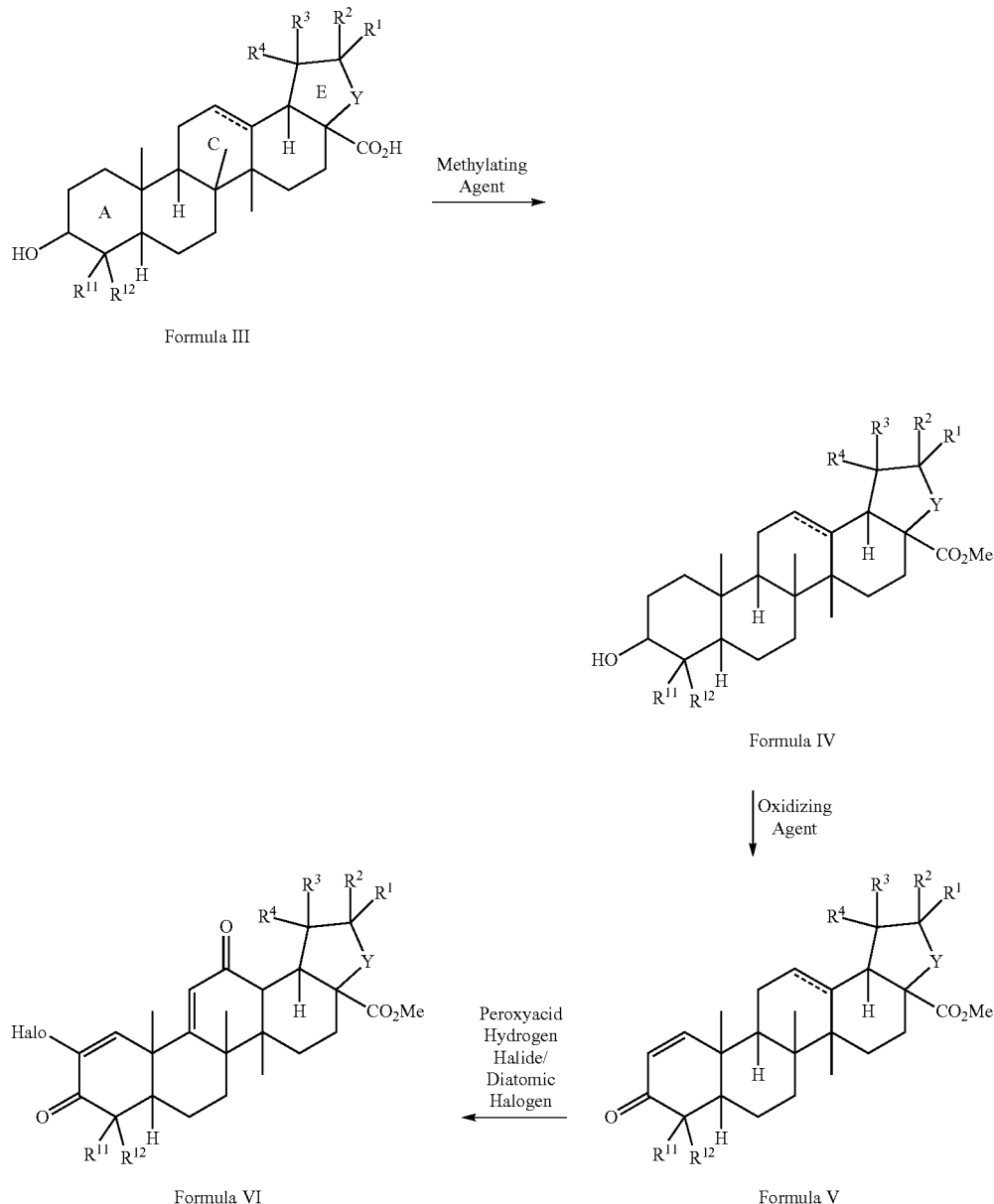

SCHEME 1

According to this example, the methylating agent is an electrophilic methyl source including, but not limited to iodomethane, dimethyl sulfate, dimethyl carbonate, diazomethane, or with methylating reagents such as methyl triflate or methyl fluorosulfonate, optionally in the presence of a base such as $K_2CO_3$ or $Li_2CO_3$. Further, the oxidizing agent can be an iodine oxidizing agent such as o-iodoxybenzoic acid (IBX)(Nicolaou, et al. (2002) *J. Am. Chem. Soc.* 124:2245-2258), diacetoxyiodobenzene (DAIB), fluorous DAIB (F-DAIB), Dess-Martin-Periodinane (DMP), or a stabilized formulation of IBX (SIBX; Ozanne, et al. (2003) *Org. Lett.* 5:2903) in one or a combination of suitable solvents such as DMSO and phenyl fluoride (fluorobenzene). Furthermore, epoxidation of Ring C can be carried out with an oxidant such as a peroxyacid, e.g., meta-chloroperoxybenzoic acid (mCPBA), peroxyacetic acid, or potassium peroxymonosulfate (Oxone). Acid catalyzed opening of the epoxide and bromination of the A Ring can be achieved with a hydrogen halide such as (HBr or HI) and a diatomic halogen molecule such as $Br_2$ or $I_2$.

As used in the context of the present invention, Formula III includes naturally occurring starting materials such as oleanolic acid, ursolic acid, betulinic acid, or hederagenin, or derivatives thereof.

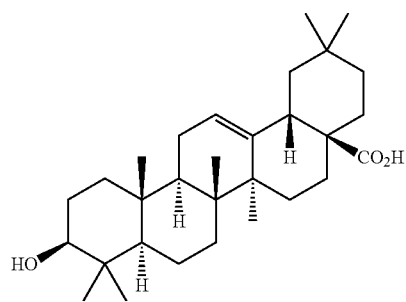

Oleanolic Acid

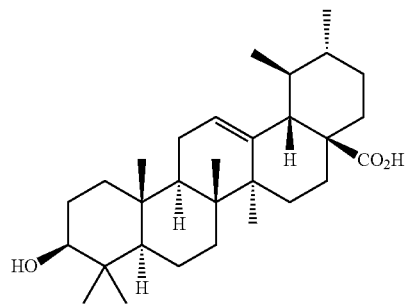

Ursolic Acid

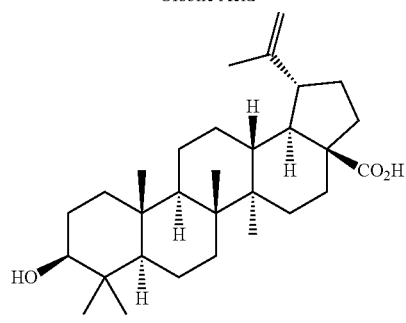

Betulinic Acid

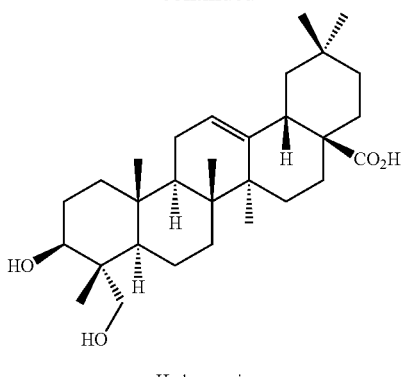

Hederagenin

As a specific example of using this synthetic method in the synthesis of triterpenoids, CDDO-Me was synthesized from oleanolic acid. As shown in Scheme 2, the natural triterpenoid oleanolic acid (1) was used as the starting material in the synthesis of CDDO-Me. The method commences with methylation of the carboxylic acid of oleanolic acid (1) to afford methyl ester 2 in quantitative yield. With ester 2, activation of the A-ring is fulfilled by 2-iodoxybenzoic acid-mediated two-fold oxidation to give enone 3. Epoxidation with meta-chloroperoxybenzoic acid, followed by direct C-ring enolization and A-ring enone bromination with bromine and hydrobromic acid, affords key intermediate 4. With bromide 4 in hand, a cross-coupling reaction with copper cyanide provides CDDO-Me (5) (Scheme 2). Intermediate 4 was prepared in high yield and few overall steps, thereby providing a base compound for development of the analogs and derivatives described herein.

SCHEME 2

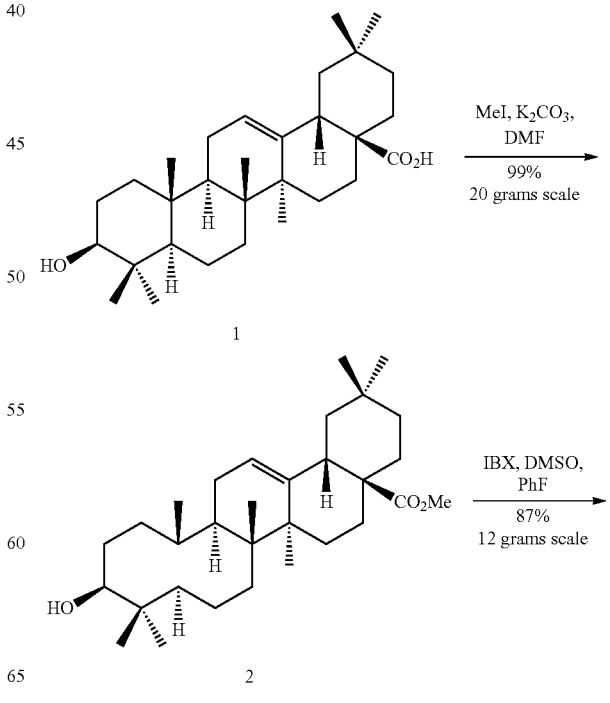

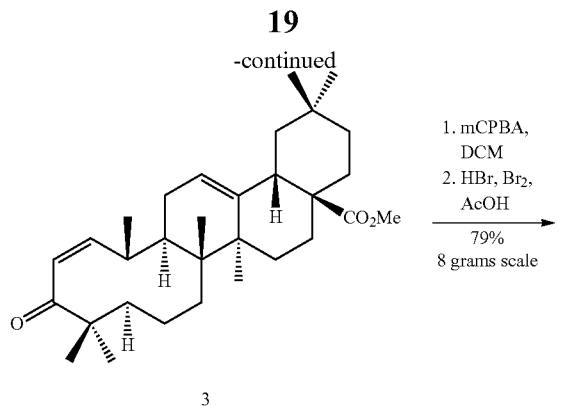

1. mCPBA, DCM
2. HBr, Br₂, AcOH

79%
8 grams scale

3

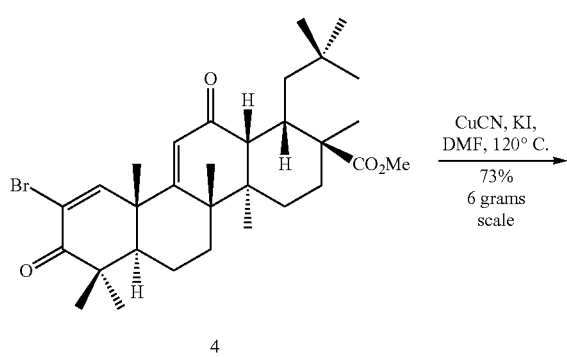

CuCN, KI, DMF, 120° C.

73%
6 grams scale

4

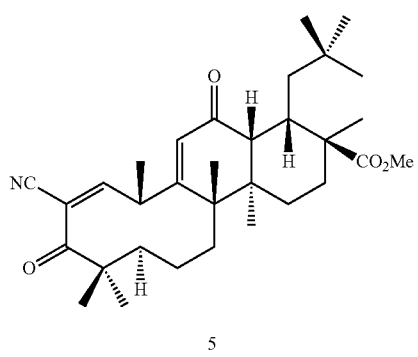

5

Unless otherwise specified, the reagents used in the instant methods are conventionally known in the art. For example, MeI refers to methyl iodide, DMF refers to dimethylformamide, IBX is 2-iodoxybenzoic acid, DMSO is dimethyl sulfoxide, PhF is phenyl fluoride, mCPBA refers to meta-chloroperoxybenzoic acid, HBr is hydrogen bromide, DCM is dichloromethane, AcOH is acetic acid, and CuCN is copper cyanide.

Example 2

Ring A Modifications

Given the reactivity of Ring A halogen, Formula VI serves as a substrate for the synthesis of the triterpenoid derivatives of the invention. For example, contact of a compound of Formula VI with a cyanide ion source such as $K_4[Fe(CN)_6]$, KCN, NaCN, ZnCN, CuCN, $(CH_3)_2C(—OH)CN$ or TMSCN results in the displacement of the aromatic halide with a cyanide ion. In other embodiments, the compound of Formula VI can be reacted with a wide variety of reagents to replace the halogen on Ring A. For example, the compound of Formula VI can be aminated or coupled or cross-coupled with an alkyl, alkenyl, alkynyl or aryl group to provide a variety of substituents on Ring A. For example, Formula VI can be aminated via Buchwald-Hartwig amination (Buchwald & Muci (2002) *Top. Curr. Chem.* 219:133-209; Hartwig (1999) *Pure Appl. Chem.* 71:1417; Buchwald & Yang (1999) *J. Orgmet. Chem.* 576:125; Hartwig (1998) *ACIEE* 37:2046; Hartwig (1998) *Acc. Chem. Res.* 31:852; Buchwald et al. (1998) *Acc. Chem. Res.* 31:805) to provide amides and amines 6 ($R^{16}$=H and $R^{17}$=H or CHO). Moreover, when 6 is a formamide ($R^{16}$=H and $R^{17}$=CHO), isonitrile 7 can be readily synthesized under mild conditions (Porcheddu, et al. (2005) *J. Org. Chem.* 70:2361-3). In addition, Sonogashira coupling (Sonogashira, et al. (1975) *Tetrahedron Lett.* 16:4467-70) provides alkynes 8 and 10. Likewise, Suzuki (Miyuara, et al. (1979) *Tetrahedron Lett.* 20:3437-40; Miyaura & Suzuki (1979) *Chem. Comm.* 19:866-7; Miyaura & Suzuki (1995) *Chem. Rev.* 95:2457-2483), Stille (Kosugi, et al. (1977) *Chem. Lett.* 301; Milstein & Stille (1978) *J. Am. Chem. Soc.* 100:3636), and Negishi (King, et al. (1977) *J. Chem. Soc. Chem. Commun.* 19:683) cross-coupling reactions provide compounds having the structure of compound 9 and dimers such as compounds 10-17 are readily produced when the halogen of Formula VI is iodide.

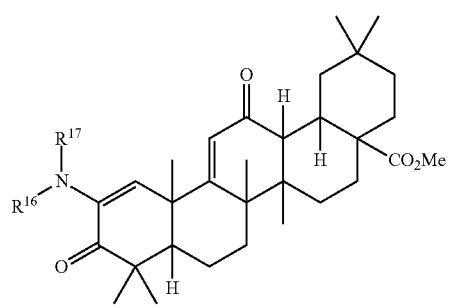

6

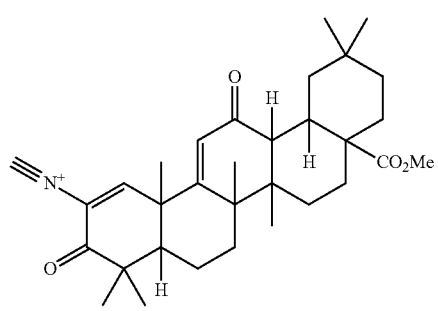

7

-continued
8
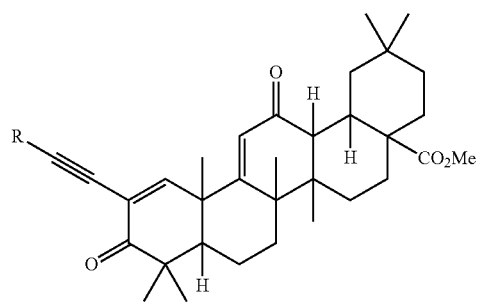
(R = alkyl, aryl, alkenyl, alkynyl)
9
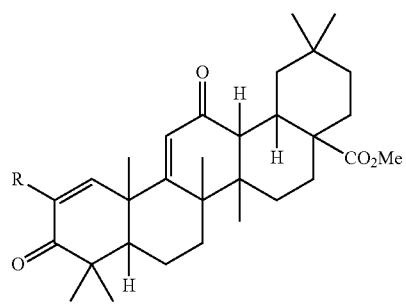
(R = alkyl, aryl, alkenyl, alkynyl)
10
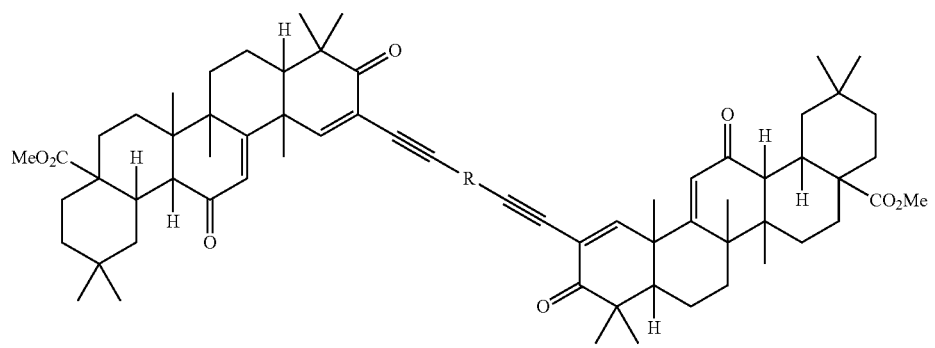
(R = alkyl, aryl, alkenyl, alkynyl)
11
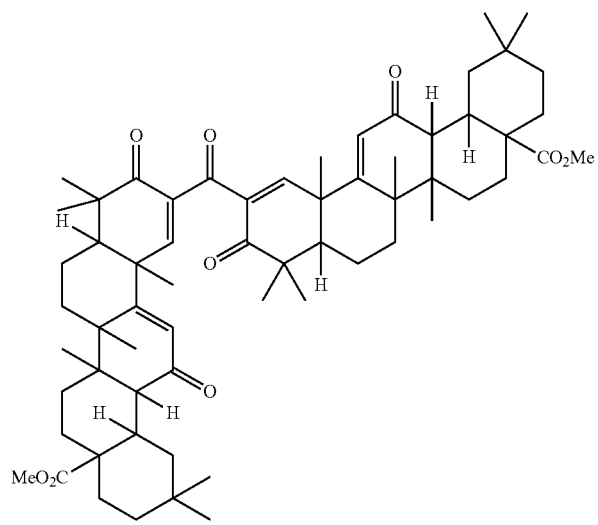

-continued
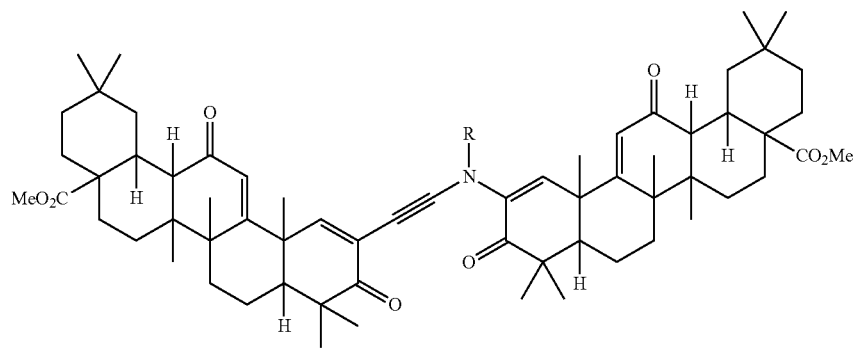
(R = H, alkyl, aryl, alkenyl, alkynyl)
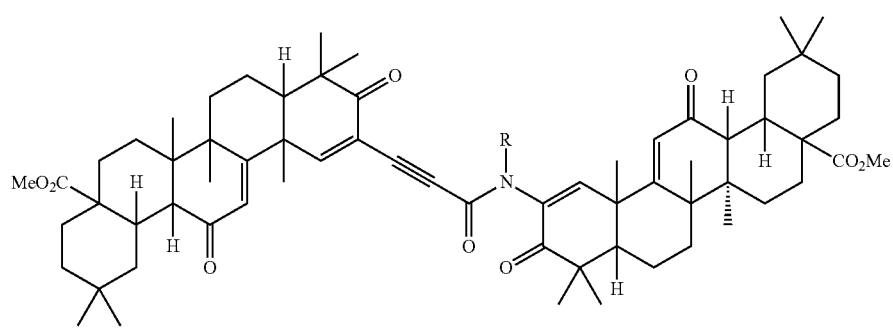
(R = H, alkyl, aryl, alkenyl, alkynyl)
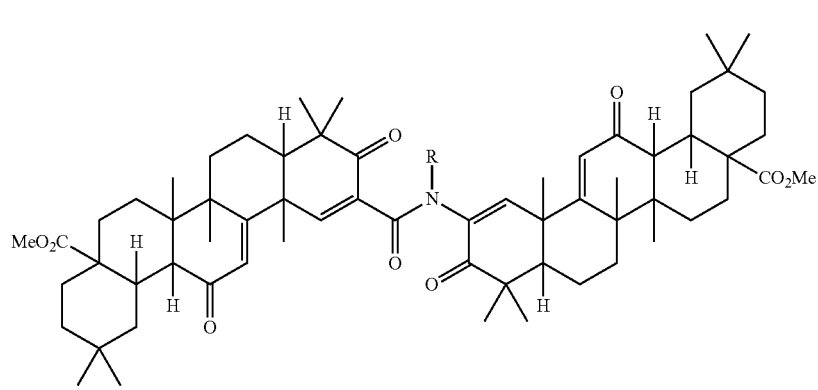
(R = H, alkyl, aryl, alkenyl, alkynyl)
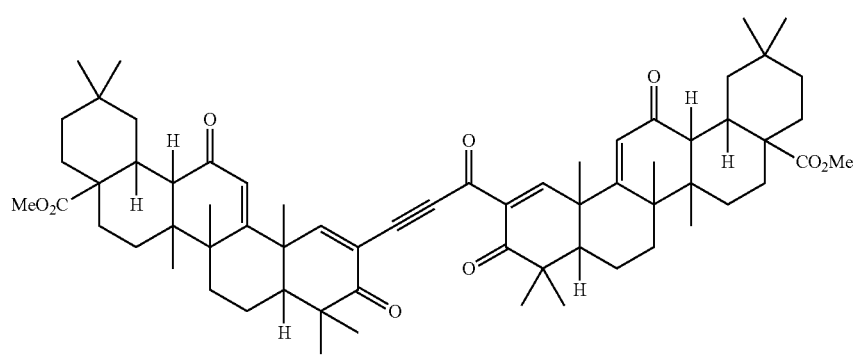

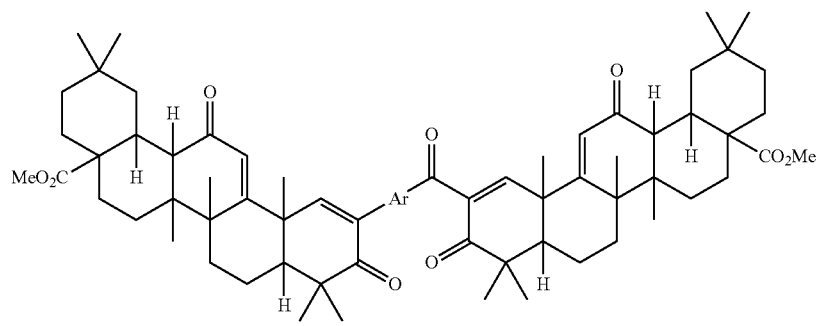

16

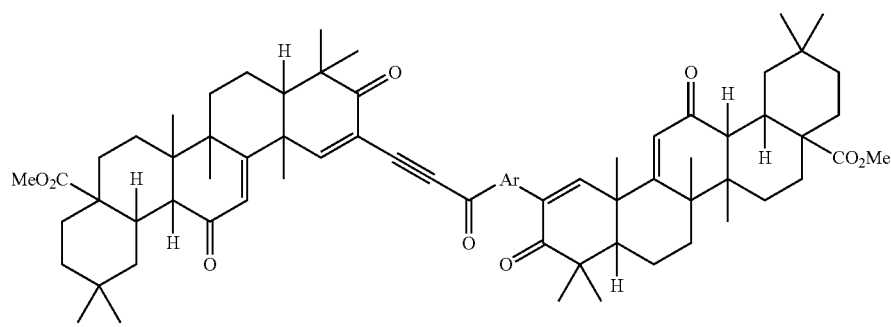

17

Example 3

Derivatives with Modifications at C-17

Amides (Formula VI), ethers (Formula VII), and esters (Formula VIII and Formula IX) are readily obtained using the instant method in combination with techniques known in the art. See U.S. Pat. No. 6,974,801 and US 2008/0233195.

Formula VI

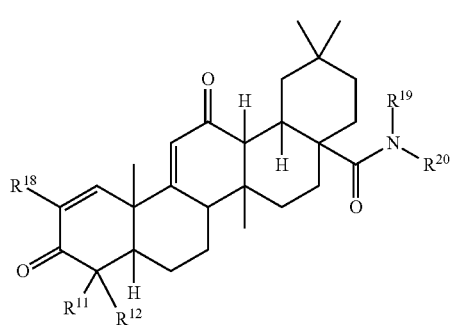

Formula VII

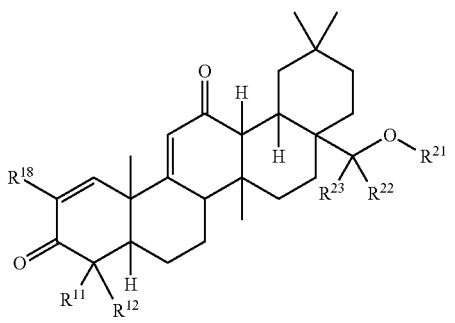

Formula VIII

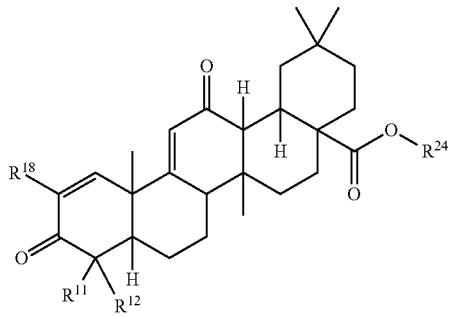

Formula IX

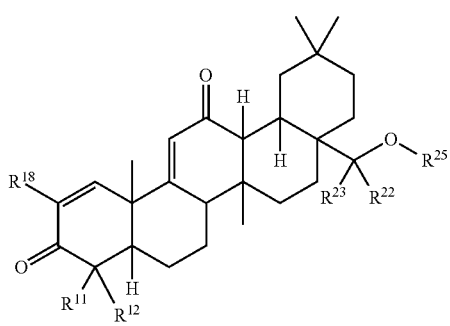

In accordance with Formulae VI-IX, $R^{11}$ and $R^{12}$ are as defined for Formula I;

$R^{18}$ is —OMs, —CH$_2$OMs, —C(=O)C≡CR$^a$, —C≡CCO$_2$R$^a$, —C≡CSO$_2$R$^a$, —C≡CC(=O)R$^a$, —SO$_2$R$^a$, =O or =CR$^c$R$^d$, wherein $R^d$ is hydrogen, halo, alkylthiyl, or substituted or unsubstituted alkylsulfonyl or alkylsulfonyl —O—;

$R^{22}$ and $R^{23}$ are independently a hydrogen, hydroxyl, halo, alkyl, nitro or amino group;

$R^{19}$, $R^{20}$, $R^{21}$, $R^{24}$ and $R^{25}$ are independently a hydrogen, hydroxyl, —$NR^fR^g$, cyano, halo, azido, phosphate, 1,3-dioxoisoindolin-2-yl, mercapto, silyl or —COOH group, substituted or unsubstituted versions of $C_1$-$C_{15}$-alkyl, $C_2$-$C_{15}$-alkenyl, $C_2$-$C_{15}$-alkynyl, $C_6$-$C_{15}$-aryl, $C_7$-$C_{15}$-aralkyl, $C_1$-$C_{15}$-heteroaryl, $C_2$-$C_{15}$-heteroaralkyl, $C_1$-$C_{15}$-acyl, $C_2$-$C_{15}$-alkenyloxy, $C_2$-$C_{15}$-alkynyloxy, $C_6$-$C_{15}$-aryloxy, $C_7$-$C_{15}$-aralkyloxy, $C_1$-$C_{15}$-heteroaryloxy, $C_2$-$C_{15}$-heteroaralkyloxy, $C_1$-$C_{15}$-acyloxy, $C_1$-$C_{15}$-alkylamino, $C_2$-$C_{15}$-alkenylamino, $C_2$-$C_{15}$-alkynylamino, $C_6$-$C_{15}$-arylamino, $C_7$-$C_{15}$-aralkylamino, $C_1$-$C_{15}$-heteroarylamino, $C_2$-$C_{15}$-heteroaralkylamino, $C_1$-$C_{15}$-amido, $C_1$-$C_{15}$-alkylthio, $C_2$-$C_{15}$-alkenylthio, $C_2$-$C_{15}$-alkynylthio, $C_6$-$C_{15}$-arylthio, $C_7$-$C_{15}$-aralkylthio, $C_1$-$C_{15}$-heteroarylthio, $C_2$-$C_{15}$-heteroaralkylthio, $C_1$-$C_{15}$-acylthio, $C_1$-$C_{12}$-thioacyl, $C_1$-$C_{12}$-alkylsulfonyl, $C_2$-$C_{12}$-alkenylsulfonyl, $C_2$-$C_{12}$-alkynylsulfonyl, $C_6$-$C_{12}$-arylsulfonyl, $C_7$-$C_{12}$-aralkylsulfonyl, $C_1$-$C_{12}$-heteroarylsulfonyl, $C_1$-$C_{12}$-heteroaralkylsulfonyl, $C_1$-$C_{12}$-alkylsulfinyl, $C_2$-$C_{12}$-alkenylsulfinyl, $C_2$-$C_{12}$-alkynylsulfinyl, $C_6$-$C_{12}$-arylsulfinyl, $C_7$-$C_{12}$-aralkylsulfinyl, $C_1$-$C_{12}$-heteroarylsulfinyl, $C_1$-$C_{12}$-heteroaralkylsulfinyl, $C_1$-$C_{12}$-alkylphosphonyl, $C_1$-$C_{12}$-alkylphosphate, $C_2$-$C_{12}$-dialkylphosphate, $C_1$-$C_{12}$-alkylammonium, $C_1$-$C_{12}$-alkylsulfonium, $C_1$-$C_{15}$-alkylsilyl, or a substituted version of any of these groups, a —$CO_2Me$, carbonyl imidazole, —CO-D-Glu (OAc)—$CONH_2$, —$CONHNH_2$, —$CONHCH_2CF_3$, or —C(=O)-heteroaryl group.

Example 4

CDDO-Me Derivatives with A-Ring Modifications

CDDO-Me derivatives within the scope of Formula I and containing A-Ring modifications are as follows.

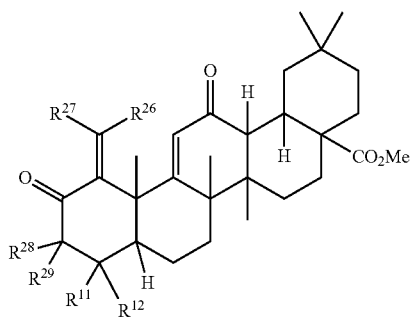

Formula X

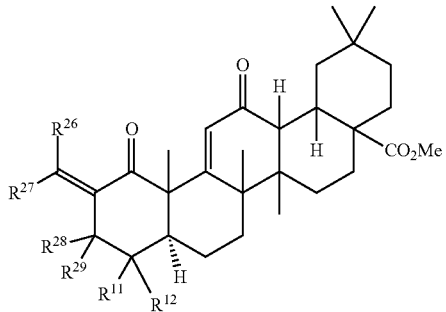

Formula XI

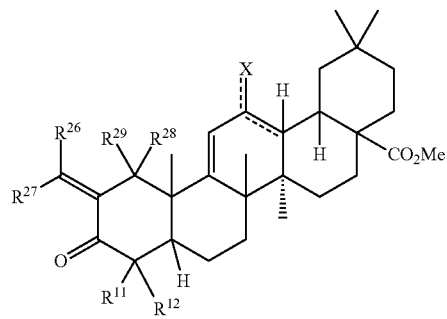

Formula XII

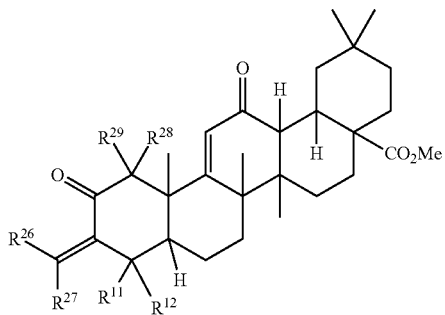

Formula XIII

In accordance with Formulae X-XIII, $R^{11}$ and $R^{12}$ are as defined for Formula I;

X is =O or —OMe;

dashed bonds are present or absent;

$R^{26}$ and $R^{27}$ are independently a hydrogen, halo (e.g., Cl or F), alkylthiyl, or substituted or unsubstituted alkylsulfonyl or alkylsulfonyl —O—;

$R^{28}$ and $R^{29}$ are independently —H, or together are =O.

Exemplary compounds of Formulae X-XIII include compounds 18-82:

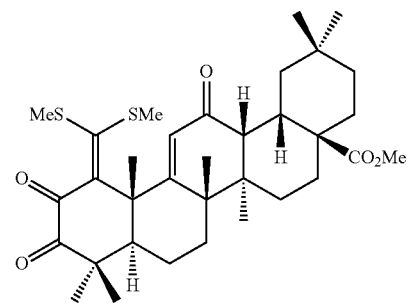

18

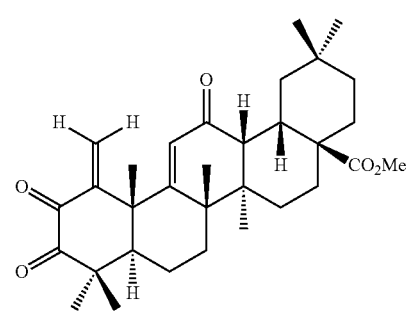

19

20
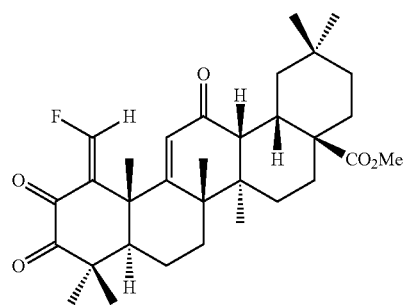
21
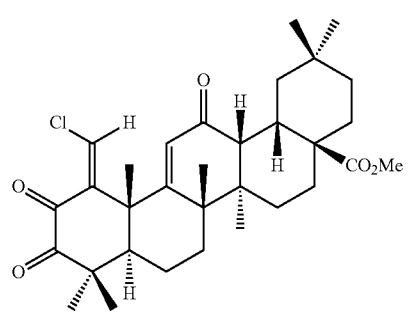
22
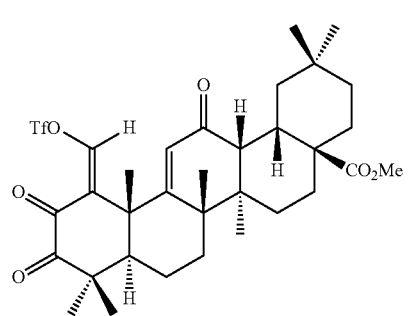
23
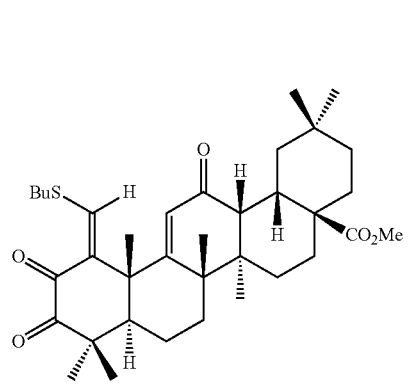
24
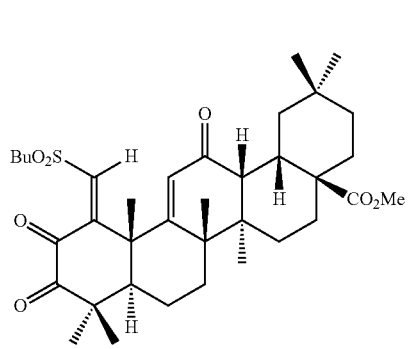
25
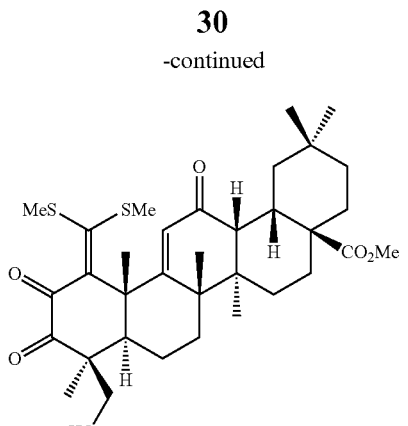
26
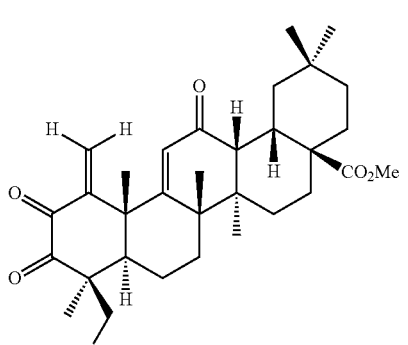
27
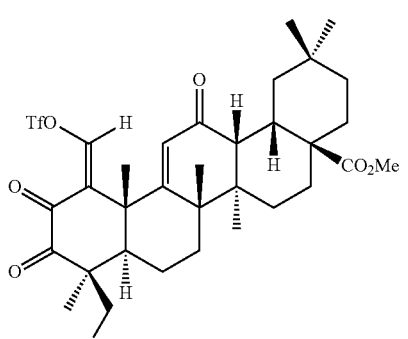
28
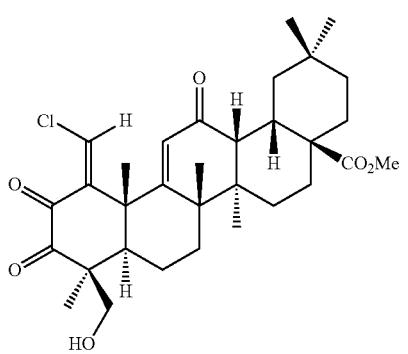

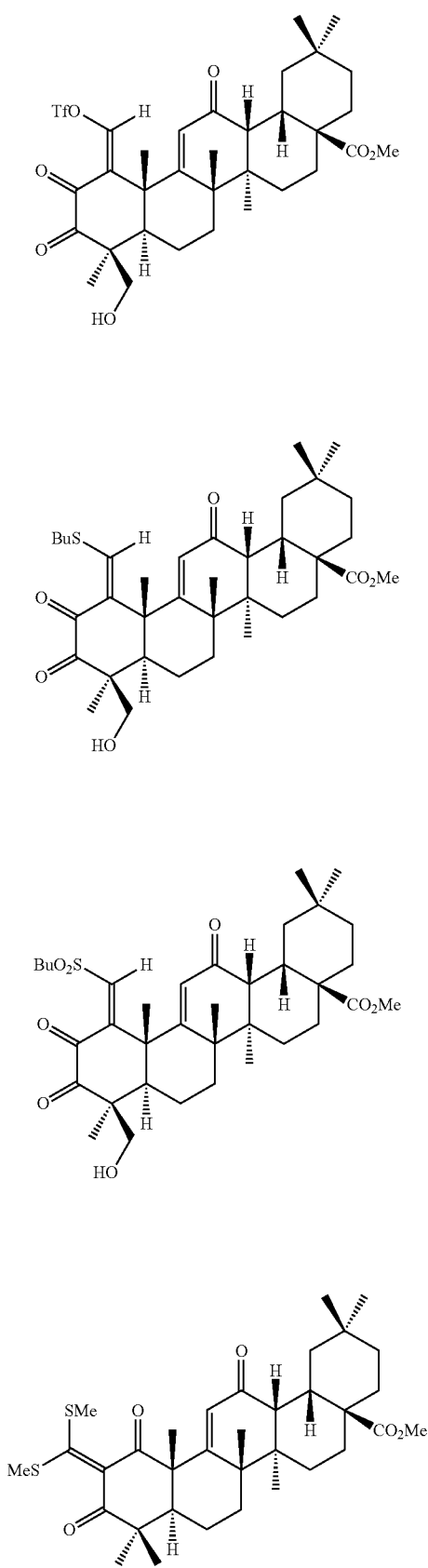
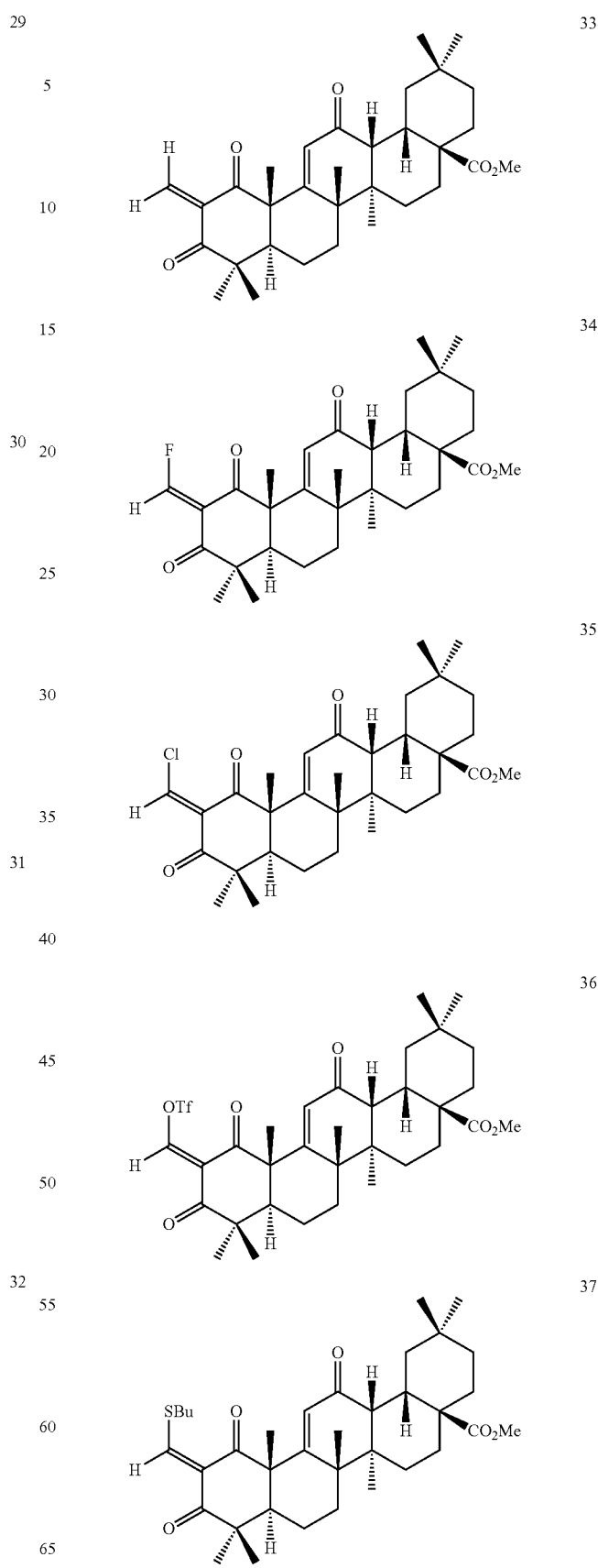

38
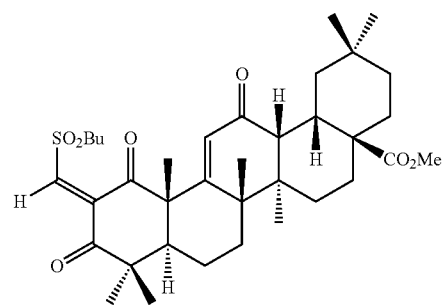
39
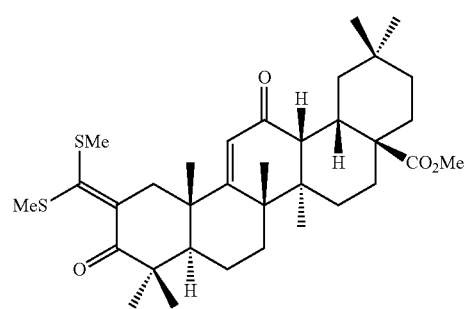
40
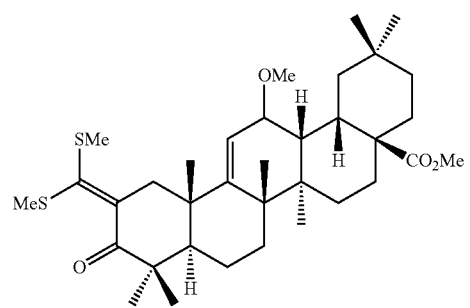
41
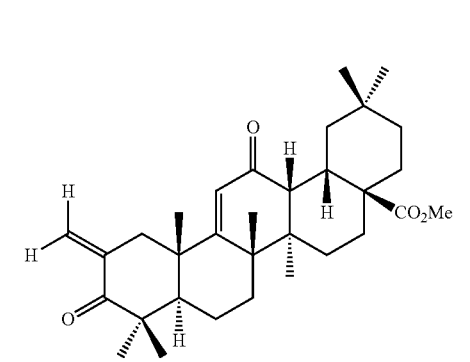
42
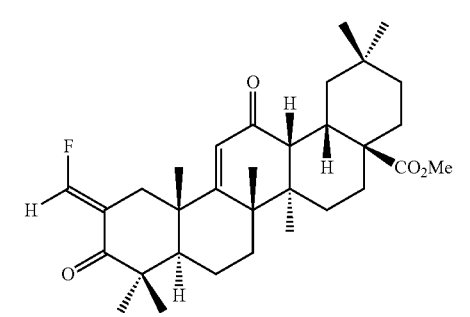
43
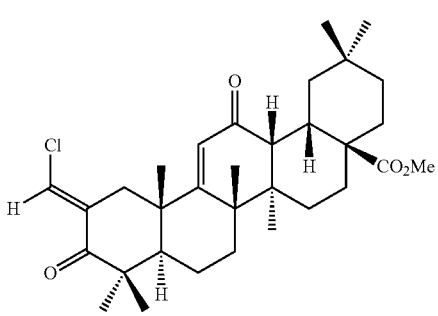
44
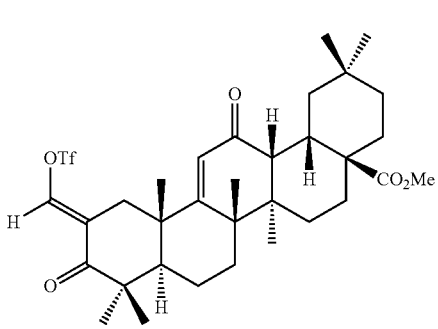
45
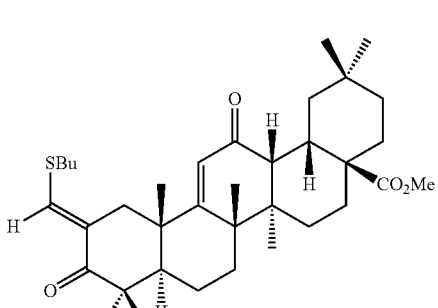
46
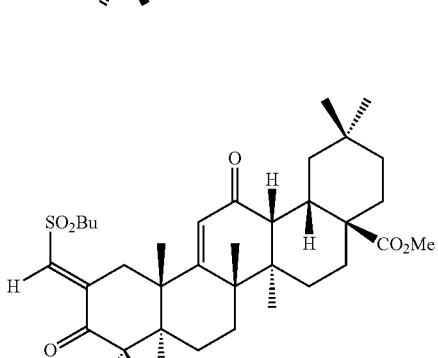
47
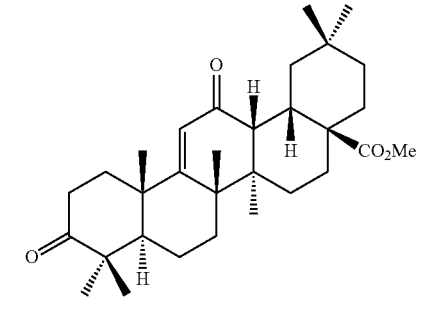

48
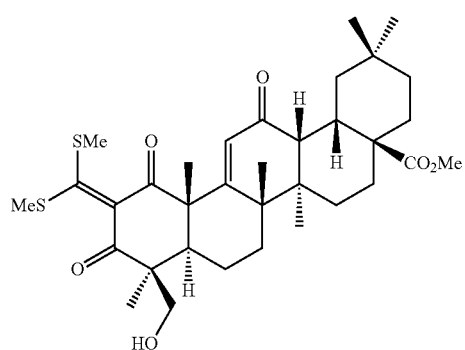
49
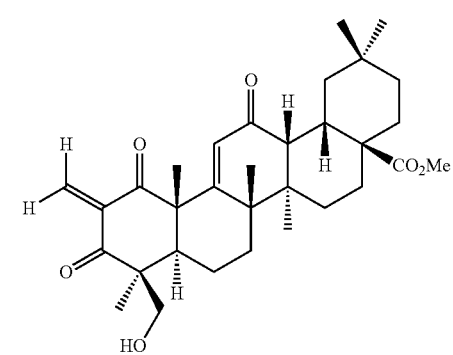
50
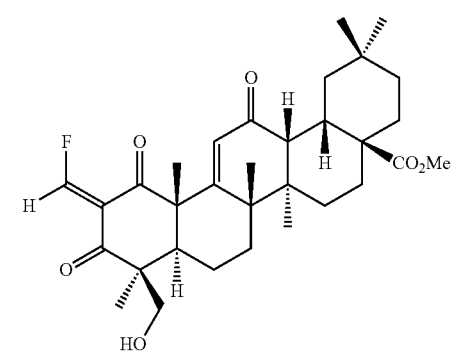
51
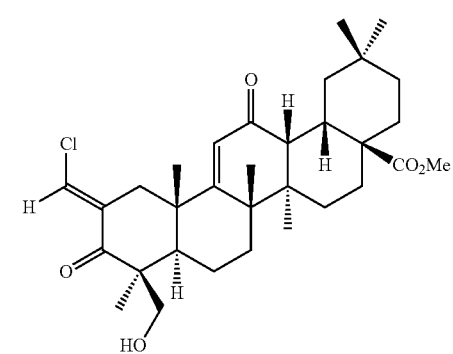
52
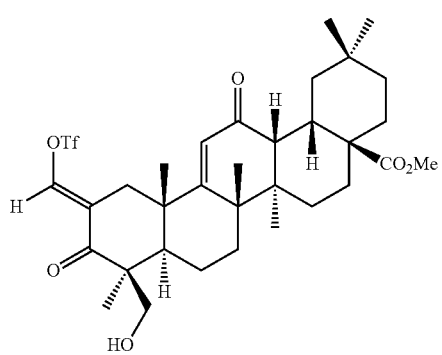
53
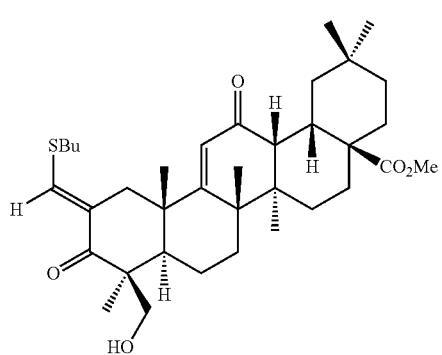
54
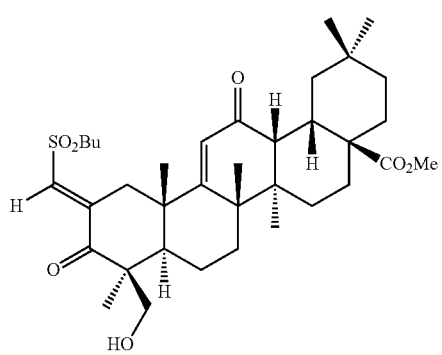
55
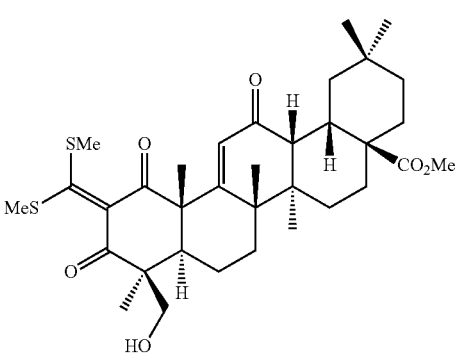

56 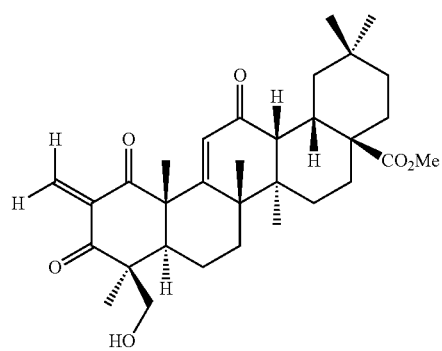
57 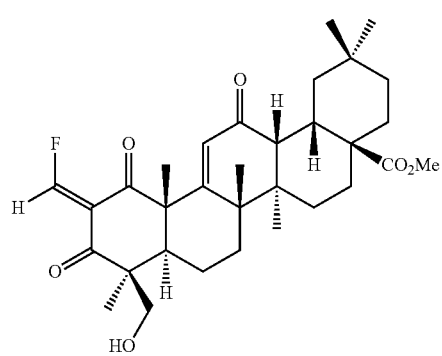
58 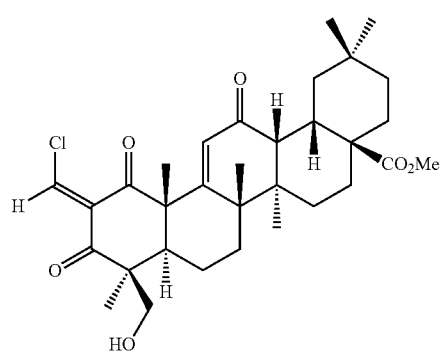
59 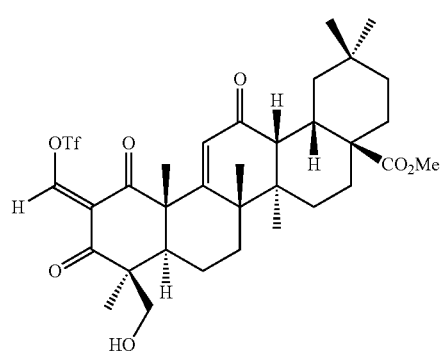
60 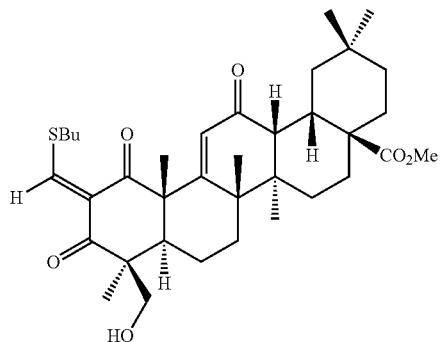
61 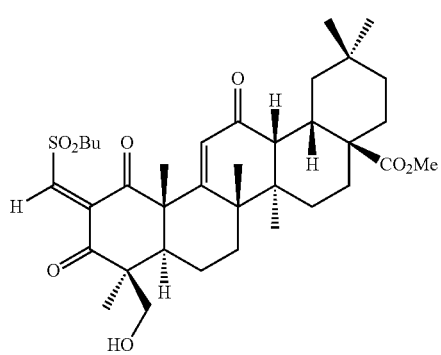
Example 5
Mesylate Derivatives of CDDO-Me
Mesylate derivatives of CDDO-Me of Formula XIV-XVI are also included with the scope of this invention.
Formula XIV
Formula XV
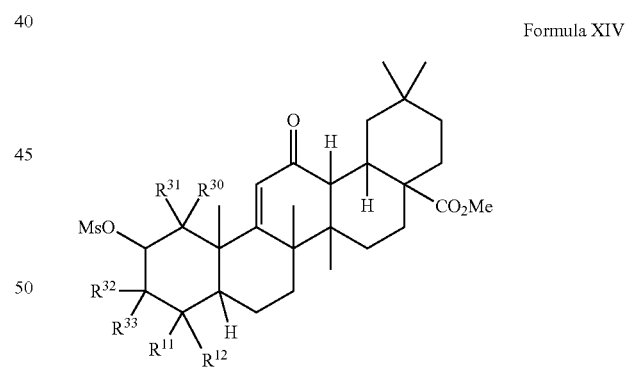
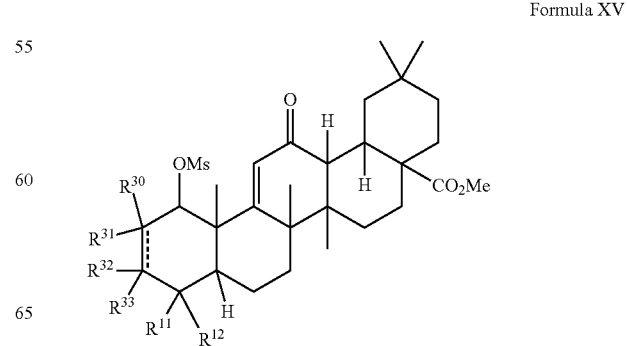

Formula XVI
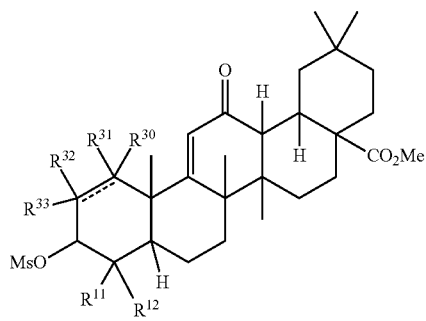
In accordance with Formulae XIV-XVI:
$R^{11}$ and $R^{12}$ are as defined for Formula I;
$R^{30}$, $R^{31}$, $R^{32}$ and $R^{33}$ are each independently a hydrogen, cyano, —OMs, or —CH$_2$OMs group; or
$R^{30}$ and $R^{31}$ or $R^{32}$ and $R^{33}$ together are =CH$_2$; and
dashed bonds are either present or absent.
Exemplary compounds of Formulae XIV-XVI include compounds 62-75:
62
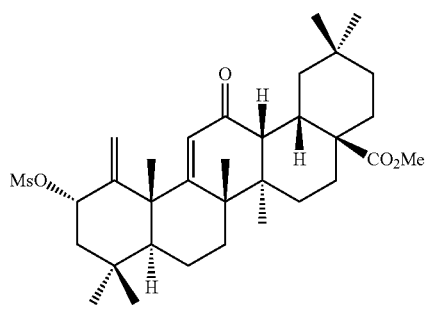
63
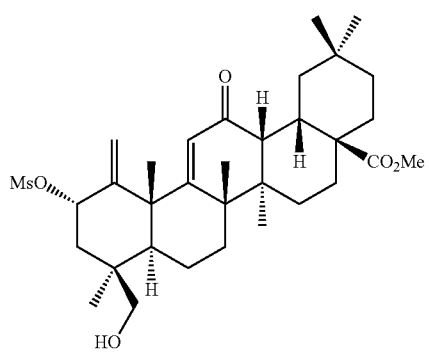
64
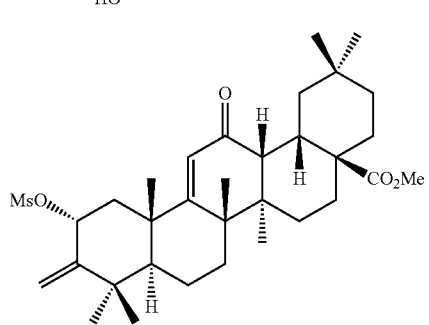
65
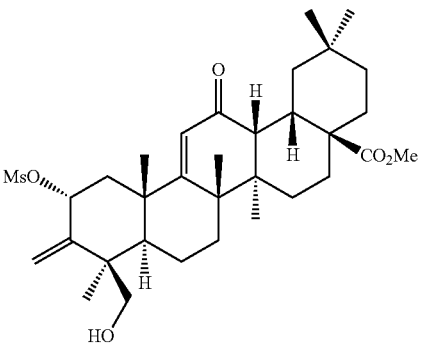
66
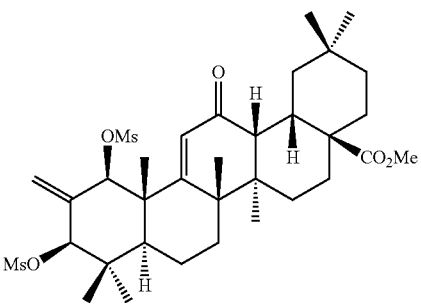
67
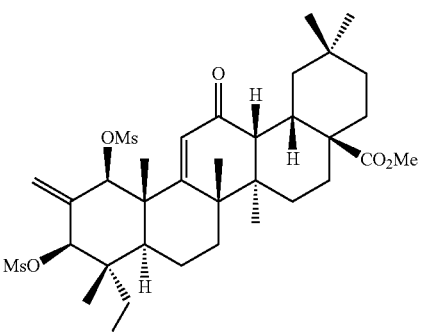
68
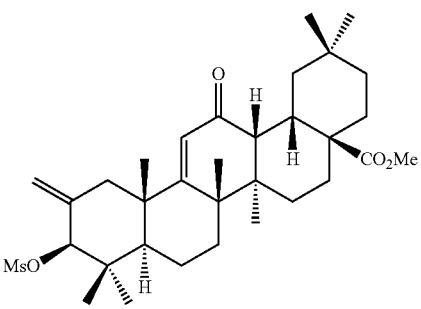
69

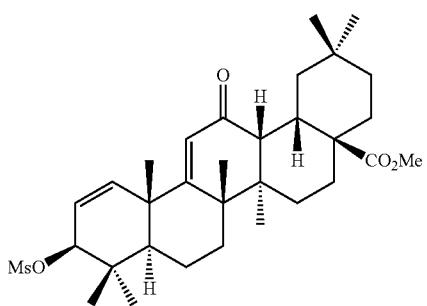
70
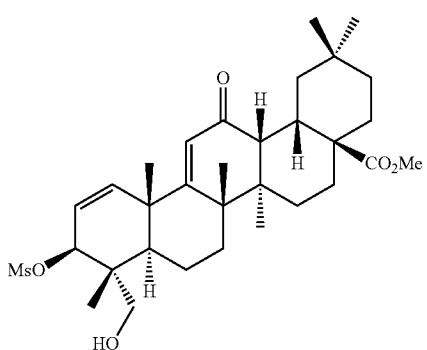
71
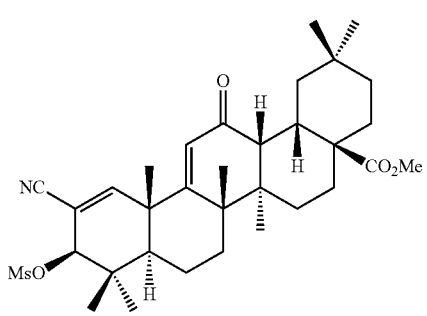
72
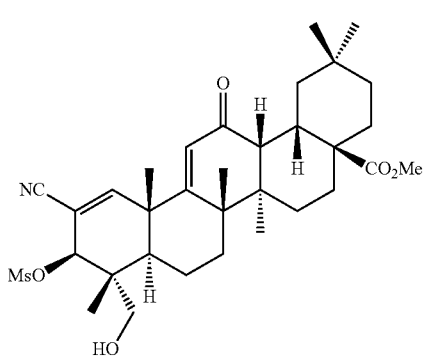
73
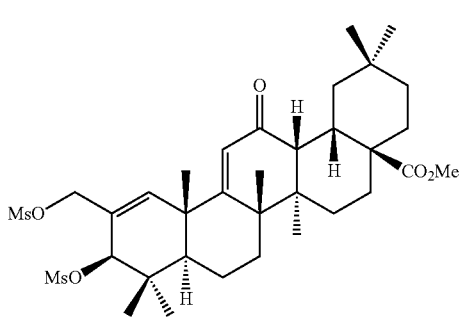
74
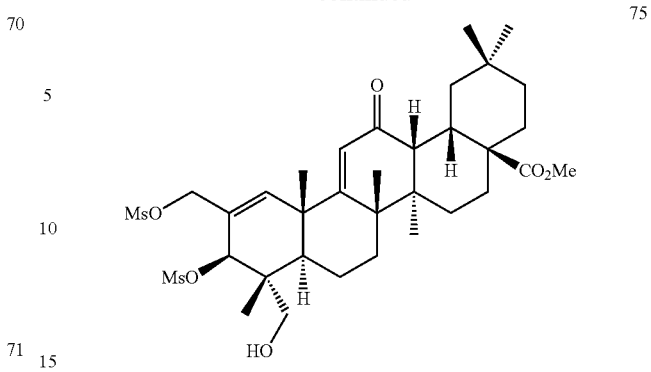
75
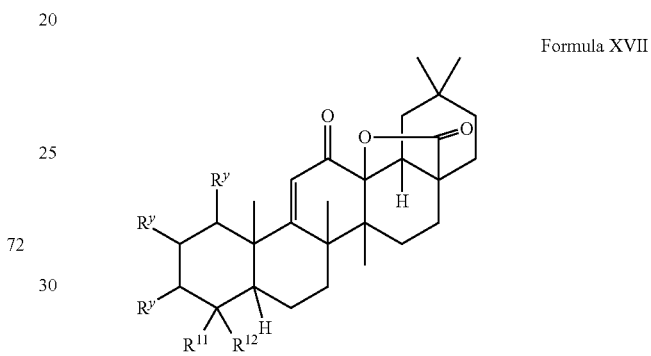
Mesylate derivatives having the structure of Formula XVII are also embodied by the present invention.
Formula XVII
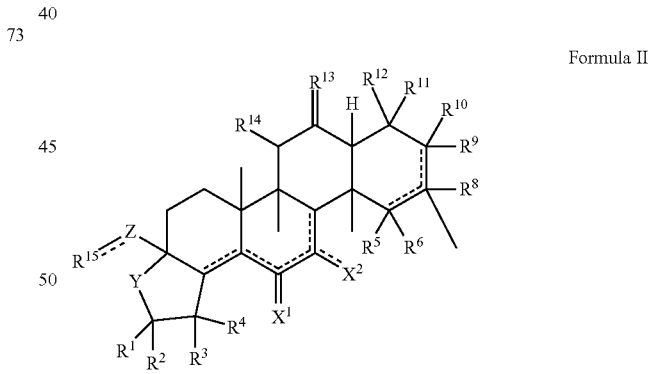
wherein $R^{11}$ and $R^{12}$ are as defined for Formula I; and at least one of $R^y$ is OMs and the remaining $R^y$ are a hydrogen, cyano, —OMs, —CH$_2$OMs, or =CH$_2$ group.
What is claimed is:
1. A compound having the sdstructure of Formula II:
Formula II
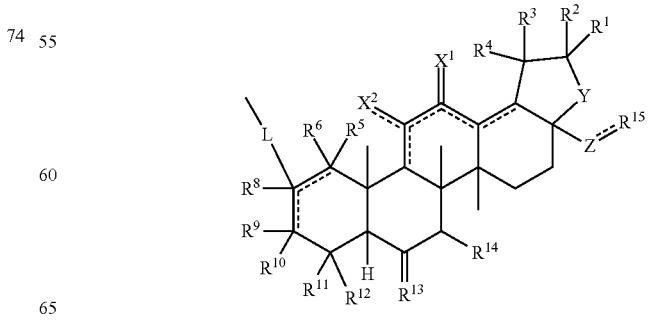

wherein,
at least one of $X^1$ and $X^2$ is $OR^a$, $NR^aR^b$, or $SR^a$, and the other of $X^1$ and $X^2$ is hydrogen, $OR^a$, $NR^aR^b$, or $SR^a$, wherein
- $R^a$ is a hydrogen, cyano, —$CF_3$, nitro, amino, or substituted or unsubstituted heteroaryl group;
- $R^b$ is hydrogen, hydroxyl, alkyl, aryl, aralkyl, acyl, alkoxy, aryloxy, acyloxy, alkylamino, arylamino, amido, or a substituted version of any of these groups;
- provided that $R^a$ is absent when the atom to which it is bound is part of a double bond, further provided that when $R^a$ is absent the atom to which it is bound is part of a double bond;

Y is $CH_2$ or $CH_2$—$CH_2$;

Z is a covalent bond, —C(=O)—, alkanediyl, alkenediyl, alkynediyl, or a substituted version of any of these groups;

the dashed bonds can be independently present or absent;

$R^1$, $R^2$, $R^3$ and $R^4$ are each independently a hydrogen, hydroxyl, alkyl, substituted alkyl, alkoxy or substituted alkoxy group;

at least one of $R^5$, $R^6$, $R^8$, $R^9$ or $R^{10}$ is independently —OMs, —$CH_2$OMs, —C(=O)C≡$CR^a$, —C≡$CCO_2R^a$, —C≡$CSO_2R^a$, —C≡CC(=O)$R^a$ or —$SO_2R^a$, or $R^5$ and $R^6$, or $R^9$ and $R^{10}$ are together =$CR^cR^d$, wherein
- $R^c$ is hydrogen or alkylthiyl, and
- $R^d$ is hydrogen, halo, alkylthiyl, or substituted or unsubstituted alkylsulfonyl or alkylsulfonyl-O—;

the remainder of $R^5$, $R^6$, $R^8$, $R^9$ and $R^{10}$ are independently hydrogen, hydroxyl, halo, cyano, =O, —C≡$CR^a$, —$CO_2R^a$, —$COR^a$, alkyl, alkenyl, alkynyl, aryl, aralkyl, heteroaryl, heteroaralkyl, acyl, alkoxy, aryloxy, acyloxy, alkylamino, arylamino, nitro, amino, amido, —C(O)$R^e$ or a substituted version of any of these groups, wherein
- $R^e$ is hydrogen, hydroxy, halo, amino, hydroxyamino, azido or mercapto; or $C_1$-$C_{15}$-alkyl, $C_2$-$C_{15}$-alkenyl, $C_2$-$C_{15}$-alkynyl, $C_6$-$C_{15}$-aryl, $C_7$-$C_{15}$-aralkyl, $C_1$-$C_{15}$-heteroaryl, $C_2$-$C_{15}$-heteroaralkyl, $C_1$-$C_{15}$-acyl, $C_1$-$C_{15}$-alkoxy, $C_2$-$C_{15}$-alkenyloxy, $C_2$-$C_{15}$-alkynyloxy, $C_6$-$C_{15}$-aryloxy, $C_7$-$C_{15}$-aralkyloxy, $C_1$-$C_{15}$-heteroaryloxy, $C_2$-$C_{15}$-heteroaralkyloxy, $C_1$-$C_{15}$-acyloxy, $C_1$-$C_{15}$-alkylamino, $C_2$-$C_{15}$-dialkylamino, $C_1$-$C_{15}$-alkoxyamino, $C_2$-$C_{15}$-alkenylamino, $C_2$-$C_{15}$-alkynylamino, $C_6$-$C_{15}$-arylamino, $C_7$-$C_{15}$-aralkylamino, $C_1$-$C_{15}$-heteroarylamino, $C_2$-$C_{15}$-heteroaralkylamino, $C_1$-$C_{15}$-alkylsulfonylamino, $C_1$-$C_{15}$-amido, $C_1$-$C_{15}$-alkylsilyloxy, or substituted versions of any of these groups;

$R^{11}$ and $R^{12}$ are each independently hydrogen, hydroxyl, halo, alkyl, alkenyl, alkynyl, aryl, aralkyl, heteroaryl, heteroaralkyl, acyl, alkoxy, aryloxy, aralkoxy, heteroaryloxy, hetero-aralkoxy, acyloxy, alkylamino, dialkylamino, arylamino, aralkylamino, heteroarylamino, heteroaralkylamino, amido, or a substituted version of any of these groups, or $R^{11}$ and $R^{12}$ are taken together and are alkanediyl, alkenediyl, arenediyl, alkoxydiyl, alkenyloxydiyl, alkylaminodiyl, alkenylaminodiyl, or alkenylaminooxydiyl;

$R^{13}$ is hydrogen, hydroxy or oxo;

$R^{14}$ is hydrogen or hydroxyl; and $R^{15}$ is
- a hydrogen, hydroxyl, —$NR^fR^g$, cyano, halo, azido, phosphate, 1,3-dioxoisoindolin-2-yl, mercapto, silyl or —COOH group,
- substituted or unsubstituted versions of $C_1$-$C_{15}$-alkyl, $C_2$-$C_{15}$-alkenyl, $C_2$-$C_{15}$-alkynyl, $C_6$-$C_{15}$-aryl, $C_7$-$C_{15}$-aralkyl, $C_1$-$C_{15}$-heteroaryl, $C_2$-$C_{15}$-heteroaralkyl, $C_1$-$C_{15}$-acyl, $C_1$-$C_{15}$-alkoxy, $C_2$-$C_{15}$-alkenyloxy, $C_2$-$C_{15}$-alkynyloxy, $C_6$-$C_{15}$-aryloxy, $C_7$-$C_{15}$-aralkyloxy, $C_1$-$C_{15}$-heteroaryloxy, $C_2$-$C_{15}$-heteroaralkyloxy, $C_1$-$C_{15}$-acyloxy, $C_1$-$C_{15}$-alkylamino, $C_2$-$C_{15}$-alkenylamino, $C_2$-$C_{15}$-alkynylamino, $C_6$-$C_{15}$-arylamino, $C_7$-$C_{15}$-aralkylamino, $C_1$-$C_{15}$-heteroarylamino, $C_2$-$C_{15}$-heteroaralkylamino, $C_1$-$C_{15}$-amido, $C_1$-$C_{15}$-alkylthio, $C_2$-$C_{15}$-alkenylthio, $C_2$-$C_{15}$-alkynylthio, $C_6$-$C_{15}$-arylthio, $C_7$-$C_{15}$-aralkylthio, $C_1$-$C_{15}$-heteroarylthio, $C_2$-$C_{15}$-heteroaralkylthio, $C_1$-$C_{15}$-acylthio, $C_1$-$C_{12}$-thioacyl, $C_1$-$C_{12}$-alkylsulfonyl, $C_2$-$C_{12}$-alkenylsulfonyl, $C_2$-$C_{12}$-alkynylsulfonyl, $C_6$-$C_{12}$-arylsulfonyl, $C_7$-$C_{12}$-aralkylsulfonyl, $C_1$-$C_{12}$-heteroarylsulfonyl, $C_1$-$C_{12}$-heteroaralkylsulfonyl, $C_1$-$C_{12}$-alkylsulfinyl, $C_2$-$C_{12}$-alkenylsulfinyl, $C_2$-$C_{12}$-alkynylsulfinyl, $C_6$-$C_{12}$-aryl sulfinyl, $C_7$-$C_{12}$-aralkylsulfinyl, $C_1$-$C_{12}$-heteroarylsulfinyl, $C_1$-$C_{12}$-heteroaralkylsulfinyl, $C_1$-$C_{12}$-alkylphosphonyl, $C_1$-$C_{12}$-alkylphosphate, $C_2$-$C_{12}$-dialkylphosphate, $C_1$-$C_{12}$-alkylammonium, $C_1$-$C_{12}$-alkylsulfonium, $C_1$-$C_{15}$-alkylsilyl, or a substituted version of any of these groups,
- a —$CO_2$Me, carbonyl imidazole, —CO-D-Glu(OAc)$_4$, —$CONH_2$, —$CONHNH_2$, —$CONHCH_2CF_3$, or —C(=O)-heteroaryl group, or Z and $R^{15}$ form a three to seven-membered ring, wherein
- $R^f$ and $R^g$ are independently hydrogen, hydroxyl, alkyl, alkenyl, alkynyl, aryl, aralkyl, heteroaryl, heteroaralkyl, acyl, alkoxy, alkenyloxy, alkynyloxy, aryloxy, aralkoxy, heteroaryloxy, heteroaralkoxy, thioacyl, alkylsulfonyl, alkenylsulfonyl, alkynylsulfonyl, arylsulfonyl, aralkylsulfonyl, heteroarylsulfonyl, or heteroaralkylsulfonyl, or a substituted version of any of these groups;

L is —C(=O)—, —C≡C—, —C≡C—N(—R)—, —C(=O)—N(—R)—, or —C≡C—C(=O)—, wherein
R is hydrogen, or an alkyl, aryl, alkenyl, or alkynyl group, or L is —C≡C—R—C≡C—, wherein
R is an alkyl, aryl, alkenyl, or alkynyl group.

2. A pharmaceutical composition comprising the compound of claim 1 in admixture with a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 9,539,287 B2 | Page 1 of 1 |
| APPLICATION NO. | : 14/496488 | |
| DATED | : January 10, 2017 | |
| INVENTOR(S) | : Gordon W. Gribble | |

It is certified that error appears in the above-identified patent and that said Letters Patent is hereby corrected as shown below:

In the Claims

Column 42, Line 39, delete "sdstructure"
Column 42, Line 39, add --structure--

Signed and Sealed this
Twenty-fifth Day of April, 2017

Michelle K. Lee
*Director of the United States Patent and Trademark Office*